(12) United States Patent
Kunz et al.

(10) Patent No.: US 6,369,002 B1
(45) Date of Patent: Apr. 9, 2002

(54) N-HETEROARYL-SUBSTITUTED PYRIDINE DERIVATIVES AND THEIR USE AS HERBICIDES

(75) Inventors: Walter Kunz, Oberwil; Kurt Nebel, Hochwald, both of (CH)

(73) Assignee: Syngenta Crop Properties, Inc., Greensboro, NC (US)

( * ) Notice: Subject to any disclaimer, the term of this patent is extended or adjusted under 35 U.S.C. 154(b) by 0 days.

(21) Appl. No.: 09/702,101

(22) Filed: Oct. 30, 2000

Related U.S. Application Data

(63) Continuation of application No. PCT/EP99/02815, filed on Apr. 26, 1999.

(30) Foreign Application Priority Data

Apr. 28, 1998 (CH) .............................................. 0959/98

(51) Int. Cl.⁷ ...................... C07D 401/04; A01N 43/54; A01N 43/58
(52) U.S. Cl. ...................... 504/238; 504/243; 504/240; 544/236; 544/237; 544/238; 544/282; 544/285; 544/300; 544/310
(58) Field of Search ............................... 544/238, 300, 544/310, 236, 237, 282, 285; 504/238, 243, 240

(56) References Cited

U.S. PATENT DOCUMENTS

| | | | |
|---|---|---|---|
| 4,406,689 A | 9/1983 | Anderson et al. ............... | 71/92 |
| 5,112,383 A | 5/1992 | Rueb et al. ..................... | 71/92 |
| 5,250,504 A | 10/1993 | Maravetz et al. ............ | 504/280 |
| 5,306,694 A | 4/1994 | Phillips et al. ............... | 504/253 |

FOREIGN PATENT DOCUMENTS

| | | |
|---|---|---|
| DE | 39 17 469 A | 12/1990 |
| DE | 19 518 054 A | 9/1996 |
| DE | 195 30 606 A | 2/1997 |
| EP | 0 370 332 A | 5/1990 |
| JP | 58 213 776 A | 12/1983 |
| WO | WO 92 00976 A | 1/1983 |
| WO | WO 92 16510 A | 10/1992 |
| WO | WO 93 18008 A | 9/1993 |
| WO | WO 97 02243 A | 1/1997 |
| WO | WO 98 27082 | 6/1998 |

OTHER PUBLICATIONS

J. Org. Chem., vol. 48, No. 8, 1993, pp. 1375–1377.

*Primary Examiner*—Bernard Dentz
(74) *Attorney, Agent, or Firm*—William A. Teoli, Jr.

(57) ABSTRACT

Compounds of formula 1

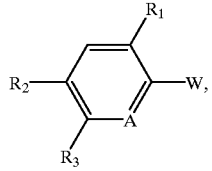

(I)

wherein

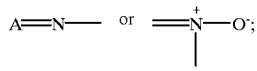

$R_1$ is hydrogen, fluorine, chlorine, bromine or methyl;

$R_2$ is $C_1$–$C_4$alkyl, $C_1$–$C_4$halogenalkyl, halogen, hydroxy, $C_1$–$C_4$alkoxy, $C_1$–$C_4$halogenalkoxy, nitro, amino or cyano;

W is a

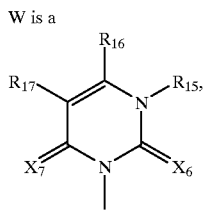

(W₁)

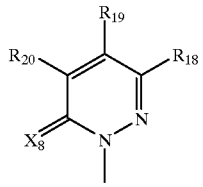

(W₂)

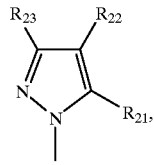

(W₃)

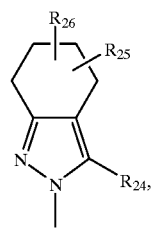

(W₄)

-continued
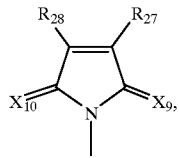 (W₅)
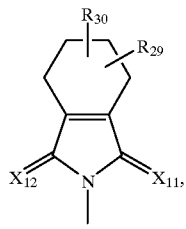 (W₆)
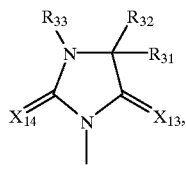 (W₇)
-continued
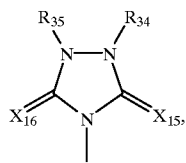 (W₈)
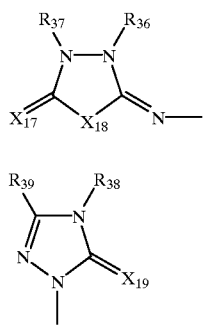 (W₉) or
(W₁₀) group; and
$R_3$, $R_{15}$ to $R_{39}$ and $X_6$ to $X_{19}$ are as defined in claim 1, and the agrochemically acceptable salts and stereoisomers of these compounds of formula I are suitable for use as herbicides.
6 Claims, No Drawings

N-HETEROARYL-SUBSTITUTED PYRIDINE DERIVATIVES AND THEIR USE AS HERBICIDES

This is a continuation of International Application No. PCT/EP99/02815, filed Apr. 26, 1999, the contents of which are incorporated herein by reference.

The present invention relates to new, herbicidally active, substituted n-pyridyl-nitrogen heterocycles, methods for the preparation thereof, compositions comprising these compounds, and the use thereof for weed control, especially in crops of cultivated plants, such as grain, cereals, maize, rice, cotton, soybeans, rape, sorghum, sugar cane, sugar beet, sunflowers, vegetables, plantations, and forage crops or for the inhibition of plant growth and for non-selective control of weeds.

N-Phenyl and N-pyridylpyrazole compounds and N-pyridyltetramethylenetriazolidinediones with a herbicidal action are described, for example, in EP-A-0 370 332, DE-A-3 917 469, DE-A-19 518 054, DE-A-19 530 606, U.S. Pat. Nos. 5,306,694 and 4,406,689.

Also known as herbicides are N-pyridylimides, N-(2-pyridyl)pyridazinones and 3-phenyluracils, as described for example in WO 92/00976, JP-A-58-213 776 and EP-A-0 438 209.

N-(Phenyl)tetrahydroimidazoles with a herbicidal action are described for example in U.S. Pat. No. 5,112,383.

New substituted n-pyridylnitrogen heterocycles have now been found with herbicidal and growth-inhibiting properties.

Accordingly, the invention relates to compounds of formula I

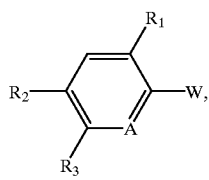
(I)

wherein

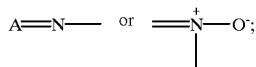

$R_1$ is hydrogen, fluorine, chlorine, bromine or methyl;

$R_2$ is $C_1-C_4$alkyl, $C_1-C_4$halogenalkyl, halogen, hydroxy, $C_1-C_4$alkoxy, $C_1-C_4$halogenalkoxy, nitro, amino or cyano;

$R_3$ is cyano or $R_4C(O)$—;

$R_4$ is hydrogen, fluorine, chlorine, $C_1-C_8$alkyl, $C_2-C_8$alkenyl, $C_2-C_8$alkinyl, $C_3-C_6$cycloalkyl, $C_1-C_8$halogenalkyl, cyano-$C_1-C_4$alkyl, $C_2-C_8$halogenalkenyl, $C_1-C_4$alkoxy-$C_1-C_4$alkyl, $C_3-C_6$alkenyloxy-$C_1-C_4$alkyl, $C_1-C_4$alkylthio-$C_1-C_4$alkyl, phenyl, phenyl substituted once to three times by halogen, $C_1-C_4$alkyl or $C_1-C_4$halogenalkyl, benzyl, benzyl substituted once to three times on the phenyl ring by halogen, $C_1-C_4$alkyl or $C_1-C_4$halogenalkyl; or $R_3$ is $R_5X_1C(O)$—;

$X_1$ is oxygen, sulfur,

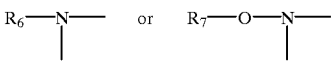

$R_5$ is hydrogen, $C_1-C_8$alkyl, $C_3-C_8$alkenyl, $C_3-C_8$alkinyl, $C_3-C_6$cycloalkyl, $C_3-C_6$cycloalkyl-$C_1-C_6$alkyl, $C_1-C_8$halogenalkyl, $C_3-C_8$halogenalkenyl, cyano-$C_1-C_4$alkyl, $C_1C_4$alkoxy-$C_1-C_4$alkyl, $C_3-C_6$alkenyloxy-$C_1-C_4$alkyl, (oxiranyl)-$CH_2$—, oxetanyl, $C_1-C_4$alkylthio-$C_1-C_4$alkyl, phenyl, phenyl substituted once to three times by halogen, $C_1-C_4$alkyl or $C_1-C_4$halogenalkyl, benzyl, benzyl substituted once to three times on the phenyl ring by halogen, $C_1-C_4$alkyl or $C_1-C_4$-halogenalkyl, phenyl-$C_2-C_6$alkyl, $C_1-C_6$alkyl-CO—$C_1-C_4$alkyl,

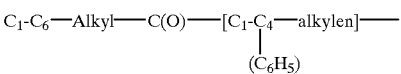

$R_8X_2C(O)$—$C_1-C_6$-alkyl,

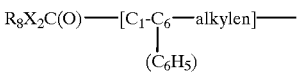

or $R_8X_2C(O)$—$C_3-C_6$cycloalkyl;

$X_2$ is oxygen, sulfur,

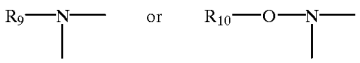

$R_8$ is hydrogen, $C_1-C_8$alkyl, $C_3-C_8$alkenyl, $C_3-C_8$alkinyl, $C_3-C_6$cycloalkyl, $C_1-C_8$halogenalkyl $C_3-C_8$halogenalkenyl, cyano-$C_1-C_4$alkyl, $C_1-C_4$alkoxy-$C_1-C_4$alkyl, $C_3-C_6$alkenyloxy-$C_1-C_4$alkyl, (oxiranyl)-$CH_2$—, oxetanyl, $C_1-C_4$alkylthio-$C_1-C_4$alkyl, phenyl, phenyl substituted once to three times by halogen, $C_1-C_4$alkyl or $C_1-C_4$halogenalkyl, benzyl, benzyl substituted once to three times on the phenyl ring by halogen, $C_1-C_4$alkyl or $C_1-C_4$halogenalkyl, or phenyl-$C_2-C_6$alkyl; $R_6$, $R_7$, $R_9$ and $R_{10}$ are independently of one another hydrogen, $C_1-C_8$alkyl, $C_3-C_8$alkenyl, $C_3-C_8$alkinyl, $C_1-C_8$halogenalkyl or benzyl; or $R_3$ is $B_1$—$C_1-C_8$alkyl, $B_1$—$C_2-C_8$alkenyl, $B_1$—$C_2-C_8$alkinyl, $B_1$—$C_1-C_8$halogenalkyl, $B_1$—$C_2-C_8$halogenalkenyl, $B_1$—$C_1-C_4$alkoxy-$C_1-C_4$alkyl, $B_1$—$C_1-C_4$alkylthio-$C_1-C_4$alkyl or $B_1$—$C_3-C_6$cycloalkyl;

$B_1$ is hydrogen, cyano, hydroxy, $C_1-C_8$alkoxy, $C_3-C_8$alkenyloxy, $R_{11}X_3C(O)$—, $C_1-C_4$alkylcarbonyl or $C_1-C_4$halogenalkylcarbonyl;

$X_3$ has the same meaning as $X_2$;

$R_{11}$ has the same meaning as $R_8$; or $R_3$ is $B_2$—$C(R_{12})$=$CH$—;

$B_2$ is nitro, cyano or $R_{13}X_4C(O)$—;

$R_{12}$ is cyano or $R_{14}X_5C(O)$—;

$X_4$ and $X_5$ have the same meaning as $X_2$; and $R_{13}$ and $R_{14}$ have the same meaning as $R_8$;

W is a (W₁) 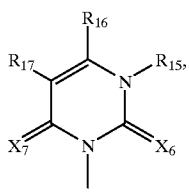

(W₂) 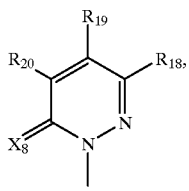

(W₃) 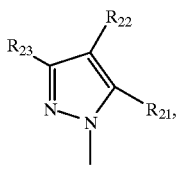

(W₄) 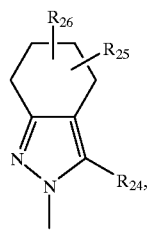

(W₅) 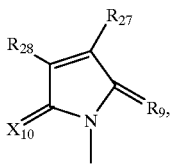

(W₆) 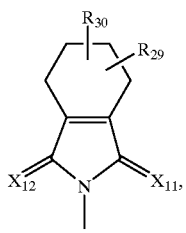

(W₇) 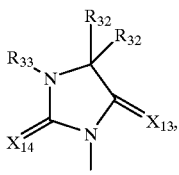

-continued

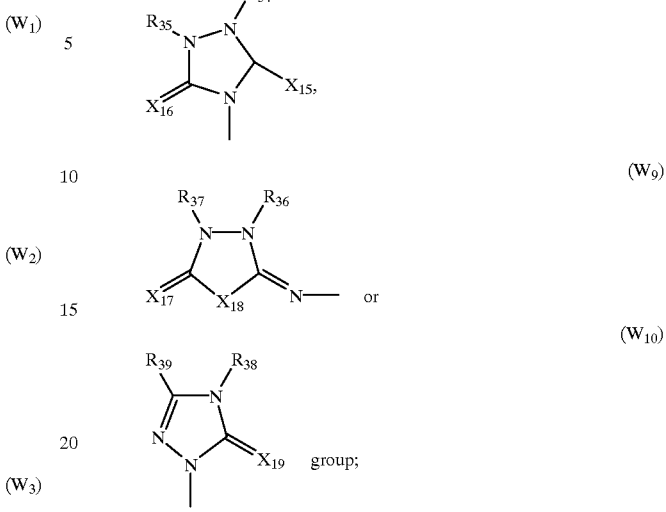

$R_{15}$ is $C_1$–$C_3$alkyl, $C_1$–$C_3$halogenalkyl or amino;

$R_{16}$ is $C_1$–$C_3$halogenalkyl, $C_1$–$C_3$alkyl-S(O)$_{n1}$, $C_1$–$C_3$halogenalkyl-S(O)$_{n1}$ or cyano; or $R_{16}$ and $R_{15}$ together form a $C_3$- or $C_4$alkylene or $C_3$- or $C_4$alkenylene bridge which may be substituted by halogen, $C_1$–$C_3$halogenalkyl or cyano;

$n_1$ is 0, 1 or 2;

$R_{17}$ is hydrogen, $C_1$–$C_3$alkyl, halogen, $C_1$–$C_3$halogenalkyl or cyano; or $R_{17}$ and $R_{16}$ together form a $C_3$- or $C_4$alkylene or $C_3$- or $C_4$alkenylene bridge which may be substituted by halogen, $C_1$–$C_3$halogenalkyl or cyano;

$R_{18}$ is hydrogen, $C_1$–$C_3$alkyl, halogen or cyano;

$R_{19}$ is $C_1$–$C_3$halogenalkyl; or $R_{19}$ and $R_{18}$ together form a $C_3$- or $C_4$alkylene or $C_3$- or $C_4$alkenylene bridge which may be substituted by halogen, $C_1$–$C_3$halogenalkyl or cyano;

$R_{20}$ is hydrogen or $C_1$–$C_3$alkyl or halogen; or $R_{20}$ and $R_{19}$ together form a $C_3$- or $C_4$alkylene or $C_3$- or $C_4$alkenylene bridge which may be substituted by halogen, $C_1$–$C_3$halogenalkyl or cyano;

$R_{21}$ is hydrogen, $C_1$–$C_3$alkyl, halogen, $C_1$–$C_3$halogenalkyl, $R_{40}$O—, $R_{41}$S(O)$_{n2}$, $R_{42}(R_{43})$N, $R_{45}(R_{46})$N—C($R_{44}$)=N—, hydroxy, nitro or N≡C—S—;

$R_{40}$ is $C_1$–$C_3$alkyl, $C_1$–$C_3$halogenalkyl, $C_2$–$C_4$alkenyl, $C_3$- or $C_4$alkinyl or $C_1$–$C_5$alkoxycarbonyl-$C_1$–$C_4$alkyl;

$R_{41}$ is $C_1$–$C_4$alkyl or $C_1$–$C_4$halogenalkyl;

$n_2$ is 0, 1 or 2;

$R_{42}$ is hydrogen, $C_1$–$C_4$alkyl, $C_1$–$C_4$halogenalkyl, $C_3$–$C_6$cycloalkyl, OHC— or $C_1$–$C_4$alkylcarbonyl;

$R_{43}$, $R_{44}$, and $R_{46}$ are independently of one another hydrogen or $C_1$–$C_4$alkyl;

$R_{45}$ is $C_1$–$C_4$alkyl;

$R_{22}$ is hydrogen, $C_1$–$C_4$alkyl, halogen, $C_1$–$C_4$halogenalkyl, $C_2$–$C_4$alkenyl, $C_3$–$C_5$halogenalkenyl, $C_3$- or $C_4$alkinyl, $C_1$–$C_4$alkoxy, $C_1$–$C_4$alkylcarbonyl, $C_1$–$C_4$halogenalkylcarbonyl, $C_2$–$C_4$alkenylcarbonyl, $C_2$–$C_4$halogenalkenylcarbonyl, $C_2$–$C_4$alkinylcarbonyl, $C_2$–$C_4$halogenalkinylcarbonyl, $C_1$–$C_4$alkylcarbamoyl, $C_1$–$C_4$alkylS(O)$_{n3}$, $C_3$- or $C_4$alkinylS(O)$_{n3}$, OHC—, nitro, amino, cyano or N≡C—S—;

$n_3$ is 0, 1 or 2;

$R_{23}$ and $R_{24}$ independently of one another are hydrogen, $C_1$–$C_4$alkyl, halogen, $C_1$–$C_4$halogenalkyl or cyano $R_{25}$ and $R_{26}$ are independently of one another hydrogen, methyl, halogen, hydroxy or =O;

$R_{27}$ and $R_{28}$ are independently of one another hydrogen, $C_1$–$C_4$alkyl or $C_1$–$C_4$halogenalkyl;

$R_{29}$ and $R_{30}$ are independently of one another hydrogen, $C_1$–$C_3$alkyl or halogen;

$R_{31}$ and $R_{32}$ independently of one another are hydrogen or $C_1$–$C_4$alkyl; or $R_{31}$ and $R_{32}$ together form the group

$R_{47}$ and $R_{48}$ are independently of one another $C_1$–$C_4$alkyl; or $R_{47}$ and $R_{48}$ together form a $C_4$ or $C_5$alkylene bridge;

$R_{33}$ is hydrogen or $C_1$–$C_3$alkyl; or $R_{33}$ together with $R_{32}$ forms a $C_3$–$C_5$alkylene bridge which may be broken by oxygen and/or substituted by halogen, $C_1$–$C_4$alkyl, $C_2$–$C_4$alkenyl, $C_1$–$C_3$alkylcarbonyloxy, $C_1$–$C_3$alkylsulfonyloxy, hydroxy or =O;

$R_{34}$, $R_{35}$, $R_{36}$ and $R_{37}$ are independently of one another hydrogen, $C_1$–$C_3$alkyl, $C_3$- or $C_4$alkenyl or $C_3$–$C_5$alkinyl; or $R_{34}$ and $R_{35}$ on the one hand and $R_{36}$ and $R_{37}$ on the other each form a $C_2$–$C_5$alkylene or $C_3$–$C_5$alkenylene bridge, which may be broken by oxygen, —C(O)—, sulfur, or —S(O)$_2$—;

$R_{38}$ is hydrogen, $C_1$–$C_4$alkyl, $C_1$–$C_4$halogenalkyl, $C_3$- or $C_4$alkenyl or $C_3$- or $C_4$alkinyl;

$R_{39}$ is hydrogen, $C_1$–$C_4$alkyl, $C_1$–$C_3$alkoxy-$C_1$- or —$C_2$alkyl, $C_1$–$C_4$halogenalkyl, $C_3$- or $C_4$alkenyl, $C_3$- or $C_4$halogenalkenyl or $C_3$- or $C_4$alkinyl; or $R_{39}$ and $R_{38}$ together form a $C_3$–$C_5$alkylene bridge; and $X_6$, $X_7$, $X_8$, $X_9$, $X_{10}$, $X_{11}$, $X_{12}$, $X_{13}$, $X_{14}$, $X_{15}$, $X_{16}$, $X_{17}$, $X_{18}$ and $X_{19}$ are independently of one another oxygen or sulfur, and the agrochemically acceptable salts and stereoisomers of these compounds of formula I.

In the definitions listed hereinbefore, halogen is taken to mean iodine, preferably fluorine, chlorine and bromine.

The alkyl, alkenyl and alkinyl groups mentioned in the substituent definitions may be straight-chained or branched, as is also the case with the alkyl, alkenyl and alkinyl part of the alkylcarbonyl, alkylcarbonyloxy, alkylcarbonylalkyl, alkenyloxy, alkenyloxyalkyl, alkenylcarbonyl, alkinylcarbonyl, alkylcarbamoyl, hydroxyalkyl, cyanoalkyl, alkoxyalkyl, alkylthio, alkylthioalkyl, alkylthio-C(O)—, alkylS(O)$_{n3}$, alkylsulfonyloxy, alkylaminocarbonyl, dialkylaminocarbonyl, alkylcarbonylalkyl, $B_1$alkyl, $B_1$alkenyl, $B_1$alkinyl, HOC(O)alkyl, phenylalkyl and $R_8X_2C(O)$—$C_1$–$C_6$alkyl groups.

Alkyl groups are for example methyl, ethyl, n-propyl, isopropyl, n-butyl, sec-butyl, isobutyl, tert-butyl and the various isomeric pentyl, hexyl, heptyl and octyl radicals. Preferred are methyl, ethyl, n-propyl, isopropyl and n-butyl.

Examples of alkenyls are vinyl, allyl, methallyl, 1-methylvinyl, but-2-en-1-yl, pentenyl, 2-hexenyl, 3-heptenyl and 4-octenyl, preferably alkenyl radicals with a chain length of 3 to 5 carbon atoms.

Examples of alkinyls are ethinyl, propargyl, 1-methylpropargyl, 3-butinyl, but-2-in-1-yl, 2-methylbutin-2-yl, but-3-in-2-yl, 1-pentinyl, pent-4-in-1-yl or 2-hexinyl, preferably alkinyl radicals with a chain length of 2 to 4 carbon atoms.

Alkyl groups substituted once or more, especially once to three times, by halogen are suitable as the halogenalkyl, the halogen being iodine, especially fluorine, chlorine and bromine, for example fluoromethyl, difluoromethyl, trifluoromethyl, chloromethyl, dichloromethyl, trichloromethyl, 2-fluoroethyl, 2,2-difluoroethyl, 2-chloroethyl, 2,2-dichloroethyl, 2,2,2-trifluoroethyl, 2,2,2-trichloroethyl and pentafluoroethyl.

Suitable halogenalkenyls are alkenyl groups substituted once or more by halogen, the halogen being bromine, iodine and especially fluorine and chlorine, for example 2- and 3-fluoropropenyl, 2- and 3-chloropropenyl, 2- and 3-bromopropenyl, 2,3,3-trifluoropropenyl, 3,3,3-trifluoropropenyl, 2,3,3-trichloropropenyl, 4,4,4-trifluorobut-2-en-1-yl and 4,4,4-trichlorobut-2-en-1-yl. Of the alkenyl radicals substituted once, twice or three times by halogen, those with a chain length of 3 or 4 carbon atoms are preferred. The alkenyl groups may be substituted by halogen on saturated or unsaturated carbon atoms.

Suitable halogenalkinyls are for example alkinyl groups substituted by halogen, the halogen being bromine, iodine and especially fluorine and chlorine, for example 3-fluoropropinyl, 3-chloropropinyl, 3-bromopropinyl, 3,3,3-trifluoropropinyl and 4,4,4-trifluorobut-2-in-1-yl.

Alkylsulfonyl is for example methylsulfonyl, ethylsulfonyl, propylsulfonyl, isopropylsulfonyl, n-butylsulfonyl, isobutylsulfonyl, sec-butylsulfonyl, tert-butylsulfonyl; preferably methylsulfonyl and ethylsulfonyl.

Halogenalkylsulfonyl is for example fluoromethylsulfonyl, difluoromethylsulfonyl, trifluoromethylsulfonyl, chloromethylsulfonyl, trichloromethylsulfonyl, 2-fluoroethylsulfonyl, 2,2,2-trifluoroethylsulfonyl and 2,2,2-trichloroethylsulfonyl.

Halogenalkenylsulfonyl is for example 2- and 3-fluoropropenylsulfonyl, 2- and 3-chloropropenylsulfonyl, 2- and 3-bromopropenylsulfonyl, 2,3,3-trifluoropropenylsulfonyl, 2,3,3-trichloropropenylsulfonyl, 4,4,4-trifluorobut-2-en-1-yl-sulfonyl and 4,4,4-trichlorobut-2-en-1-yl-sulfonyl.

Cyanoalkyl is for example cyanomethyl, cyanoethyl, cyanoeth-1-yl and cyanopropyl.

Hydroxyalkyl is for example hydroxymethyl, 2-hydroxyethyl and 3-hydroxypropyl.

Alkylamino is for example methylamino, ethylamino and the isomeric propyl and butylamino.

Dialkylamino is for example dimethylamino, diethylamino and the isomeric dipropyl and dibutylamino.

Halogenalkylamino is for example chloroethylamino, trifluoroethylamino and 3-chloropropylamino.

Di(halogenalkyl)amino is for example di(2-chloroethyl)-amino.

Alkylcarbonyl is in particular acetyl and propionyl.

Halogenalkylcarbonyl is in particular trifluoroacetyl, trichloroacetyl, 3,3,3-trifluoropropionyl and 3,3,3-trichloropropionyl.

Alkenylcarbonyl is in particular vinylcarbonyl, allylcarbonyl, methallylcarbonyl, but-2-en-1-yl-carbonyl, pentenylcarbonyl and 2-hexenylcarbonyl.

Alkinylcarbonyl is in particular acetylenecarbonyl, propargylcarbonyl, 1-methylpropargylcarbonyl, 3-butinylcarbonyl, but-2-in-1-yl-carbonyl and pent-4-in-1-yl-carbonyl.

Alkoxy is for example methoxy, ethoxy, n-propoxy, isopropoxy, n-butoxy, isobutoxy, sec-butoxy and tert-butoxy; preferably methoxy, ethoxy and isopropoxy.

Alkenyloxy is for example allyloxy, methallyloxy and but-2-en-1-yloxy.

Alkinyloxy is for example propargyloxy and 1-methylpropargyloxy.

Alkoxyalkyl is for example methoxymethyl, methoxyethyl, ethoxymethyl, ethoxyethyl, n-propoxymethyl, n-propoxyethyl, isopropoxymethyl and isopropoxyethyl.

Alkenyloxy is for example allyloxyalkyl, methallyloxyalkyl and but-2-en-1-yloxyalkyl.

Alkoxycarbonyl is for example methoxycarbonyl, ethoxycarbonyl, n-propoxycarbonyl, isopropoxycarbonyl and n-butoxycarbonyl, preferably methoxycarbonyl and ethoxycarbonyl.

Alkenyloxycarbonyl is for example allyloxycarbonyl, methallyloxycarbonyl, but-2-en-1-yl-oxycarbonyl, pentenyloxycarbonyl and 2-hexenyloxycarbonyl.

Alkinyloxycarbonyl is for example propargyloxycarbonyl, 3-butinyloxycarbonyl, but-2-in-1-yl-oxycarbonyl and 2-methylbutin-2-yl-oxycarbonyl.

Alkoxyalkoxycarbonyl is for example methoxymethoxycarbonyl, ethoxymethoxycarbonyl, ethoxyethoxycarbonyl, propoxymethoxycarbonyl, propoxyethoxycarbonyl, propoxypropoxycarbonyl and butoxyethoxycarbonyl.

Halogenalkoxy is for example fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy.

The cycloalkyl radicals suitable as substituents are for example cyclopropyl, cyclobutyl, cyclopentyl and cyclohexyl.

The cycloalkoxycarbonyl radicals suitable as substituents are for example cyclopropoxycarbonyl, cyclobutoxycarbonyl, cyclopentoxycarbonyl and cyclohexyloxycarbonyl.

Alkylthio is for example methylthio, ethylthio, propylthio and butylthio, as well as the branched isomers thereof.

Alkylthioalkyl is for example methylthioethyl, ethylthioethyl, methylthiopropyl and ethylthiopropyl.

Halogenalkylthiocarbonyl is for example fluoromethylthiocarbonyl, difluoromethylthiocarbonyl, trifluoromethylthiocarbonyl, 2,2,2-trifluoroethylthiocarbonyl, 1,1,2,2-tetrafluoroethylthiocarbonyl, 2-fluoroethylthiocarbonyl, 2-chloroethylthiocarbonyl and 2,2,2-trichloroethylthiocarbonyl.

Corresponding meanings may also be ascribed to the substituents in the listed definitions, such as, for example, halogenalkenylcarbonyl, halogenalkinylcarbonyl, $R_{40}O—$, $R_4C(O)—$, $R_{11}X_3C(O)—$, $R_{13}X_4C(O)—$, $R_{14}X_5C(O)—$, $R_5X_1C(O)—$, $R_8X_2C(O)$-alkyl, $R_8X_2C(O)$-cycloalkyl, $R_{41}S(O)_{n2}—$,

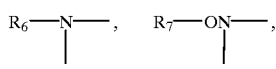

$R_{42}(R_{43})N—$, $R_{45}(R_{46})N—C(R_{44})=N—$, $B_1$alkyl, $B_1$alkenyl, $B_1$alkinyl, $B_1$halogenalkyl, $B_1$halogenalkenyl, $B_1$alkoxyalkyl, $B_1$alkylthioalkyl, $B_1$cycloalkyl and $B_2—C(R_{12})=CH—$.

In the definition of $R_5$, the groups

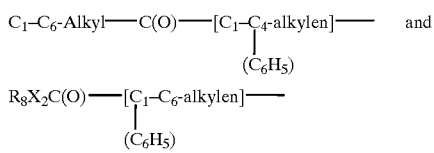

mean that the $C_1–C_6$alkyl-C(O)— or $C_1–C_6$alkylene chain is in addition substituted by phenyl ($C_6H_5$) on one of the 4 or 6 carbon atoms, wherein the phenyl ring is substituted once to three times by halogen, $C_1–C_4$alkyl or $C_1–C_4$halogenalkyl, and the alkylene chain may be straight-chained or branched and may, for example, be methylene, ethylene, methylethylene, propylene, 1-methylpropylene and butylene.

In the definitions cyanoalkyl, alkylcarbonyl, alkenylcarbonyl, halogenalkenylcarbonyl, alkinylcarbonyl, alkoxycarbonyl, alkoxycarbonylalkyl and halogenalkylcarbonyl, the cyano- and carbonyl carbon atoms are not included in the upper and lower limits of the carbon number.

L in the reagents of formulae XII, XXI, XXIVa, XXIVb and XXXV is a leaving group, such as halogen, for example, preferably chlorine, bromine or iodine, $C_1–C_3$alkyl- or arylsulfonyloxy, preferably $CH_3SO_2O—$ or

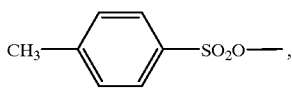

or $C_1–C_6$alkylcarbonyloxy, preferably acetyloxy.

$L_1$ in the reagent of formula XIII is a leaving group such as, for example, $HOS(O)_2O—$,

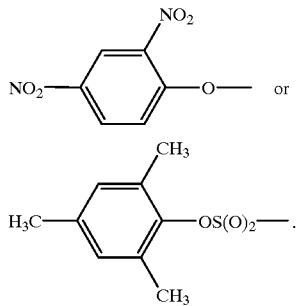

$L_2$ in the reagents of formulae XXVa and XXVc is a leaving group such as, for example, hydroxy, $C_1–C_4$alkoxy or halogen, preferably chlorine, bromine or iodine.

$L_3$ in the reagent of formula XXXI is a leaving group such as chlorine or bromine, trichloromethoxy or

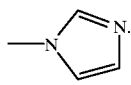

L$_4$ in the compounds of formulae II and III (reaction schemes 1 and 2) is a leaving group such as, for example, halogen, typically fluorine, chlorine or bromine or C$_1$–C$_4$alkyl- or phenylsulfonyl or C$_1$–C$_4$alkyl-, C$_1$–C$_4$halogenalkyl- or phenylsulfonyloxy.

R$_{33}$ together with R$_{32}$ (group W$_7$) forms a C$_3$–C$_5$alkylene bridge which may be broken for example by oxygen and substituted by =O, and is illustrated by way of example in Tables 127 (compound of formula I$_{127}$), 130 (compound of formula I$_{130}$), 136 (compound of formula I$_{136}$) and 137 (compound of formula I$_{137}$).

The invention relates also to the salts which the compounds of formula I with acidic hydrogen, especially the derivatives with carboxylic acid groups (for example, carboxyl-substituted alkyl, alkylene, alkenyl, alkinyl, alkoxyalkyl, alkylthioalkyl and cycloalkyl groups) may form with bases. These salts are, for example, alkali metal salts, such as sodium and potassium salts; earth alkali metal salts, such as calcium and magnesium salts; ammonium salts, i.e. unsubstituted ammonium salts and monosubstituted or polysubstituted ammonium salts, such as triethylammonium and methylammonium salts; or salts with other organic bases.

Salt-forming alkali metal and alkaline earth metal bases include the hydroxides of lithium, sodium, potassium, magnesium or calcium, those of sodium and potassium being especially preferred. Suitable salt-forming substances are described for example in WO 97/41112. Examples of amines suitable for forming ammonium salts are ammonia, as well as primary, secondary, and tertiary C$_1$–C$_{18}$alkylamines, C$_1$–C$_4$hydroxyalkylamines and C$_2$–C$_4$alkoxyalkylamines, typically methylamine, ethylamine, n-propylamine, isopropylamine, the four isomeric butylamines, n-amylamine, isoamylamine, hexylamine, heptylamine, octylamine, nonylamine, decylamine, pentadecylamine, hexadecylamine, heptadecylamine, octadecylamine, methyl ethylamine, methyl isopropylamine, methyl hexylamine, methyl nonylamine, methyl pentadecylamine, methyl octadecylamine, ethyl butylamine, ethyl heptylamine, ethyl octylamine, hexyl heptylamine, hexyl octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines such as pyridine, quinoline, isoquinoline, morpholine, thiomorpholine, piperidine, pyrrolidine, indoline, quinuclidine and azepine; primary arylamines such as anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

The salts of compounds of formula I with basic groups, especially with basic pyridyl and pyrazolyl rings (W3 and W4), or of derivatives with amino groups, e.g. amino, alkylamino and dialkylamino groups in the definition of R$_2$, W$_1$ or W$_3$ (R$_{15}$, R$_{21}$, R$_{22}$) are, for example, salts with inorganic and organic acids, for example hydrogen halides, such as hydrofluoric acid, hydrochloric acid, hydrobromic acid or hydriodic acid, as well as sulfuric acid, phosphoric acid, nitric acid and organic acids, such as acetic acid, trifluoracetic acid, trichloroacetic acid, propionic acid, hydroxyethanoic acid, thiocyanic acid, citric acid, benzoic acid, oxalic acid, formic acid, benzenesulfonic acid, p-toluenesulfonic acid and methanesulfonic acid.

The presence of at least one asymmetric carbon atom in the compounds of formula I, for example in substituent R$_3$=R$_5$X$_1$C(O)—, wherein R$_5$ is a branched alkyl, alkenyl, halogenalkyl or alkoxyalkyl group, or R$_3$=B$_1$—C$_3$–C$_6$cycloalkyl, wherein for example B$_1$ is C$_1$–C$_8$alkoxy or R$_{11}$X$_3$C(O)—, means that the compounds may occur both in single optically active isomers and also in the form of racemic mixtures. In the present invention, the active substances of formula I are understood to include both the pure enantiomers and the racemates or diastereomers.

If an aliphatic C=C double bond is present (e.g. in substituent R$_3$=B$_2$—C(R$_{12}$)=CH—), then geometric isomerism may occur. The present invention also relates to these isomers.

Compounds of formula I are preferred wherein R$_2$ is methyl, halogen, hydroxy, nitro, amino or cyano.

Also preferred are compounds of formula I wherein W is the group

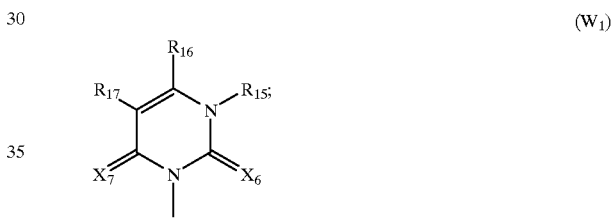

(W$_1$)

and R$_{15}$, R$_{16}$, R$_{17}$, X$_6$ and X$_7$ are as defined under formula I.

Especially preferred are those compounds wherein R$_{15}$ is methyl; R$_{16}$ is trifluoromethyl; R$_{17}$ is hydrogen; and X$_6$ and X$_7$ are oxygen.

Likewise preferred are compounds of formula I wherein R$_1$ is fluorine or chlorine; R$_2$ is chlorine, bromine or cyano; and R$_3$ is R$_5$X$_1$C(O)—, wherein R$_5$ has the meaning defined under formula I; and X$_1$ is oxygen or sulfur. Of these compounds, those wherein R$_2$ is chlorine are especially important.

The method described in the invention for the preparation of compounds of formula I,

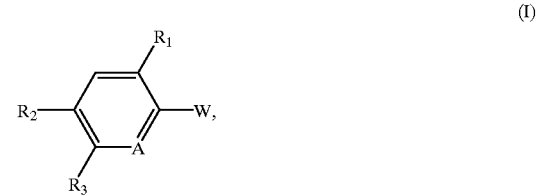

(I)

wherein R$_1$, R$_2$, R$_3$, A and W are as defined under formula I, is carried out by analogy with known methods, such as those described for example in WO 97/00246, WO 96/01254 and International Patent Application Number PCT/EP 97/06243, and comprises treating a compound of formula II

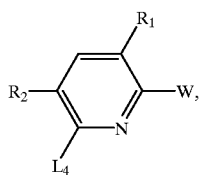
(II)

wherein $R_1$, $R_2$ and W have the meanings indicated, and $L_4$ is a leaving group such as halogen, either a) in a suitable solvent, where appropriate in the presence of a base such as a trialkylamine, a palladium or nickel catalyst and a compound of formula V

(V), wherein $R_5$ is hydrogen or $C_1$–$C_4$alkyl, in an autoclave under positive pressure with carbon monoxide, or b) in a suitable solvent in the presence of a tertiary amine, a palladium catalyst, and an olefin by means of the Heck reaction, or under said conditions by means of reaction with a Grignard reagent of formula Va

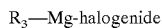
(Va), wherein $R_3$ is $B_1$—$C_1$–$C_8$alkyl, $B_1$—$C_2$–$C_8$alkenyl, $B_1$—$C_2$–$C_8$alkinyl, $B_1$—$C_1$–$C_8$halogenalkyl, $B_1$—$C_2$–$C_8$halogenalkenyl, $B_1$—$C_1$–$C_4$alkoxy-$C_1$–$C_4$alkyl, $B_1$—$C_1$–$C_4$alkylthio-$C_1$–$C_4$alkyl or $B_1$—$C_{13}$–$C_6$cycloalkyl and $B_1$ is as defined under formula I, or in an inert solvent and in the presence of a catalyst, such as palladium-bis-triphenylphosphine dichloride ($Pd(C_6H_5)_2Cl_2$), in a manner analogous to that described in Synlett 1998, 1185, with a tin compound of formula Vb

(Vb), wherein $R_3$ has the meaning indicated, or c) where applicable in an inert solvent at reaction temperatures of 20–300° C. subjecting it to a cyanidation reaction, e.g. with an alkali metal cyanide or a cyanide whose metal ion belongs to the first or second subgroup of the periodic system, such as copper cyanide, in a manner analogous to that described in J. Het. Chem. 11, 397 (1974), or d) first oxidizing it in a suitable solvent to form a compound of formula IV

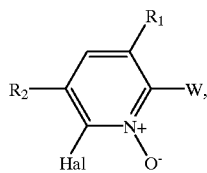
(IV)

and treating this in an inert solvent with dimethylcarbamoyl chloride and a cyanidation reagent, and then where applicable further functionalizing it according to the definitions of A and $R_3$.

The method described in the invention for the preparation of compounds of formula I,

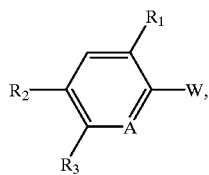
(I)

wherein $R_1$, $R_2$, $R_3$ and A are as defined under formula I, W is a $W_1$ group

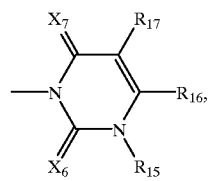
($W_1$)

and $R_{15}$, $R_{16}$, $R_{17}$, $X_6$ and $X_7$ are as defined under formula I, corresponding to a compound of formula Ia in reaction scheme 2, is carried out by analogy with the known methods such as those described for example in EP-A-0 438 209 or DE-OS-19 604 229, and comprises reacting a compound of formula III

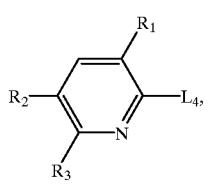
(III)

wherein $R_1$, $R_2$ and $R_3$ have the meanings indicated, and $L_4$ is a leaving group, such as halogen, for example fluorine, chlorine or bromine, in the presence of an inert solvent and ammonia if necessary in an autoclave at temperatures of −10 to 180° C. to form a compound of formula VI

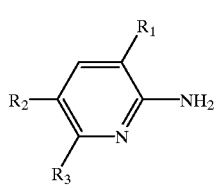
(VI)

reacting this in the presence of a base and a solvent a) with a chloroformate of formula VII

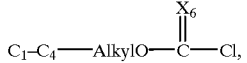
(VII)

wherein $X_6$ is as defined under formula I, to form a compound of formula VIII

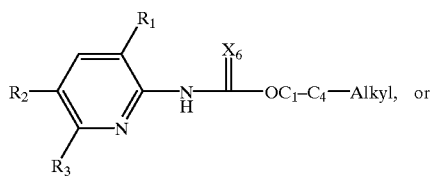
(VIII)

b) with oxalyl chloride, phosgene or thiophosgene to form a compound of formula IX

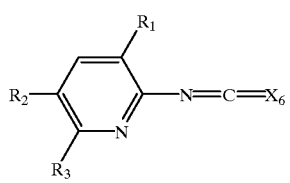
(IX)

followed by cyclization of a compound of formula VIII or IX in the presence of 0.1–1.5 equivalents of a base in an inert solvent with an enamine dervivative of formula X

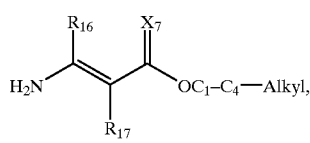
(X)

wherein $R_{16}$ and $R_{17}$ are as defined under formula I, and $X_7$ is oxygen, and a resulting compound of formula XI

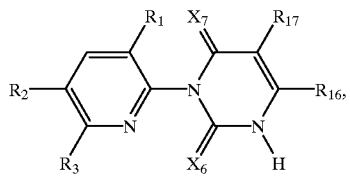
(XI)

wherein $R_1$, $R_2$, $R_3$, $R_{16}$, $R_{17}$, $X_6$ and $X_7$ have the meanings indicated, and further reacting this compound in the presence of an inert solvent and a base with c) a compound of formula XII

—L    (XII), wherein $R_{15}$ is $C_1$–$C_3$alkyl or $C_1$–$C_3$halogenalkyl, and L is a leaving group, or d) with a hydroxylamine derivative of formula XIII $NH_2$—$L_1$    (XIII), wherein $L_1$ is a leaving group, and subsequently performing if necessary oxidation

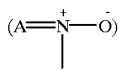

and thionization.

The method described in the invention for the preparation of compounds of formula I,

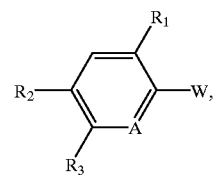
(I)

wherein $R_1$, $R_2$, $R_3$, and A are as defined under formula I, W is a $W_2$ group

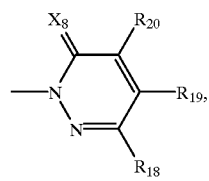
($W_2$)

and $R_{18}$, $R_{19}$, $R_{20}$, and $X_8$ are as defined under formula I, corresponding to a compound of formula Ib in reaction scheme 3, is carried out by analogy with known methods, such as those described for example in DE-A-4 423 934 and JP-A-58 213 776, and comprises either a) reacting a compound of formula III,

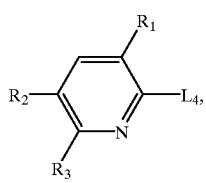
(III)

wherein $R_1$, $R_2$ and $R_3$ have the meanings indicated, and $L_4$ is a leaving group such as halogen, for example fluorine, chlorine or bromine, with hydrazine, preferably in an amphiprotic solvent, to form a compound of formula XIV

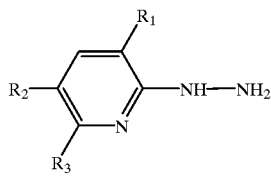
(XIV)

further reacting this with a compound of formula XV or XVa

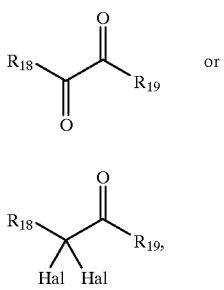 (XV)

or

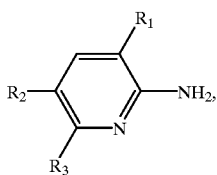 (XVa)

wherein $R_{18}$ and $R_{19}$ have the meanings defined under formula I, and Hal in a compound of formula XVa is chlorine or bromine, or b) first diazotizing a compound of formula VI,

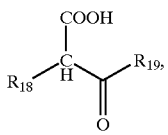 (VI)

wherein $R_1$, $R_2$ and $R_3$ have the meanings indicated, then further reacting it with a compound of formula XVI

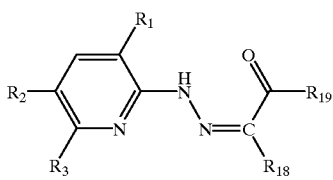 (XVI)

wherein $R_{18}$ and $R_{19}$ have the meanings indicated, and obtaining a compound of formula XVII

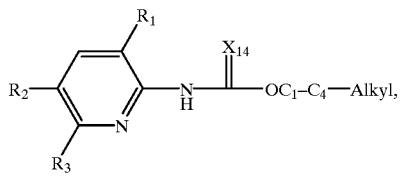 (XVII)

which if necessary is cyclized in the presence of a base, such as 4-dimethylaminopyridine and a compound of formula XVIII

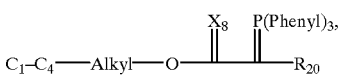 (XVIII)

wherein $R_{20}$ has the meaning indicated, and $X_8$ is oxygen, and subsequently performing if necessary oxidation

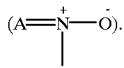

The method described in the invention for the preparation of compounds of formula I,

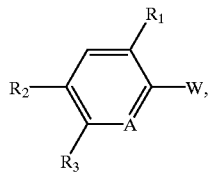 (I)

wherein $R_1$, $R_2$, $R_3$ and A are as defined under formula I, W is a $W_7$ group

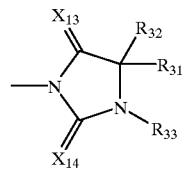

($W_7$), and $R_{31}$, $R_{32}$, $R_{33}$, and $X_8$ are as defined under formula I, corresponding to a compound of formula Ig in reaction scheme 4, is carried out by analogy with known methods, such as those described for example in EP-A-0 272 594, EP-A-0 493 323, DE-A-3 643 748, WO 95/23509, U.S. Pat. Nos. 5,665,681 and 5,661,109, and comprises for example either a) reacting a compound of formula VIIIa

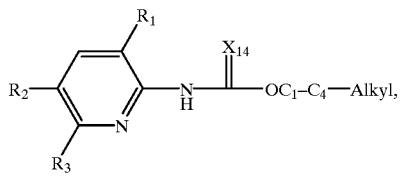 (VIIIa)

in the presence of a solvent and a base, or b) a compound of formula IXa

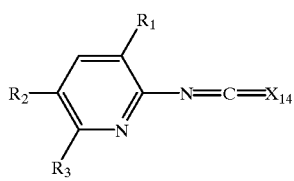 (IXa)

if necessary in a suitable solvent, wherein the radicals $R_1$, $R_2$, $R_3$ and $X_{14}$ in compounds of formula VIIIa and IXa have the meanings indicated, with a compound of formula XIX

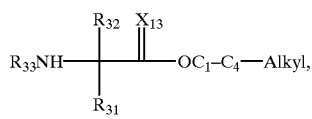

(XIX)

wherein $R_{31}$, $R_{32}$, $R_{33}$ and $X_{13}$ have the meanings indicated, and obtaining a compound of formula XX

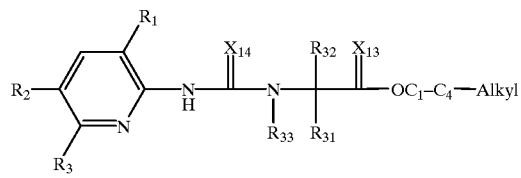

(XX)

cyclizing this in the presence of a suitable solvent and a base and then where applicable c) if $R_{33}$ is hydrogen, reacting it with a compound of formula XXI $R_{33}$—L  (XXI), wherein $R_{33}$ is $C_1$–$C_3$alkyl, and L is a leaving group, and subsequently performing if necessary oxidation

and thionization.

The method described in the invention for the preparation of compounds of formula I,

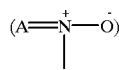

(I)

wherein $R_1$, $R_2$, $R_3$ and A are as defined under formula I, W is a $W_8$ group

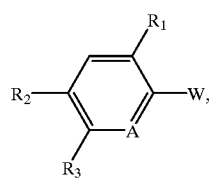

($W_8$), and $R_{34}$, $R_{35}$, $X_{15}$, and $X_{16}$ are as defined under formula I, corresponding to a compound of formula Ih in reaction scheme 5, is carried out by analogy with known methods, such as those described for example in EP-A-0 210 137, DE-A-2 526 358, EP-A-0 075 267 and EP-A-0 370 955, and comprises a) reacting a compound of formula VIIIb

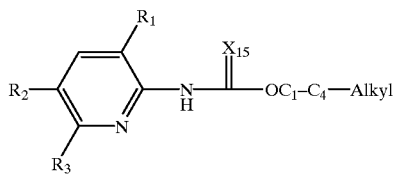

(VIIIb)

in the presence of a solvent and a base, or b) a compound of formula IXb

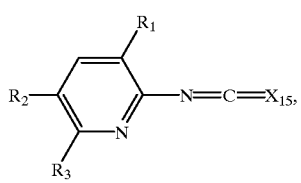

(IXb)

wherein the radicals $R_1$, $R_2$, $R_3$ and $X_{15}$ in compounds of formula VIIIb and IXb have the meanings indicated, if necessary in a suitable solvent, with a compound of formula XXII

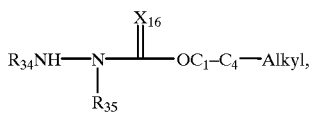

(XXII)

wherein $R_{34}$, $R_{35}$, and $X_{16}$ have the meanings indicated, and obtaining a compound of formula XXIII

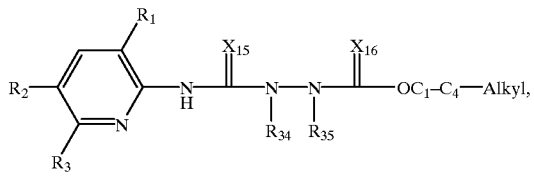

(XXIII)

cyclizing this in the presence of a suitable solvent and a base and then where applicable c) if $R_{34}$ and/or $R_{35}$ are/is hydrogen, further reacting it with a compound of formula XXIVa or XXIVb $R_{34}$—L  (XXIVa)

or $R_{35}$—L  (XXIVb), wherein $R_{34}$ and $R_{35}$ are independently $C_1$–$C_3$alkyl, and L is a leaving group, or with a Michael acceptor, and then if necessary oxidizing

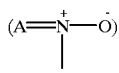

and thionizing it.

The method described in the invention for the preparation of compounds of formula I,

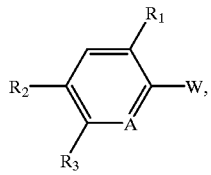

(I)

wherein $R_1$, $R_2$, $R_3$ and A are as defined under formula I, W is a $W_3$ group

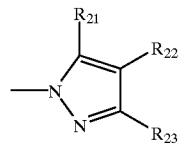

($W_3$), and $R_{21}$, $R_{22}$, and $R_{23}$ are as defined under formula I, corresponding to a compound of formula Ic in reaction scheme 6, is carried out by analogy with known methods, such as those described for example in WO 97/07114, U.S. Pat. No. 5,306,694, DE-A-3 832 348, EP-A-0 257 479 and EP-A-0 500 209, and comprises condensing a compound of formula XIV

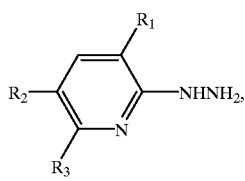

(XIV)

wherein $R_1$, $R_2$ and $R_3$ have the meanings indicated, for example a) with a compound of formula XXV

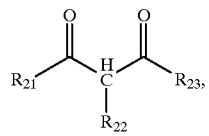

(XXV)

wherein $R_{21}$ is hydrogen, $C_1$–$C_3$alkyl or $C_1$–$C_3$halogenalkyl; $R_{22}$ is hydrogen, $C_1$–$C_4$alkyl, $C_1$–$C_4$halogenalkyl, $C_2$–$C_4$alkenyl, $C_3$–$C_5$halogenalkenyl or $C_3$- or $C_4$alkinyl; and $R_{23}$ hydrogen, $C_1$–$C_4$alkyl or $C_1$–$C_4$halogenalkyl, if necessary in the presence of an acidic, basic or bifunctional catalyst such as p-toluenesulfonic acid, for example, or b) with a compound of formula XXVa

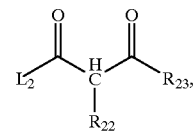

(XXVa)

wherein $R_{22}$ and $R_{23}$ have the meanings indicated, and $L_2$ is a suitable leaving group, to form a compound of formula XXVI

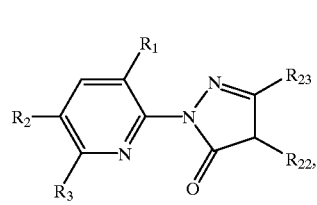

(XXVI)

and further functionalizing the pyrazolone group in accordance with the definition of $R_{21}$ in a manner analogous to known methods, for example using a halogenation agent such as phosphorus oxychloride, to form the corresponding halogen derivative of formula Ic

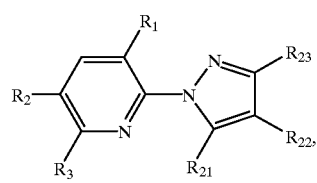

(Ic)

wherein $R_1$, $R_2$, $R_3$, $R_{22}$ and $R_{23}$ have the meanings indicated, and $R_{21}$ is halogen, and subsequently performing if necessary oxidation

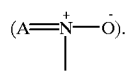

The method described in the invention for the preparation of compounds of formula I,

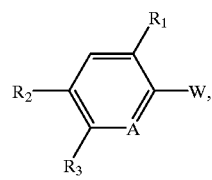

(I)

wherein $R_1$, $R_2$ $R_3$ and A are as defined under formula I, W is a $W_4$ group

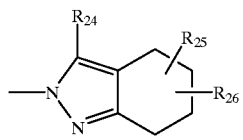

and $R_{24}$, $R_{25}$, $R_{26}$ are as defined under formula I, corresponding to formula Id in reaction scheme 7, is carried out by analogy with known methods such as those described for example in EP-A-0 370 332, EP-A-0 370 955 or DE-A-3 917 469, and comprises condensing a compound of formula XIV (XIV)

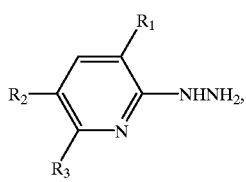

wherein $R_1$, $R_2$ and $R_3$ have the meanings indicated,
a) with a compound of formula XXVb (XXVb)

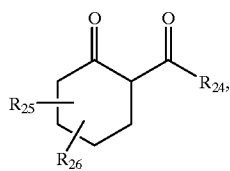

wherein $R_{25}$ and $R_{26}$ have the meanings indicated, and $R_{24}$ is hydrogen, $C_1$–$C_4$alkyl or $C_1$–$C_4$halogenalkyl, if necessary in the presence of a catalyst, or
b) with a compound of formula XXVc (XXVc)

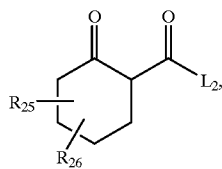

wherein $R_{25}$ and $R_{26}$ have the meanings indicated, and $L_2$ is a suitable leaving group, to form a compound of formula XXVIa (XXVIa)

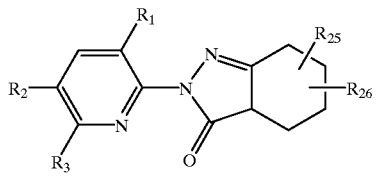

and treating this compound with a halogenation agent, such as phosphoroxy halogenide or thionyl halogenide, and obtaining a compound of formula Id (Id)

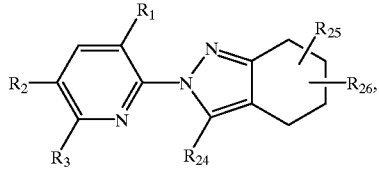

wherein $R_1$, $R_2$, $R_3$, $R_{25}$ and $R_{26}$ have the meanings indicated and $R_{24}$ is halogen, and reacting this compound if necessary with a cyanide of formula XXVII $$M(CN)_s \qquad (XXVII),$$

wherein M is an ammonium cation, alkali metal ion or metal ion of the first or second subgroup of the periodic system, and s is the number 1 or 2, where applicable in the presence of an alkali metal iodide ($R_{24}$=cyano; reaction scheme 7), and subsequently performing if necessary oxidation

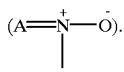

The method described in the invention for the preparation of compounds of formula I, (I)

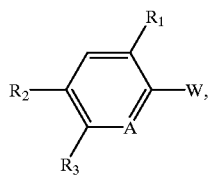

wherein $R_1$, $R_2$, $R_3$ and A are as defined under formula I, W is a $W_5$ ($W_5$)

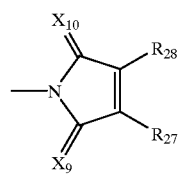

or $W_6$ ($W_6$)

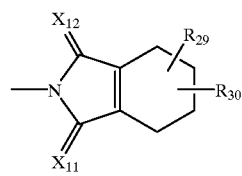

group, and $R_{27}$, $R_{28}$, $R_{29}$, $R_{30}$, and $X_9$ to $X_{12}$ are as defined under formula I, corresponding to compounds of formula Ie and If in reaction scheme 8, is carried out by analogy with known methods, such as those described for example in DE-A-3 917 469, WO 92/00976, U.S. Pat. No. 5,069,711 and EP-A-0 260 228, and comprises for example a) reacting a compound of formula XXVIII

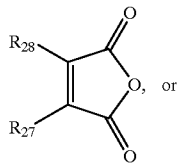

(XXVIII)

b) a compound of formula XXVIIIa

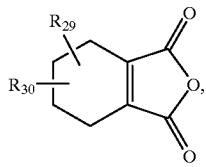

(XXVIIIa)

wherein radicals $R_{27}$ to $R_{30}$ in compounds of formulae XXVIII and XXVIIIa have the meanings indicated, with a compound of formulae VI

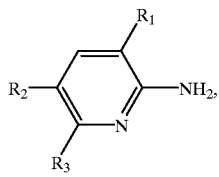

(IV)

wherein $R_1$, $R_2$ and $R_3$ have the meanings indicated, in an inert solvent in the presence of a $C_1$–$C_4$alkylcarboxylic acid at temperatures of 20° to 200° C. and reacting the resulting compounds of formulae Ie and If

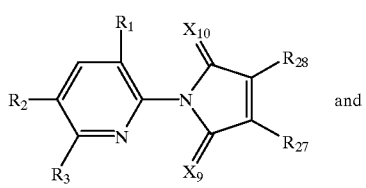

(Ie)

and

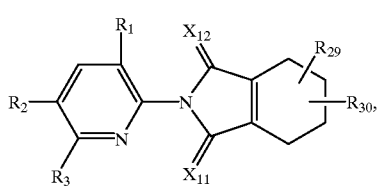

(If)

wherein $R_1$ to $R_3$ and $R_{27}$ to $R_{30}$ have the meanings indicated, and $X_9$ to $X_{12}$ are oxygen, if necessary with the aid of a suitable sulfur reagent to form the corresponding thiono compound of formulae Ie and If, wherein $X_9$ and/or $X_{10}$, $X_{11}$, $X_{12}$, are sulfur, and oxidizing the said compound

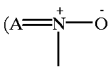

reaction scheme 8).

The method described in the invention for the preparation of compounds of formula I

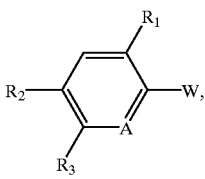

(I)

wherein $R_1$, $R_2$, $R_3$, and A are as defined under formula I, W is a $W_9$ group

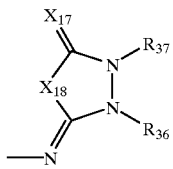

and $R_{36}$, $R_{37}$, $X_{17}$, and $X_{18}$ are as defined under formula I, corresponding to a compound of formula Ii in reaction scheme 9, is carried out by analogy with known methods, such as those described for example in WO 95/00521, EP-A-0 611 708 and WO 94/25467, and comprises for example reacting a) a compound of formula VIIIc

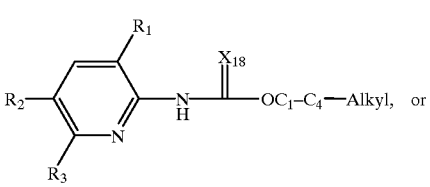

(VIIIc)

b) a compound of formula IXc

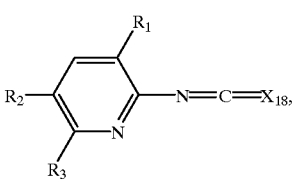

(IXc)

wherein the radicals $R_1$, $R_2$, $R_3$ and $X_{18}$ in compounds of formulae VIIIc and IXc have the meanings indicated, if necessary in the presence of a suitable solvent and a base, with a compound of formula XXIX

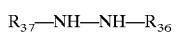   (XXIX), wherein $R_{36}$ and $R_{37}$ are as defined under formula I, and obtaining a compound of formula XXX a) reacting a compound of formula XIV

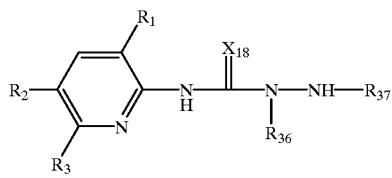
(XXX)

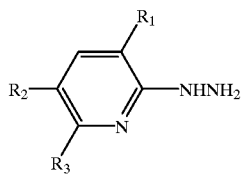
(XIV)

and subsequently reacting this, if necessary in a solvent and in the presence of a base, with a (thio-)carbonylation reagent of formula XXXI if necessary in the presence of a catalyst, with a compound of formula XXXII

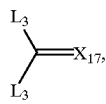
(XXXI)

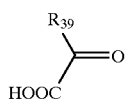
(XXXII)

wherein $X_{17}$ has the meaning indicated, and $L_3$ is a leaving group (reaction scheme 9), and subsequently performing if necessary oxidization to form a compound of formula XXXIII

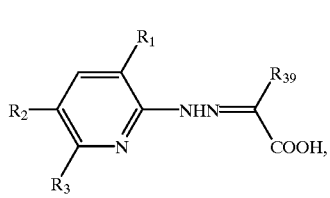
(XXXIII)

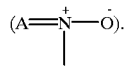

The method described in the invention for the preparation of compounds of formula I wherein the radicals $R_1$, $R_2$, $R_3$ and $R_{39}$ in the compounds of formulae XIV, XXXII and XXXIII have the meanings indicated, and further cyclizing this compound with an azide of formula XXXIV

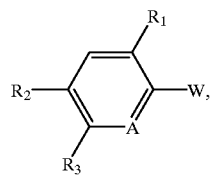
(I)

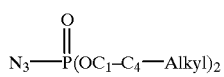
(XXXIV)

($X_{19}$=O, $R_{38}$=H), or b) cyclizing a compound of formula XIV

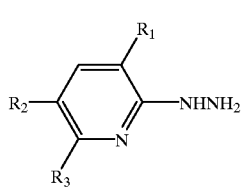
(XIV)

wherein $R_1$, $R_2$, $R_3$ and A are as defined under formula I, W is a $W_{10}$ group

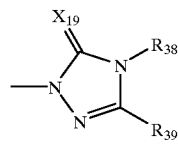

with a compound of formula XXXVI

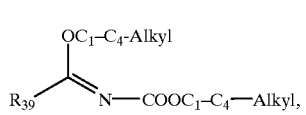
(XXXVI)

and $R_{38}$ $R_{39}$, and $X_9$ are as defined under formula I, corresponding to a compound of formula Ik in reaction scheme 10, is carried out by analogy with known methods, such as those described for example in U.S. Pat. No. 5,980,480, DE-A-3 917 469, U.S. Pat. No. 4,818,275, 5,041,155 und EP-A-0 610 733, and comprises, for example, wherein the radicals $R_1$, $R_2$, $R_3$ and $R_{39}$ in the compounds of formulae XIV and XXXVI have the meanings indicated, ($X_{19}$=O, $R_{38}$=H), or c) cyclizing a compound of formula XIV

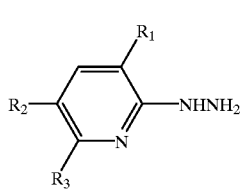 (XIV)

first with a compound of formula XXXVII $R_{39}-CHO$  (XXXVII)

to form a compound of XXXIIIa

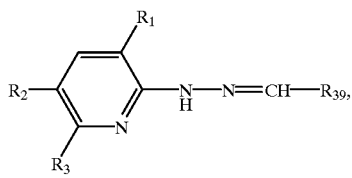 (XXXIIIa)

then with an alkali metal cyanate to form a compound of XXXVIII

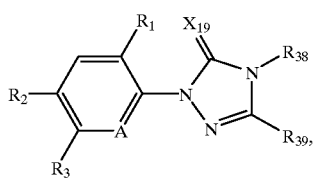 (XXXVIII)

and finally cyclizing this compound in the presence of an oxidation agent and obtaining a compound of formula Ik (Ik)

wherein $R_1$, $R_2$, $R_3$ and $R_{39}$ have the meanings indicated, $X_{19}$ is oxygen, and $R_{38}$ is hydrogen, and treating this compound if necessary with a sulfur reagent ($X_{19}=S$) and in the presence of a base with an alkylation reagent of formula XXXV $R_{38}-L$  (XXXV), wherein $R_{38}$ is $C_1-C_4$alkyl, $C_1-C_4$halogenalkyl, $C_3$- or $C_4$alkenyl, $C_3$- or $C_4$halogenalkenyl or $C_3$- or $C_4$alkinyl, and L is a leaving group, and subsequently performing if necessary oxidization

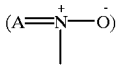

and thionization.

The method described in the invention for the preparation of compounds of formula I is carried out in a manner analogous to known methods and comprises, for example, reacting a compound of formula III (III)

wherein $R_1$, $R_2$ and $R_3$ are as defined under formula I, and $L_4$ is a leaving group, such as halogen, for example fluorine, chlorine or bromine, with a compound of $W_{01}$, $W_{02}$, $W_{03}$, $W_{04}$, $W_{05}$, $W_{06}$, $W_{07}$, $W_{08}$, $W_{09}$ or $W_{010}$ ($W_{01}$)

($W_{02}$)

($W_{03}$)

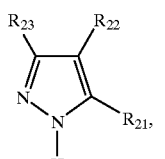 ($W_{04}$)

-continued

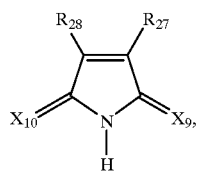
(W05)

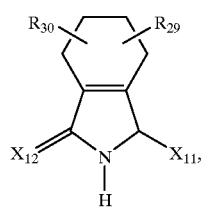
(W06)

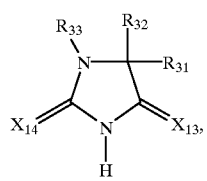
(W07)

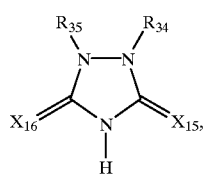
(W08)

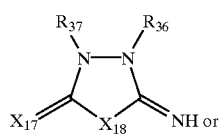
(W09)

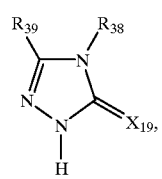
(W010)

wherein $R_{15}$ to $R_{39}$ and $X_6$ to $X_{19}$ are as defined under formula I, if necessary in the presence of a suitable solvent and base, and if necessary subjecting the obtainable compounds of formula I (A=N—) to oxidation

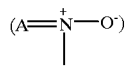
($A=\overset{+}{N}-O^-$)

and thionization.

The method described in the invention for the preparation of compounds of formula II

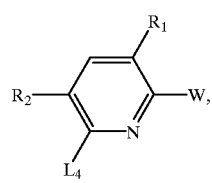
(II)

wherein $R_1$ and $R_2$ are as defined under formula I, W is a

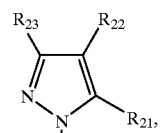
(W3)

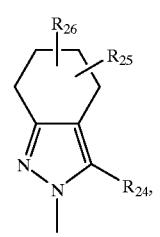
(W4)

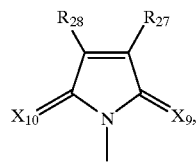
(W5)

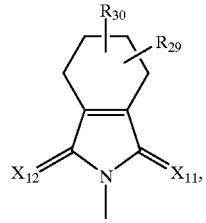
(W6)

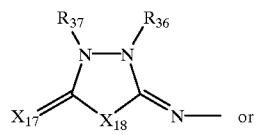
(W9)

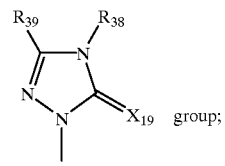
(W10)

group; $R_{21}$ to $R_{30}$, $R_{36}$ to $R_{39}$, $X_9$ to $X_{12}$ and $X_{17}$ to $X_{19}$ are as defined under formula I, and $L_4$ is a leaving group, such as halogen for example, especially chlorine or bromine, is carried out in a manner analogous to known methods and comprises, for example, first oxidizing a compound of formula XXXIX

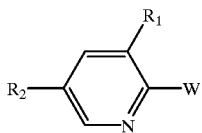

(XXXIX)

in a suitable solvent to form a compound of formula XXXX

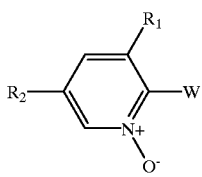

(XXXX)

wherein radicals $R_1$, $R_2$ and W in the compounds of formulae XXXIX and XXXX have the meanings indicated, and then subjecting the compound either to a) halogenation, for example with phosphorus oxychloride, if necessary in the presence of a base and a suitable solvent, or b) transformation in an inert solvent in the presence of an anhydride or antimony pentachloride, and following aqueous treatment, to form a compound of XXXXI

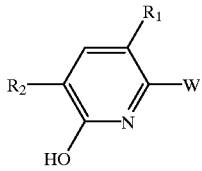

(XXXXI)

(so-called Katada reaction), and the halogenation of this compound if necessary in the presence of a base and a suitable solvent as described under variant a).

The above methods of preparation are explained in more detail in the following reaction schemes 1 to 12.

The preparation of a compound of formula I

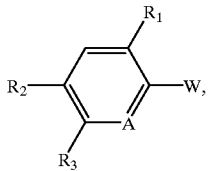

(I)

wherein $R_1$ to $R_3$, A and W are as defined under formula I, is explained in the following reaction scheme 1:

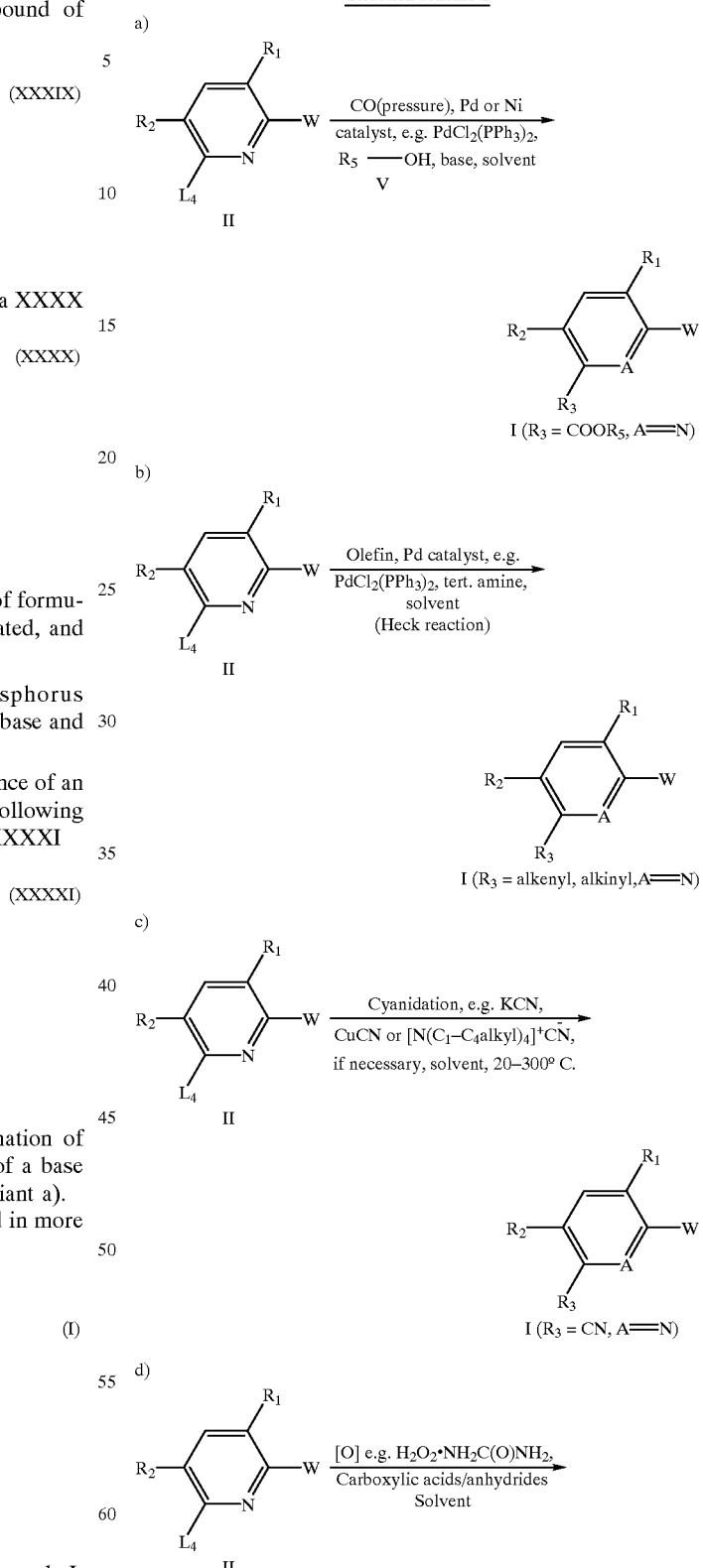

-continued

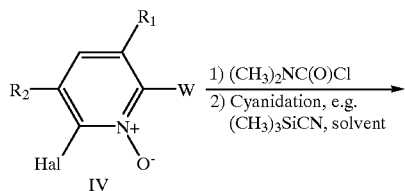

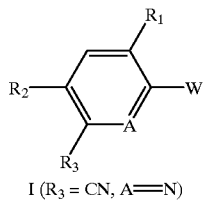

I ($R_3$ = CN, A≡N)

The pyridine derivatives of formula I, wherein $R_3$ is a HOOC— or $R_5$OOC group, may be prepared according to variant a) in reaction scheme 1 in a manner analogous to known methods, a useful method being to react for example the 6-halogen pyridine ($L_4$=halogen) of formula II in the presence of a palladium or nickel catalyst, such as a palladium triphenylphosphine complex ($PdCl_2(PPh_3)_2$), with carbon monoxide under pressure in an autoclave, if necessary in the presence of an alcohol of formula V $$R_5\text{—OH} \quad (V)$$

and a base, such as a trialkylamine, for example triethylamine.

According to variant b) in reaction scheme 1, pyridine derivatives of formula I, wherein $R_3$ is a $B_1$—$C_2$–$C_8$alkenyl, $B_1$—$C_2$–$C_8$alkinyl or $B_2$—$C(R_{12})$=CH group, are obtainable in a manner analogous to known methods, such as those described in "Transition Metals in Organic Synthesis", Editor S. Gibson, Oxford Press, 1997, for example starting from a 6-halogen pyridine of formula II ($L_4$=halogen) under the conditions of the Heck reaction with an olefin in the presence of a palladium catalyst, such as palladium(II) acetate ($Pd(CH_3COO)_2$), a tertiary amine, such as triethylamine, and a solvent.

According to variant c) in reaction scheme 1, pyridine derivatives of formula I, wherein $R_3$ is a cyano group, are obtainable for example directly by reacting for example the 6-halogen pyridine of formula II ($L_4$=halogen) with a cyanidation reagent such as an alkali metal cyanide, for example potassium or sodium cyanide, a transition metal cyanide, for example copper cyanide, a tetraalkylammonium cyanide or trialkylsilyl cyanide, for example trimethylsilyl cyanide, in an inert solvent.

According to variant d) in reaction scheme 1, a reactivation for example of the 6-halogen pyridine of formula II ($L_4$=halogen) first takes place via oxidation to form the corresponding pyridine-N-oxide of formula IV and the reaction thereof with dimethylcarbamoyl chloride to form the reactive 1-carbamoyloxypyridinium salt. The following reaction of this pyridinium salt with a cyanidation reagen is carried out in a manner analogous to that described under c). Such cyanidation reactions are described for example in Heterocycles 22,1121 (1984), J.Org.Chem. 48, 1375 (1983) and U.S. Pat. No. 4,776,219.

Further derivatization of the pyridine derivatives of formula I, primarily obtainable according to variants a) to d) in reaction scheme 1, wherein $R_3$ is a carboxyl, alkoxycarbonyl, alkenyl or alkinyl, or cyano group, and A is nitrogen, can be readily accomplished, taking into account the chemical reactivities of the pyridyl and W parts (groups $W_1$ to $W_{10}$), in a manner analogous to known standard methods, such as esterification, transesterification, hydrolysis, oxidative or reductive processes, or condensation reactions, for example the Wittig-Horner reaction. Such standard methods are described for example in WO 93/06090, EP-A-0 240 659 and in Houben-Weyl, "Methoden der Organischen Chemie", Vol. E1, Thieme Verlag Stuttgart, 1982.

The preparation of a compound of formula Ia

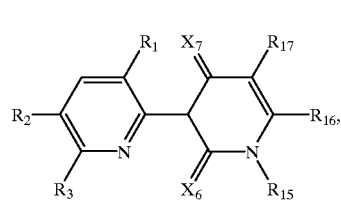

(Ia)

wherein $R_1$, $R_2$, $R_3$, $R_{15}$, $R_{16}$, $R_{17}$, $X_6$ and $X_7$ are as defined under formula I, is explained in the following reaction scheme 2.

Reaction scheme 2

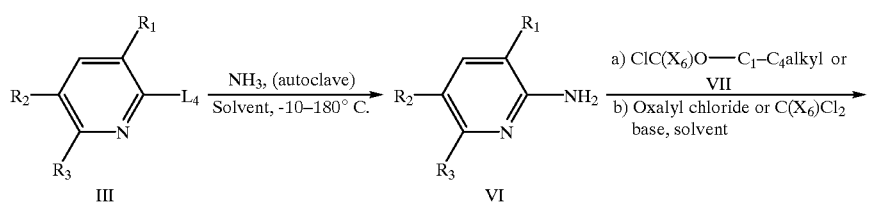

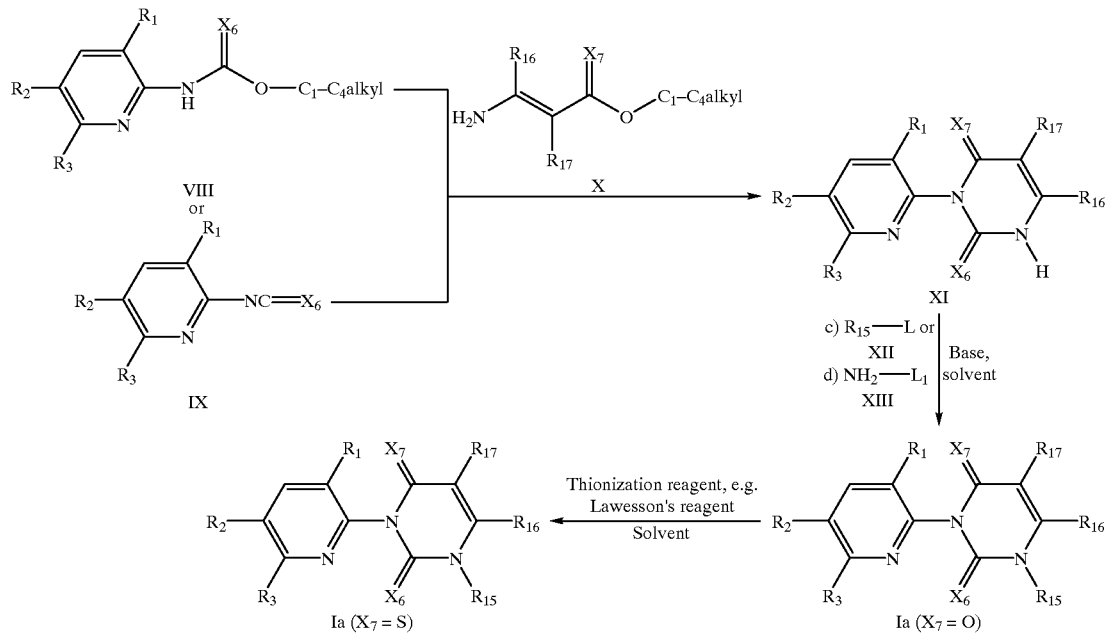

For the preparation of the compounds of formula Ia according to the invention, many known standard methods are available, such as those described for example in EP-A-0 438 209 and DE-OS-19 604 229 ($R_{16}$=Cyano). In reaction scheme 2, a selection of suitable preparative processes is shown, wherein the choice of reaction pathways and reagents depends on the reactivities of the substituents in the intermediate stages.

Starting for example from a compound of formula III, the aminopyridine of formula VI can be obtained by reacting with ammonia in an inert solvent, if necessary in an autoclave at temperatures from −10 to 180° C. This aminopyridine can be reacted in the presence of a base and a solvent either

- a) with a chloroformate of formula VII ($X_6$=O or S) to form a pyridyl carbamate of formula VIII, or
- b) with oxalyl chloride, phosgene ($X_6$=O) or thiophosgene ($X_6$=S) to form an iso(thio)cyanate of formula IX. Such reactions are described for example in Angew. 1971, 407.

The carbamate and iso(thio)cyanate of formulae VIII and IX can be cyclized in the presence of the enamine derivative of formula X in an inert solvent to form the uracil derivative of formula XI, the reaction of the iso(thio)cyanate of formula IX being advantageously carried out in the presence of 0.1–1.5 equivalents of a base, for example sodium hydride, potassium tert-butylate or alkaline earth metal oxide or hydroxide, for example barium hydroxide.

The desired compounds of formula Ia can be prepared from the uracils of formula XI, according to standard methods, in the presence of an inert solvent and at least 1 equivalent of a base, for example an alkali metal carbonate such as potassium carbonate,

- c) with an alkylation agent of formula XII to form an N-alkyl derivative of formula Ia ($R_{15}$=alkyl), or
- d) in analogy to WO 97/05116 with a hydroxylamine derivative of formula XIII, wherein $L_1$ is a leaving group such as $HOS(O)_2O$—,

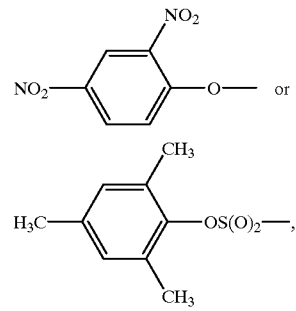

for example 2,4-dinitrophenylhydroxylamine or hydroxylamine-O-sulfonic acid, to form the N-amino derivative of formula Ia ($R_{15}$=amino). The desired thiono derivatives of formula Ia ($X_6$, $X_7$=S) can be obtained by thionization, for example with phosphorus pentasulfide or Lawesson's reagent.

The preparation of a compound of formula Ib (Ib)

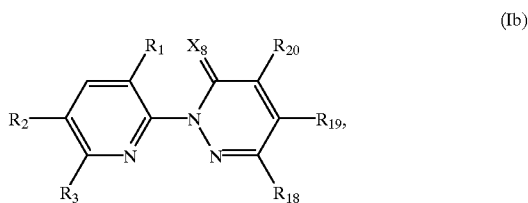

wherein $R_1$, $R_2$, $R_3$, $R_{18}$, $R_{19}$, $R_{20}$, and $X_8$ are as defined under formula I, is explained in the following reaction scheme 3.

Reaction scheme 3

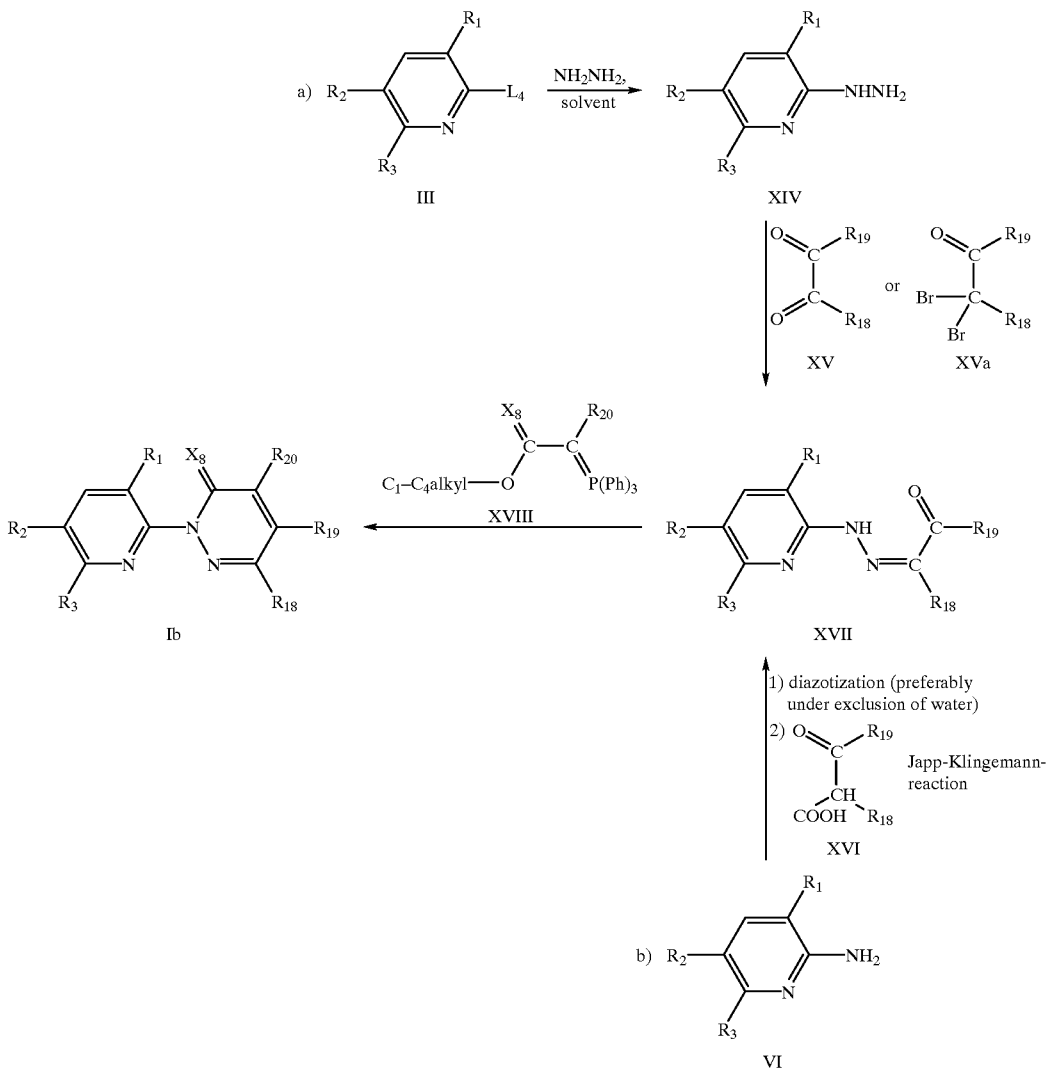

The compounds of formula Ib can be prepared according to known methods, for example according to reaction scheme 3 (variant a)) by reacting a 2-halogen pyridine derivative of formula III (L4=halogen) with hydrazine, preferably in an amphiprotic solvent, such as alcohols, by analogy with GB-A-2 230 261, to form the 2-hydrazino derivative of formula XIV.

This is reacted with a diketone of formula XV, by analogy with DE OS-19754348, or with a dihalogen ketone of formula XVa, by analogy with WO 97/07104, to form the hydrazone derivative of formula XVII.

Subsequent cyclization to the desired compound of formula Ib takes place in the presence of the phosphoran derivative of formula XVIII, if necessary in the presence of a base, for example 4-dimethylaminopyridine. If $X_8$=O in a compound of formula Ib, then thionization can subsequently be carried out in a manner similar to that described under reaction scheme 2($X_8$=S).

According to reaction scheme 3, the hydrazone derivative of formula XVII can also be obtained from the 2-aminopyridine derivative of formula VI by means of diazotization, preferably under exclusion of water, and subsequent coupling with the keto acid of formula XVI (Japp-Klingemann reaction similar to that described under DE-OS-19754348)—(variant b) in reaction scheme 3).

The preparation of a compound of formula Ig

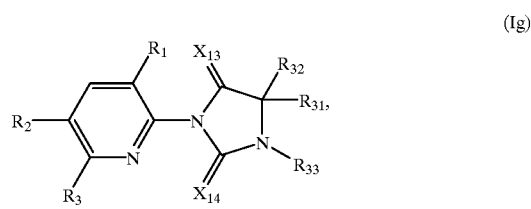

(Ig)

wherein $R_1$, $R_2$, $R_3$, $R_{31}$, $R_{32}$, $R_{33}$, and $X_{14}$ are as defined under formula I, is explained in the following reaction scheme 4.

Reaction scheme 4

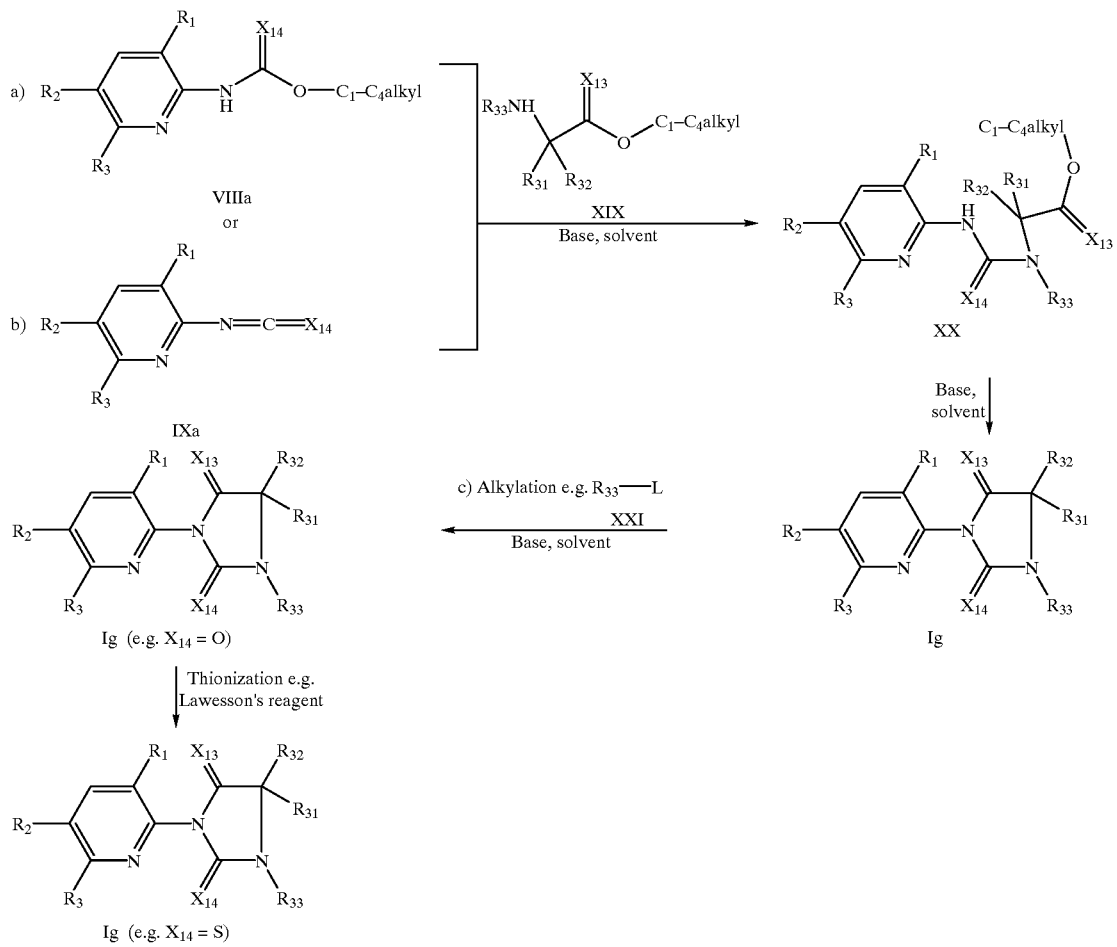

Compounds of formula Ig can be prepared in a manner analogous to known methods, as described, for example, in EP-A-0 272 594, EP-A-0 493 323, DE-A-3 643 748, WO 95/23509, U.S. Pat. No. 5,665,681 or U.S. Pat. No. 5,661,109.

For example, according to reaction scheme 4, either a) a carbamate derivative of formula VIIIa in the presence of a solvent and a base, or b) an iso(thio-)cyanate of formula IXa, if necessary in a suitable solvent, can be cyclized with an amino acid derivative of formula XIX via a compound of formula XX in the presence of a base and a suitable solvent to form a compound of formula Ig.

For those cases (variant c)) where, in a compound of formula Ig, $R_{33}$ is hydrogen and $X_{13}$ and/or $X_{14}$ are/is oxygen, alkylation can subsequently be carried out, if necessary with an alkylation reagent of formula XXI, on the free N-atom of the hydantoin ring and the ring carbonyl group then thionized ($X_{13}$ and/or $X_{14}$=S).

The preparation of a compound of formula Ih

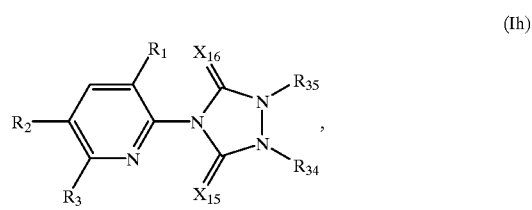

(Ih)

wherein $R_1$, $R_2$, $R_3$, $R_{34}$, $R_{35}$, $X_{15}$, and $X_{16}$ are as defined under formula I, is explained in the following reaction scheme 5.

Reaction scheme 5

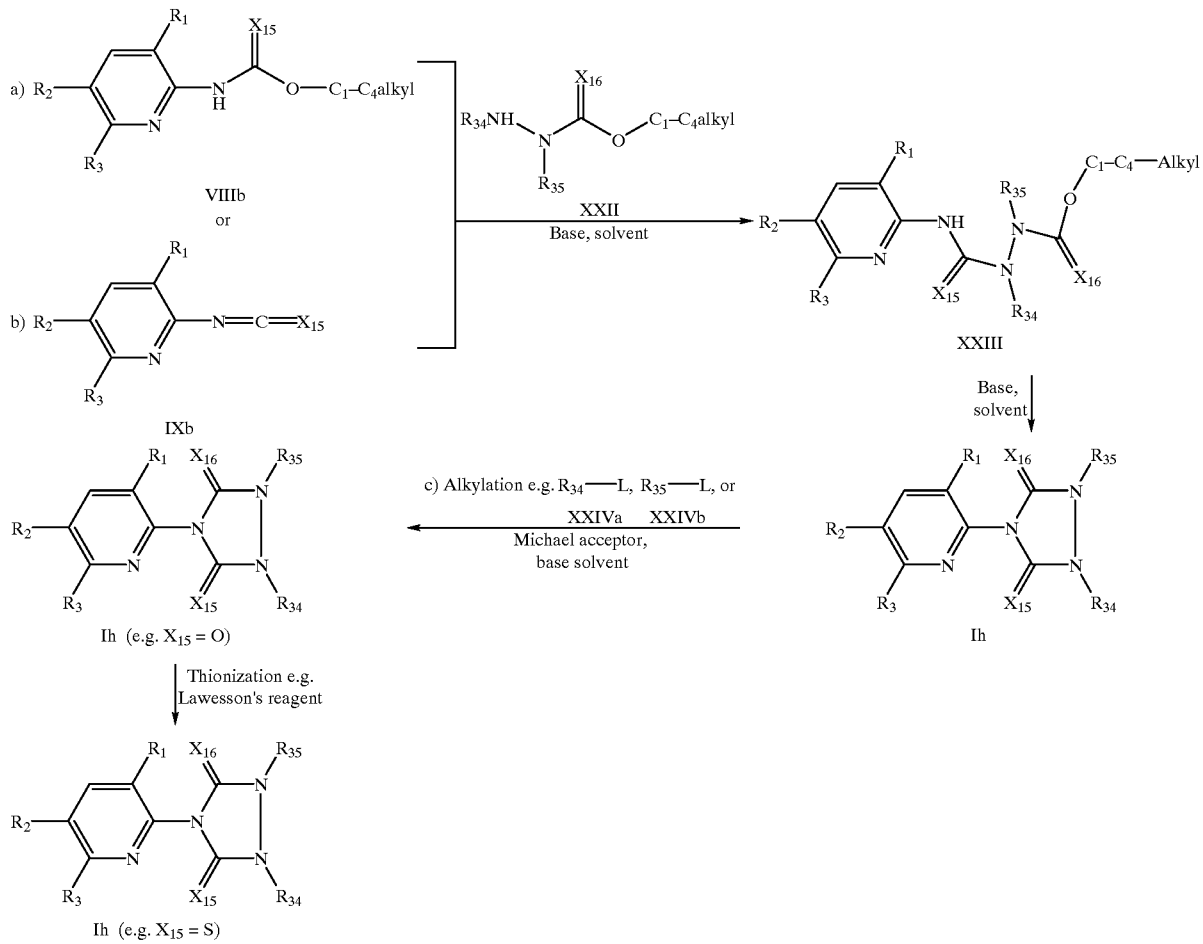

Compounds of formula Ih can be prepared in a manner analogous to known methods, as described for example in EP-A-0 210 137, DE-OS-2 526 358, EP-A-0 075 267 or EP-A-0 370 955.

For example, according to reaction scheme 5, either a) a carbamate derivative of formula VIIIb in the presence of a solvent and a base, or b) an iso(thio-)cyanate of formula IXb, if necessary in a suitable solvent, can be cyclized with a carbazate of formula XXII via a compound of formula XXIII in the presence of a base and a suitable solvent to form a compound of formula Ih.

For those cases (variant c)) where, in a compound of formula Ih, $R_{34}$ and/or $R_{35}$ are/is hydrogen and $X_{15}$ and/or $X_{16}$ are/is oxygen, alkylation can subsequently be carried out with an alkylation reagent of formula XXIVa or XXIVb on the free N-atoms and the ring carbonyl groups then thionized with a thionization reagent ($X_{15}$ and/or $X_{16}$=S).

For the preparation of compounds of formula Ih in reaction scheme 5, wherein $R_{34}$ and $R_{35}$ together form an alkylene bridge which is broken for example by —S(O)$_2$—, a compound of formula Ih, wherein $R_{34}$ and $R_{35}$ are hydrogen, can be reacted for example with an appropriate Michael acceptor, e.g. CH$_2$=CH—S(O)$_2$CH$_3$ or CH$_2$=CH—S(O)$_2$—CH=CH$_2$, and the resulting Michael addition products then functionalized.

The preparation of a compound of formula Ic

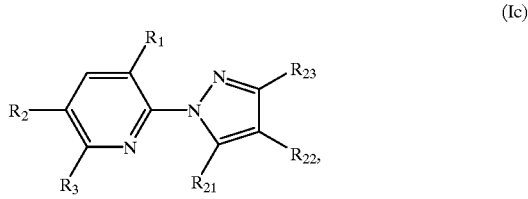

(Ic)

wherein $R_1$, $R_2$, $R_3$, and $R_{21}$ to $R_{23}$ are as defined under formula I, is explained in the following reaction scheme 6.

Reaction scheme 6

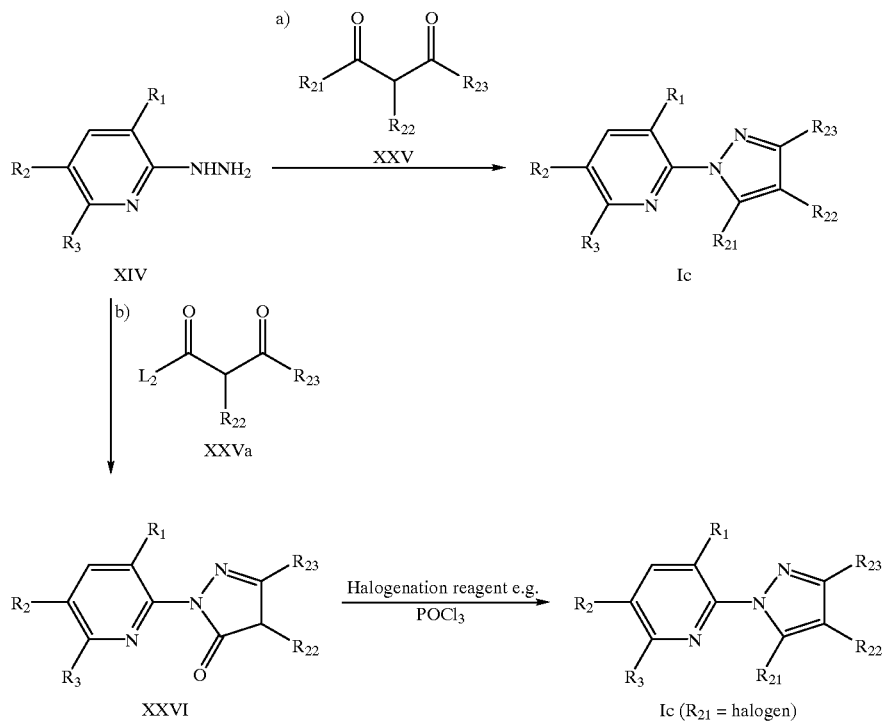

According to reaction scheme 6, the pyrazol compounds of formula Ic can be prepared e.g. either from the hydrazinopyridine derivatives of formula XIV by means of condensation with a 1,3-dicarbonyl derivative of formula XXV (variant a)), or by means of condensation with a β-carbonylcarboxylic acid derivative of formula XXVa, where $L_2$ is a leaving group, such as $C_1$–$C_4$alkoxy, hydroxy or halogen, for example chlorine or bromine (variant b)), and subsequent treatment of the resulting pyridylpyrazolone derivative of formula XXVI with a halogenation agent, for example phosphorus oxychloride ($R_{21}$=halogen). The two reaction steps a) and b) in reaction scheme 6 are carried out if necessary in the presence of an acidic, basic or bifunctional catalyst, such as p-toluenesulfonic acid.

The compounds of formula Ic obtained in this way can be further functionalized using standard methods according to the definition of substituents $R_{21}$ to $R_{23}$.

Compounds of formula Ic in reaction scheme 6, wherein $R_{22}$ is hydrogen, can be further functionalized according to the definition of $R_{22}$, e.g. using an electrophilic reagent, for example a halogenation agent, such as an elementary halogen or sulfurylhalogenide, to form the corresponding compounds of formula Ic, wherein $R_{22}$ is halogen, or using a nitrating agent such as nitric acid in a mixture with a further strong acid, such as sulfuric acid, to form the corresponding compounds of formula Ic, wherein $R_{22}$ is nitro.

The preparation of a compound of formula Id (Id)

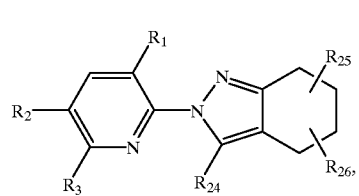

wherein $R_1$, $R_2$, $R_3$, and $R_{24}$ to $R_{26}$ are as defined under formula I, is explained in the following reaction scheme 7.

Reaction scheme 7

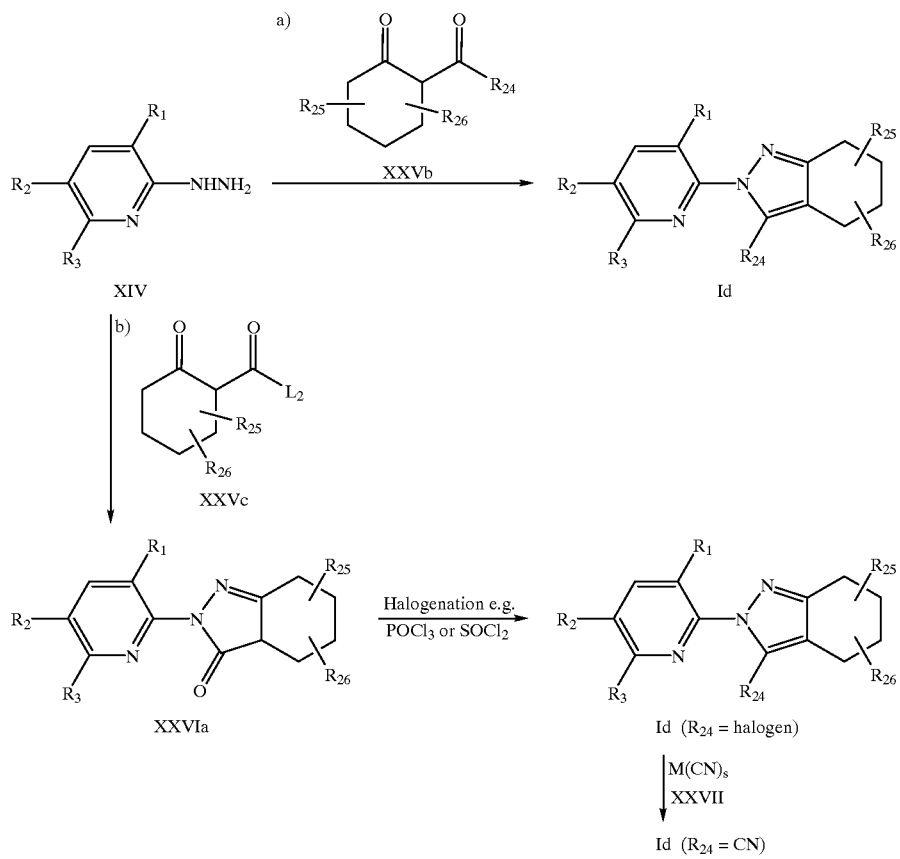

According to reaction scheme 7, the tetrahydroindazol compounds of formula Id can be obtained by known methods from the hydrazinopyridine derivatives of formula XIV, for example either by means of condensation with a cyclohexanone derivative of formula XXVb acylated in the 2-position, wherein $R_{24}$ is as defined under formula I, except where $R_{24}$ is halogen or cyano (variant a)), or by means of condensation with a cyclohexanone derivative of formula XXVc, wherein $L_2$ is a leaving group, such as $C_1$–$C_4$alkoxy, hydroxy or halogen, for example chlorine or bromine, and subsequent halogenation (variant b)) in a manner analogous to that described under reaction scheme 6.

The halogen derivatives of formula Id, wherein $R_{24}$ is halogen, can be reacted according to known methods with an alkali metal, ammonium or metal cyanide, wherein the metal ion is selected from the first or second subgroup of the periodic system, if necessary with the addition of an alkali metal iodide, to form the corresponding cyano-substituted derivatives pf formula Id ($R_{24}$=CN).

The preparation of compounds of formulae Ie and If

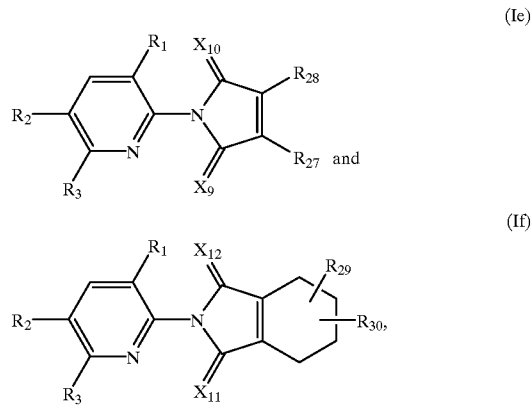

wherein $R_1$, $R_2$, $R_3$, $R_{27}$ to $R_{30}$ and $X_9$ to $X_{12}$ are as defined under formula I, is explained the following reaction scheme 8.

Reaction scheme 8

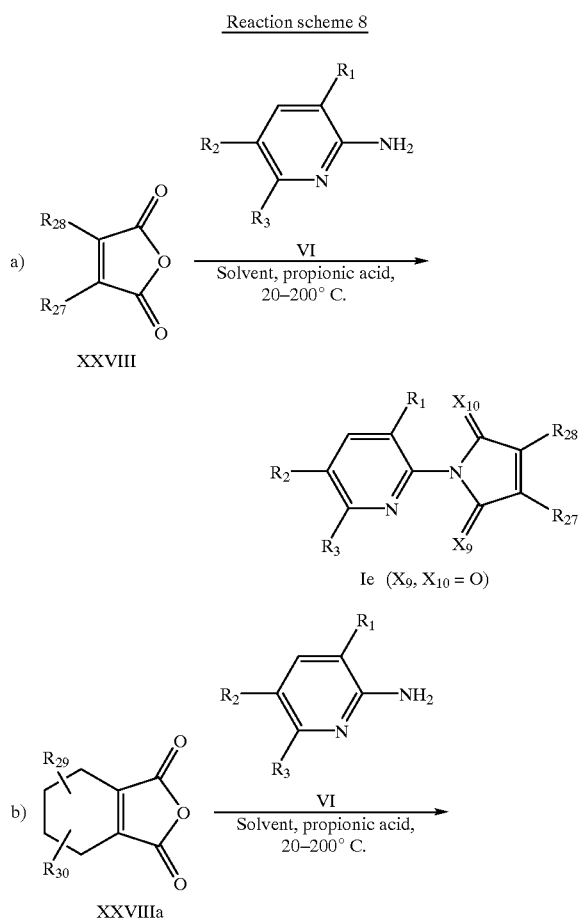

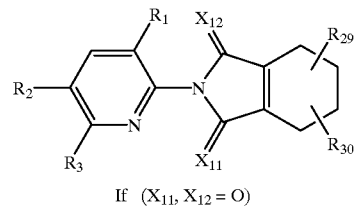

If $(X_{11}, X_{12} = O)$

According to reaction scheme 8, the pyrrolindione derivatives of formula Ie and the tetrahydroisoindolindione derivatives of formula If can be obtained in a manner analogous to known methods, for example by reacting an anhydride of formula XXVIII (variant a)) and/or XXVIIIa (variant b)) with an aminopyridine of formula VI in an inert solvent, such as ether, for example dioxan, or a lower alkylcarboxylic acid, for example propionic acid, at temperatures of 20–200° C.

The compounds of formulae Ie and If ($X_9$ to $X_{12}$=O) which are obtainable according to reaction scheme 8 can be thionized if necessary with a suitable sulfur reagent ($X_9$ to $X_{12}$=S).

The preparation of a compound of formula Ii

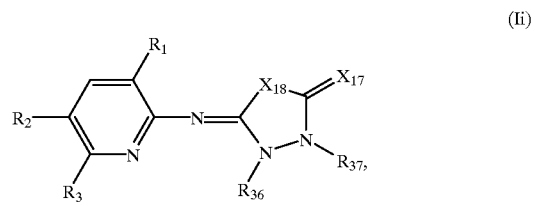

(Ii)

wherein $R_1$, $R_2$, $R_3$, $R_{36}$, $R_{37}$, $X_{17}$, and $X_{18}$ are as defined under formula I, is explained following reaction scheme 9.

Reaction scheme 9

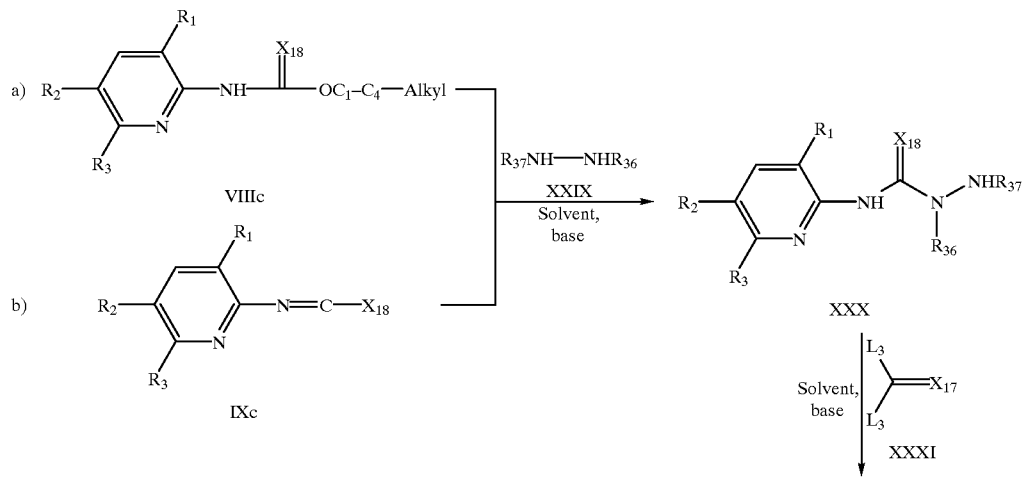

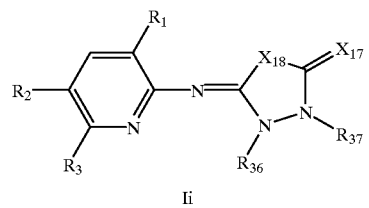

Ii

According to reaction scheme 9, compounds of formula Ii can be prepared by known methods, for example by first reacting a carbamate of formula VIIIc (variant a)) and/or an isothiocyanate of formula IXc (variant b)) with a hydrazine derivative of formula XXIX to form the semicarbazide derivative of formula XXX, and then cyclizing this derivative in the presence of a carbonylation or thiocarbonylation reagent of formula XXXI. Both reaction steps are usefully accomplished in a suitable solvent and in the presence of a base. A suitable (thio)carbonylation reagent of formula XXXI is for example phosgene, diphosgene, thiophosgene or carbonyidiimidazol. $L_3$ in a compound of formula XXXI is therefore a leaving group such as a halogen, for example, chlorine or bromine, trichloromethoxy or

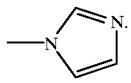

The preparation of a compound of formula Ik

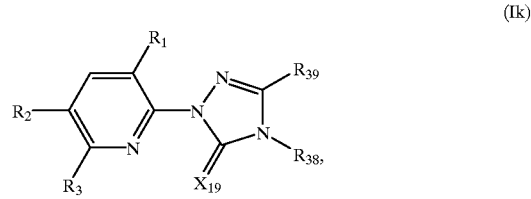

wherein $R_1$, $R_2$, $R_3$, $R_{38}$, $R_{39}$, and $X_{19}$ are as defined under formula I, is explained in the following reaction scheme 10.

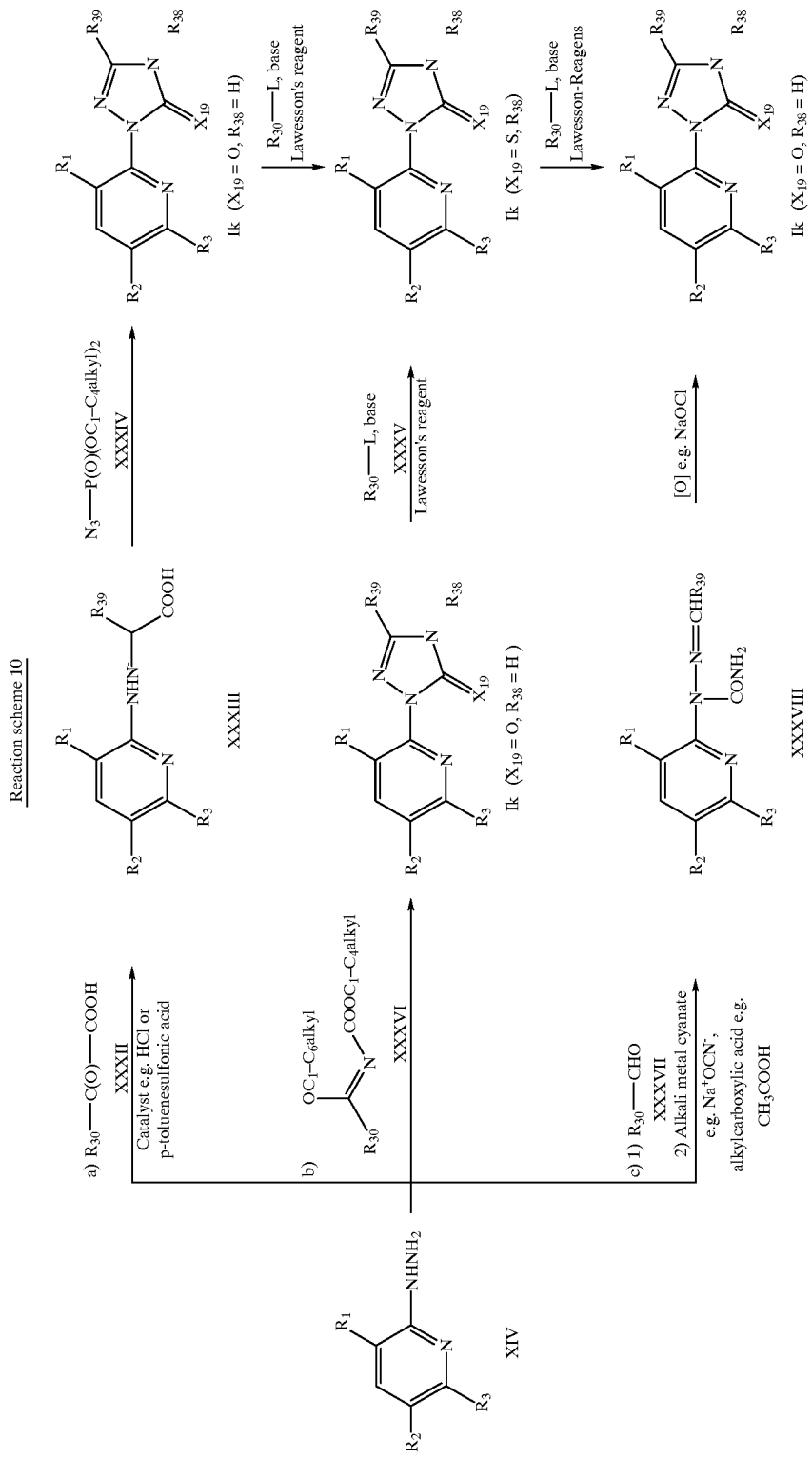

According to reaction scheme 10, the triazolone derivatives of formula Ik can be prepared in a manner analogous to known methods, starting for example from the hydrazinopyridine derivative of formula XIV, which according to variant a) is usefully reacted with a keto acid of formula XXXII in the presence of an acid catalyst, such as a lower alkylcarboxylic acid, for example propionic acid, a mineral acid, for example sulfuric acid or hydrochloric acid, or a sulfonic acid, for example p-toluenesulfonic acid, to form a hydrazone derivative of formula XXXIII. This can subsequently be cyclized with an azide of formula XXXIV to form a triazolone derivative of formula Ik, wherein $X_{19}$ is oxygen, and $R_{38}$ is hydrogen, and then further derivatized if necessary according to standard methods using an alkylation reagent of formula XXXV or a sulfur reagent.

According to variant b), the hydrazinopyridine derivative of formula XIV can be cyclized with an iminoether of formula XXXVI to form a triazolone derivative of formula Ik, wherein $X_{19}$ is oxygen, and $R_{38}$ is hydrogen, and then if necessary alkylated or thionized as described under variant a).

According to variant c) in reaction scheme 10, the hydrazinopyridine derivative of formula XIV can be reacted first with an aldehyde of formula XXXVII and then, in the presence of a lower alkylcarboxylic acid, such as acetic acid, with an alkali metal cyanate to form a compound of formula XXXVIII which, if necessary, is not isolated, and finally cyclized with an oxidizing agent, such as alkali metal hypochlorite (Javelle) to form a compound of formula Ik, wherein $X_{19}$ is oxygen, and $R_{38}$ is hydrogen. If necessary, the resulting compound of formula Ik can be alkylated or thionized, as described under variant a).

In certain cases, compounds of formula I can also be usefully obtained in a manner analogous to that described in J. Het. Chem. 15, 1221 (1978) by the substitution of a 2-halogen pyridine of formula III ($L_4$=halogen), if necessary in the presence of a suitable solvent and a base, with the desired heterocycles of formulae $W_{01}$ to $W_{010}$ (W01)

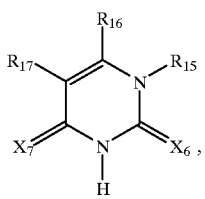

(W02)

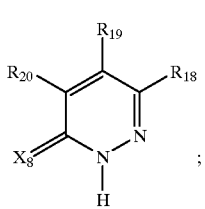

W03)

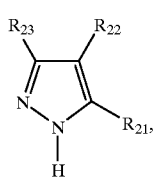

-continued (W04)

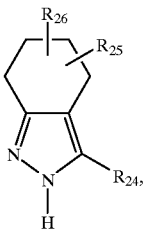

(W05)

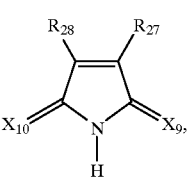

(W06)

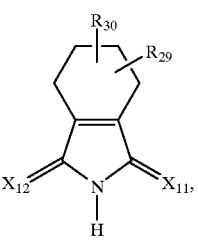

(W07)

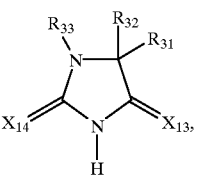

(W08)

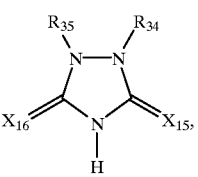

(W09)

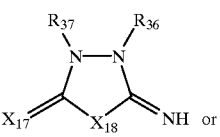

NH or (W010)

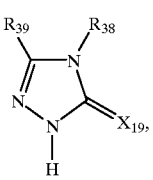

or alkali metal salts thereof, as illustrated with the example of a compound of formula Ic in reaction scheme 11.

Reaction scheme 11

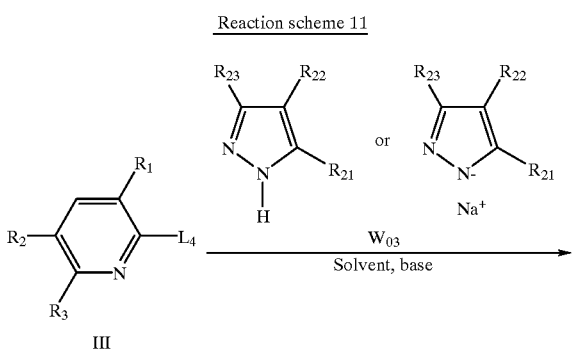

wherein $R_1$ and $R_2$ are as defined under formula I, $L_4$ is a leaving group, such as halogen or $C_1$–$C_4$alkyl or phenylsulfonyl, and W is a $W_3$, $W_4$, $W_5$, $W_6$, $W_9$ or $W_{10}$ group, are new. The invention thus also relates to these compounds.

The preparation of compounds of formula II is explained in reaction scheme 12.

Reaction scheme 12:

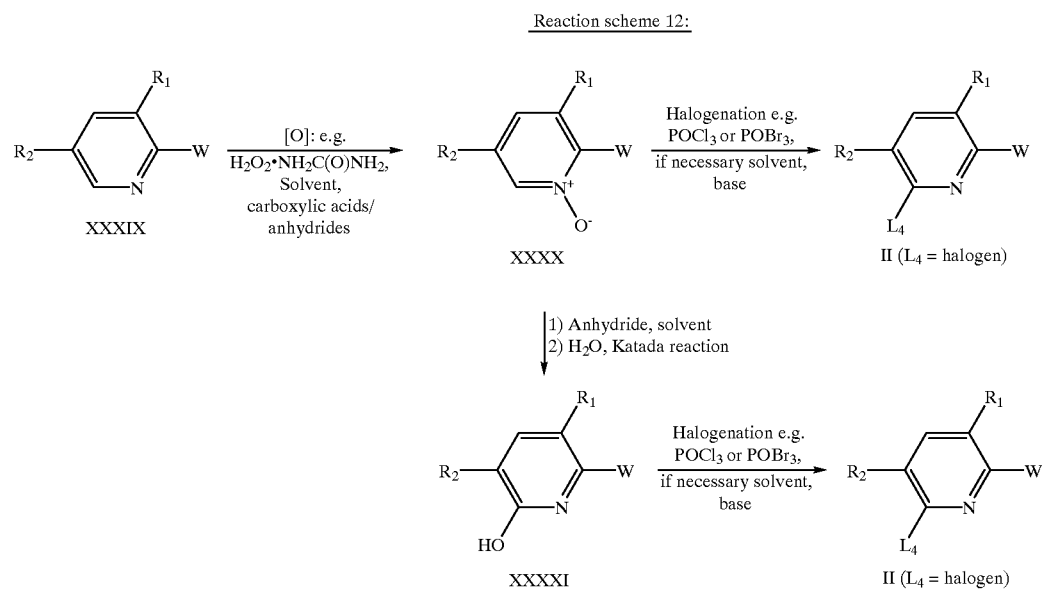

-continued

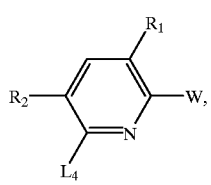

The intermediate products of formula II (II)

The pyridin-N-oxides of formula XXXX (reaction scheme 12) can be prepared according to known methods, such as described in Org. Synth. 4, 828 (1963); ibid. 3, 619 (1955); U.S. Pat. No. 3,047,579; and B. Iddon and H. Suschitzky in "Polychloroaromatic Compounds", Editor H. Suschitzky, Plenum Press, London 1974, page 197, a useful method being to react the pyridine derivatives of formula XXXIX with oxidizing agents, such as organic peroxy acids, for example m-chloroperbenzoic acid, peracetic acid and pertrifluoracetic acid, or aqueous hydrogen peroxide solution or hydrogen peroxide urea adduct together with carboxylic acids and/or carboxylic acid anhydrides, or inorganic peroxy acids, for example peroxymonosulfuric acid (Caro's acid).

Suitable solvents are, for example, water, organic acids such as acetic acid and trifluoracetic acid, halogenated hydrocarbons such as dichloromethane and 1,2-dichloroethane, esters such as ethyl acetate, ethers such as tetrahydrofuran and dioxan or mixtures comprising these solvents. The reaction temperatures lie within the range of −20° C. to 100° C., depending on the solvent or solvent mixture used.

The pyridin-N-oxides of formula XXXX can be halogenated either directly according to known methods, for example with phosphorus oxychloride, phosphorus oxybromide, sulfuryl chloride, thionyl chloride or phosphorus pentachloride in phosphorus oxychloride to form the halogen pyridine derivatives of formula II (L$_4$=halogen), or first reacted—likewise according to known methods (e.g. Quart. Rev. 10, 395 (1956); J. Am. Chem. Soc. 85, 958 (1963); and J. Org. Chem. 26, 428 (1961))—in the presence of anhydrides, for example acetic anhydride, trifluoracetic anhydride and methanesulfonic acid anhydride in a suitable inert solvent, such as halogenated hydrocarbons, for example dichloromethane and 1,2-dichloroethane, amides such as N,N-dimethylformamide and 1-methyl-2-pyrrolidone and if necessary in the presence of sodium acetate, to form the pyridol derivatives of formula XXXXI, which can then then be halogenated to form halogen pyridines of formula II, as described above for compounds of formula XXXX (L$_4$=halogen). The reaction temperatures for this transformation reaction generally lie within the range of −30° C. to 80° C. By analogy with Tetrahedron 37, 187 (1981), antimony pentachloride (Katada reaction) presents itself as a further variant for the above transformation reaction.

The method described in the invention for the preparation of compounds of formula II

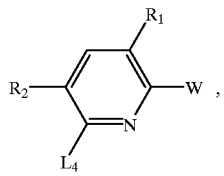

(II)

wherein R$_1$ and R$_2$ are as defined under formula I, W is a W$_1$ to W$_{10}$ group, and L$_4$ is a C$_1$–C$_4$alkyl or phenylsulfonyl group, is carried out starting from a compound of formula II wherein R$_1$, R$_2$ and W have the meanings indicated and L$_4$ is halogen, by means of reaction with a C$_1$–C$_4$alkyl or phenyl thiol in the presence of a suitable base, followed by oxidation of the resulting thioether with an oxidizing agent such as hydrogen peroxide or m-chloroperbenzoic acid.

The starting compounds of formula XXXIX used in reaction scheme 12 can be prepared in a manner analogous to the methods described for compounds of formula Ia to Ik (R$_3$=hydrogen) under reaction schemes 2 to 11.

The compounds of formulae III and VI are known or can be prepared according to known methods, as described in DE-A-3 917 469; WO 97/07114; WO 92/00976; JP-A-58-213 776; EP-A-0 012 117; EP-A-0 306 547; EP-A-0 030 215; EP-A-0 272 824; EP-A-0 500 209; U.S. Pat. Nos. 4,996,323; 5,017,705; WO 97/05112; J. Het. Chem. 11, 889 (1974); J. Het. Chem 21, 97 (1984); Tetrahedron 41, 4057 (1985); Heterocycles 22,117; Synth. 1988, 938; J. Med. Chem. 25, 96. The 2-aminopyridines of formula VI can in addition be prepared by Curtius, Hofmann or Lossen reactions from corresponding pyridine derivatives with carboxylic acid, carboxylic acid chloride, carboxylic acid azide, carboxylic acid ester or carboxylic acid amide functions in Position 2.

The reagents of formulae V, VII, X, XII, XIII, XV, XVa, XVI, XVIII, XIX, XXI, XXII, XXIVa, XXIVb, XXV, XXVa, XXVb, XXVc, XXXIV, XXVIII, XXVIIIa, XXIX, XXXI, XXXII, XXXIV, XXXV, XXXVI and XXXVII as used in reaction schemes 1 to 10 are either known or can be prepared in a manner analogous to disclosed methods.

The heterocycles of formulae W$_{01}$ to W$_{010}$ are either known or can be prepared in a manner analogous to known standard methods of heterocyclic chemistry.

The reactions for obtaining the compounds of formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers, including diethyl ether, 1,2-dimethoxyethane, diglyme, tetrahydrofuran or dioxane, nitriles such as acetonitrile or propionitrile, amides such as N,N-dimethyl formamide, diethyl formamide or N-methylpyrrolidinone. The reaction temperatures are preferably in the range from −20° to +120° C. The reactions are usually slightly exothermic and can as a rule be carried out at room temperature. The reaction mixture can be heated for a brief time to boiling point to shorten the reaction time or also to initiate the reaction. The reaction times can also be shortened by addition of a few drops of a base as reaction catalyst. Particularly suitable bases are tertiary amines such as trimethylamine, triethylamine, quinuclidine, 1,4-diazabicyclo[2.2.2]octane, 1,5-diazabicyclo[4.3.0]non-5-ene or 1,5-diazabicyclo[5.4.0]undec-7-ene. Further suitable bases are also inorganic bases, typically hydrides such as sodium or calcium hydride, hydroxides such as sodium and potassium hydroxide, carbonates such as sodium and potassium carbonate, or hydrogencarbonates such as potassium and sodium hydrogencarbonate.

The compounds of formula I can be isolated in conventional manner by concentrating the reaction mixture and/or removing the solvent by evaporation and by recrystallizing or triturating the solid residue in a solvent in which it is not readily soluble, typically an ether, an aromatic hydrocarbon or a chlorinated hydrocarbon, or by means of column chromatography and a suitable eluent.

The compounds of formula I or compositions containing them may be used according to this invention by all standard methods of application used in agriculture, including preemergence application, postemergence application and seed dressing, as well as by different methods and techniques such as controlled release. For controlled release, a solution of the herbicide is applied to mineral granular carriers or to polymerized granules (urea/formaldehyde) and then dried. A coating can then be additionally applied (coated granules) that allows the herbicide to be released at a controlled rate over a specific period of time.

The compounds of formula I may be used as herbicides in unmodified form, i.e. as obtained in the synthesis. Preferably they are processed in conventional manner with the auxiliary agents customarily employed in formulation technology, e.g. to emulsifiable concentrates, directly sprayable or dilutable solutions, dilute emulsions, wettable powders, soluble powders, dusts, granulates or microcapsules. Such formulations are described, for example, in WO 97/34485 on pages 9 to 13. As with the type of agents, the methods of application such as spraying, atomizing, dusting, wetting, scattering or pouring, are selected in accordance with the intended objectives and the prevailing circumstances.

The formulations, i.e. the agents, preparations, or compositions containing the compound of formula I or at least one compound of formula I and usually one or more than one liquid or solid formulation assistant, are prepared in known manner, e.g. by homogeneously mixing and/or grinding the herbicide with said formulation auxiliaries, typically solvents or solid carriers. Surface-active compounds (surfactants) may additionally be used for preparing the formulations. Examples of solvents and solid carriers are described in WO 97/34485 on page 6.

Depending on the herbicide of formula I to be formulated, suitable surface-active compounds are nonionic, cationic and/or anionic surfactants and surfactant mixtures having good emulsifying, dispersing and wetting properties.

Examples of suitable anionic, non-ionic, and cationic surfactants are listed in WO 97/34485 on pages 7 and 8.

Also the surfactants customarily employed in the art of formulation and described, inter alia, in "McCutcheon's Detergents and Emulsifiers Annual" MC Publishing Corp., Ridgewood N.J., 1981, Stache, H., "Tensid-Taschenbuch" (Handbook of Surfactants), Carl Hanser Verlag, Munich/Vienna, 1981, and M. and J. Ash, "Encyclopedia of Surfactants", Vol I–III, Chemical Publishing Co., New York, 1980–81 are suitable for manufacture of the herbicides according to the invention.

The herbicidal compositions will as a rule contain from 0.1 to 99% by weight, preferably from 0.1 to 95% by weight, of herbicide, from 1 to 99.9% by weight, preferably from 5 to 99.8% by weight, of a solid or liquid adjuvant, and from 0 to 25% by weight, preferably from 0.1 to 25% by weight, of a surfactant. Whereas it is preferred to formulate commercial products as concentrates, the end user will normally use dilute formulations. The compositions may also contain further ingredients, such as: stabilisers, e.g. where appropriate epoxidized vegetable oils (epoxidized coconut oil, rapeseed oil, or soybean oil); antifoams, typically silicone oil; preservatives; viscosity regulators; binders; and tackifiers; as well as fertilizers or other chemical agents.

The compounds of formula I are usually applied with success to the plants or the locus thereof in concentrations of 0.001 to 4 kg/ha, especially 0.005 to 2 kg/ha. The concentration required to achieve the desired action can be determined by experimentation. It will depend on the type of action, the development stage of the cultivated plant and of the weed, as well as on the application (locus, time, method), and as a result of these variables can vary over a wide range.

The compounds of formula I have excellent herbicidal and growth inhibiting properties, which make them suitable for application in crops of cultivated plants, especially in cereals, cotton, soybeans, sugar beet, sugar cane, plantations, rape, maize, and rice, and for the non-selective control of weeds. Crops will also be understood as meaning those crops that have been made tolerant to herbicides or classes of herbicides by conventional breeding or genetic engineering methods. The weeds to be controlled may be monocot as well as dicot weeds, typically Stellaria, Nasturtium, Agrostis, Digitaria, Avena, Setada, Sinapis, Lolium, Solanum, Echinochloa, Scirpus, Monochoda, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola, and Veronica.

The invention is illustrated by the following non-limitative Examples.

PREPARATIVE EXAMPLES

Example H1

Preparation of 2-N-ethoxicarbonylamino-3-fluoro-5-chloropyridine

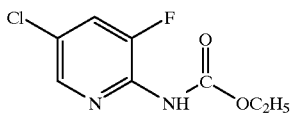

294 g 2-Amino-3-fluoro-5-chloropyridine is dissolved in 1 l dry pyridine and cooled to 0° C., then 220 g ethyl chloroformate is stirred in drop by drop and stirring continued at 22° C. until the reaction is complete. The reaction mixture is then poured onto ice water, adjusted to pH 4–5 with 2N hydrochloric acid and extracted with ethyl acetate. The combined extracts are washed with water, dried over sodium sulfate, concentrated by evaporation and crystallized by the addition of n-hexane. The precipitate obtained is filtered off, washed with n-hexane and dried in a vacuum. The title compound is obtained with a melting point of 132° C.

Example H2

Preparation of 1-(3-fluoro-5-chloropyridin-2-yl)-3-methyl-4-trifluoromethylpyrimidin-2,6-dione

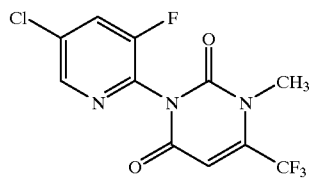

Under a nitrogen atmosphere, while cooling and stirring, a solution of 22.7 g 4,4,4-trifluoro-3-amino-2-butenoic acid ethyl ester is added dropwise to 5.1 g of a sodium hydride dispersion (60%) in 60 ml N-methylpyrrolidine at 0–5° C. and stirred at 22° C. until hydrogen evolution is complete. Then 23.7 g 2-ethoxicarbonylamino-3-fluoro-5-chloropyridine (Example H1) is added and the reaction mixture heated for about 5 hours to 120° C. The mixture is then cooled, 16.7 g methyl iodide is added dropwise and stirring is continued overnight at 22° C. After the reaction mixture has been taken up in ethyl acetate, it is washed with ice water, dried over sodium sulfate, filtered, and concentrated by evaporation. The residue obtained is recrystallized from ethyl acetate/n-hexane. The title compound is obtained with a melting point of 133–134° C.

Example H3

Preparation of 1-(3-fluoro-5-chloro-2-pyridyl-N-oxide)-3-methyl-4-trifluoromethylpyrimidin-2,6-dione

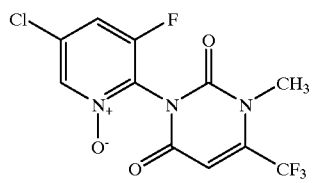

24 g 1-(3-Fluoro-5-chloropyridin-2-yl)-3-methyl-4-trifluoromethylpyrimidin-2,6-dione (Example H2) in 150 ml dichloromethane is cooled to −5° C., and 2 g hydrogen peroxide-urea adduct is added. Then 2.7 ml trifluoroacetic acid anhydride, dissolved in 2 ml dichloromethane, is added dropwise and the reaction mixture is stirred overnight after the exothermic reaction has subsided. Within 3 hours another 5 g of hydrogen peroxide-urea adduct and 3 ml trifluoroacetic acid anhydride are added in 2 portions and, after the exothermic reaction has subsided, the mixture is heated to 25–35° C. until the reaction is complete. The mixture is then cooled and, at −5° C., is adjusted to pH 7.5 first with 2N sodium hydroxide solution, then with saturated sodium hydrogencarbonate solution, distributed between dichloromethane and ice water, and the separated organic phase dried over sodium sulfate, filtered and concentrated by evaporation. The remaining solid residue is recrystallized from ethyl acetate/n-hexane. The desired title compound is obtained with a melting point of 142–143° C.

Example H4

Preparation of 1-(3-fluoro-5,6-dichloro-2-pyridyl)-3-methyl-4-trifluoromethylpyrimidin-2,6-dione

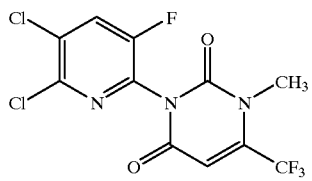

To a solution of 2.4 ml phosphorus oxytrichloride in 20 ml 1,2-dichloroethane, heated to 70° C., portions of 6.8 g 1-(3-fluoro-5-chloro-2-pyridyl-N-oxide)-3-methyl-4-trifluoromethylpyrimidin-2,6-dione (Example H3) are added, maintained at this temperature overnight, before a further 4.0 ml phosphorus oxytrichloride is added and heated for 20 hours. The mixture is then cooled, poured over ice water, extracted with dichloroethane, and the combined extracts are washed with 2N sodium hydroxide solution and water, dried over sodium sulfate and evaporated by concentration. The residue is purified by means of silica gel chromatography (eluent: hexane/ethyl acetate 9/1). The title compound is obtained with a melting point of 113–115°C.

Example H5

Preparation of 1-(2-hydroxy-3-chloro-5-fluoropyridin-6-yl)-3-methyl-4-trifluoromethylpyrimidin-2,6-dione and 1-(3-hydroxy-2-chloro-5-fluoropyridin-6-yl)-3-methyl-4-trifluoromethylpyrimidin-2,6-dione

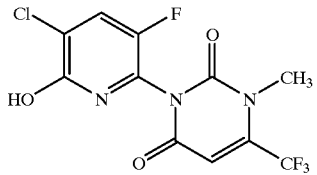

and

To a solution of 29.6 g 1-(3-fluoro-5-chloro-2-pyridyl-N-oxide)-3-methyl-4-trifluoromethylpyrimidin-2,6-dione (Example H3) in 400 ml dimethylformamide, cooled to −30° C., 182 g trifluoroacetic acid anhydride is added dropwise, and the mixture is then stirred overnight at −30° C., and on the next day at 22° C. In a vacuum, the mixture is then liberated from surplus trifluoroacetic acid anhydride, cooled to −5° C. and carefully neutralized first with diluted sodium hydroxide solution and then with sodium hydrogencarbonate solution. After the addition of ice water, the mixture is extracted with ethyl acetate, and the combined extracts are washed with water and dried over sodium sulfate. This is then filtered, the filtrate concentrated by evaporation and the resulting residue purified over a silica gel column (eluent: n-hexane/ethyl acetate 8/2) with an ascending gradient in respect of ethyl acetate. The title compound is obtained with a melting point of 200–202° C.

In addition, a fraction is obtained which, besides 1-(2-hydroxy-3-chloro-5-fluoropyridin-6-yl)-3-methyl-4-trifluoromethylpyrimidin-2,6-dione, comprises also the isomer 1-(3-hydroxy-2-chloro-5-fluoropyridin-6-yl)-3-methyl-4-trifluoromethylpyrimidin-2,6-dione. The latter isomeric compound is obtained by a further rearrangement reaction. The ratio of the two isomers 1-(2-hydroxy-3-chloro-5-fluoropyridin-6-yl)-3-methyl-4-trifluoromethylpyrimidin-2,6-dione and 1-(3-hydroxy-2-chloro-5-fluoropyridin-6-yl)-3-methyl-4-trifluoromethylpyrimidin-2,6-dione varies (at approx. 3:1) depending on reaction conditions.

The isomeric mixture of the fraction can either be used directly for the next reaction step or separated by means of HPLC (Li-Chrospher Si60; eluent: ethyl acetate/hexane 15/85 to 30/70, ascending gradient of ethyl acetate). Pure 1-(3-hydroxy-2-chloro-5-fluoropyridin-6-yl)-3-methyl-4-trifluoromethylpyrimidin-2,6-dione is obtained with a melting point of 189–192° C.

Example H6

Preparation of 1-(6-Ethoxicarbonyl-5-chloro-3-fluoropyridin-2-yl)-3-methyl-4-trifluoromethylpyrimidin-2,6-dione

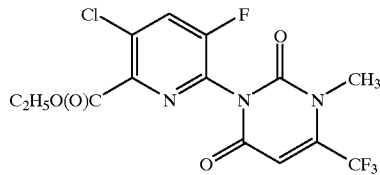

A mixture of 4 g 1-(3-fluoro-5,6-dichloro-2-pyridyl)-3-methyl-4-trifluoromethylpyrimidin-2,6-dione (Example H4), 3.4 g triethylamine and 2 g dichloro-bis(triphenylphosphine)palladium in 50 ml ethanol is pressurized in an autoclave with carbon monoxide at 180 bar and the mixture heated for about 30 hours to 101° C., leading to a pressure build-up of max. 228 bar. The heating is then switched off, the reaction mixture left to stand at 22° C. over the weekend and filtered; the filtrate is then concentrated by evaporation in a vacuum, and the residue obtained is purified over a silica gel column (eluent: n-hexane/ethyl acetate 9/1). The desired title compound is obtained as a yellowish resin.

Example H7

Preparation of 1-(2-trifluoromethyl-3-chloro-5-fluoropyridin-6-yl)-3-methyl-4-trifluoromethylpyrimidin-2,6-dione

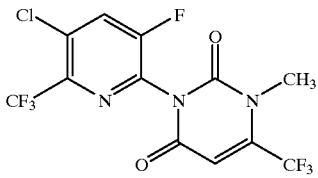

To a solution of 0.848 g of a mixture of 2-hydroxy-3-chloro-5-fluoropyridin-6-yl)-3-methyl-4-trifluoromethylpyrimidin-2,6-dione and 3-hydroxy-2-chloro-5-fluoropyridin-6-yl)-3-methyl-4-trifluoromethylpyrimidin-2,6-dione (Example H5), 0.938 g triphenylphosphine, 0.22 ml 2,2,2-trifluoroethanol and 0.58 ml diethylazodicarboxylate are added at 22° C., and the mixture is stirred for 14 hours at 22° C. The same quantities of triphenylphosphine, diethylazodicarboxylate and trifluoroethanol are added and the mixture is stirred for a further 4 hours. Ice water is then added, distributed between dichloromethane and water, the extracts washed with water, dried and concentrated by evaporation. The residue is first filtered via silica gel (hexane/ethyl acetate 2/1) and then separated by means of HPLC (Li-chrospher Si 60; hexane-ethyl acetate 15–30%, ascending gradient).

After the separation of 1-(2-trifluoroethoxy-3-chloro-5-fluoro-6-pyridyl)-3-methyl-4-trifluoromethylpyrimidin-2,6-dione and 1-(3-trifluoroethoxy-2-chloro-5-fluoro-6-pyridyl)-3-methyl-4-trifluoromethylpyrimidin-2,6-dione, the desired title compound is obtained with a melting point of 112–113° C.

By analogy, these and analogous trifluoromethyl compounds are obtainable as described in JP-A-58 206 563 or by the reaction of corresponding carboxylic acid derivatives with sulfur tetrafluoride or by the reaction of corresponding trichloromethyl compounds with hydrogen fluoride.

Example H8

Preparation of tetrahydroimidazo[1,5-a]pyridin-1,3-dione

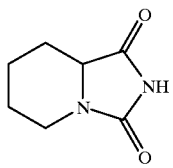

A reaction vessel containing 260 ml water is prepared with 34.6 g (0.193 mol) 2-piperidine-carboxylic acid methyl ester.hydrochloride, to which 17.4 g (0.216 mol) potassium cyanate is then added. Then 30 ml glacial acetic acid is added and the resulting homogeneous solution is stirred for 4.5 hours at 22° C. The reaction solution is subsequently saturated with saline (NaCl) and extracted twice with 200 ml tert-butyl methyl ether each time. The organic fractions are combined, dried over sodium sulfate and concentrated. As residue, 11 g of a viscous oil is obtained, from which crystals precipitate out overnight. Decanting off the remaining oil enables the crystals to be separated off and isolated by trituration (digestion) in diethyl ether. The desired title compound is obtained with a melting point of 122–123° C. in a yield of 5.75 g.

Example H9

Preparation of 2-(3-fluoro-6-chloro-5-cyano-2-pyridyl)tetrahydroimidazo[1,5-a]pyridin-1,3-dione

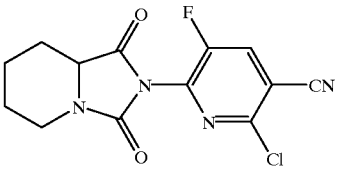

A reaction vessel is prepared with 0.77 g (0.005 mol) of the hydantoin derivative from Example H8 in 50 ml acetonitrile. To this solution, 0.95 g (0.00688 mol) finely pulverized potassium carbonate and 0.96 g (0.00503 mol) 2,6-dichloro-3-cyano-4-fluoropyridine are added consecutively, and the mixture is stirred and heated to reflux temperature for 5 hours. At the end of this time, no further starting compound is detectable (TLC analysis). The reaction mixture is cooled, filtered, and the solvent evaporated off. The dark brown, viscous oil obtained is chromatographed under pressure over a silica gel column (30 g) (eluent: hexane/ethyl acetate 2/1). The fractions comprising product with an $R_f$ value of 0.26 are combined and liberated from the solvent. The desired product is obtained as white crystals with a melting point of 192–193° C. MS (FD): [M$^+$, 40%] 308.

Example H10

Preparation of 2-(5-chloro-3-fluoropyridin-2-yl)-7-hydroxytetrahydroimidazo-(1.5-a)-pyridin-1,3-dione

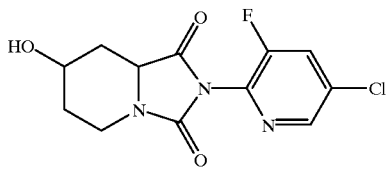

A reaction mixture comprising 100 ml dioxan, 50 ml N,N-dimethylformamide, 8 ml propylene oxide, 6 ml 1.8-diazabicyclo-(5.4.0)-undec-7-en and 8.0 g 4-hydroxypiperidine-2-carboxylic acid ethyl ester.hydrochloride is stirred overnight at 20° C. Then 4.4 g potassium tert-butylate and 50 ml N,N-dimethylformamide are added and the resulting suspension is heated for about 4 hours to 95° C. The reaction mixture is then cooled, adjusted to pH 6.5–7.0 with cold, aqueous 2N hydrochloric acid solution and extracted with ethyl acetate. The combined extracts are washed with saline solution and water, concentrated by evaporation and the solid residue purified by means of silica gel chromatography (eluent: hexane/ethyl acetate). The title compound is obtained as a mixture of two separable diastereomers with a melting point of 183–185° C. and 184–186° C.

Example H11

Preparation of 2-(5-Chloro-3-fluoro-pyridine-2-yl)-7-fluoro-tetrahydroimidazo-(1.5-a)-pyridine-1,3-dione 2.6 g of 2-(5-Chloro-3-fluoro-pyridine-2-yl)-7-hydroxitetrahydroimidazo-(1.5-a)-pyridine-1,3-dione (isomer B) in 80 ml dichlorromethane is treated at −55° C.—−65° C. with 1.9 ml of diethylaminosulfur trifluoride (DAST) and stirred at the same temperature for 1 hr. The vessel is then allowed to stir at room temperature over night. The resulting brownish solution is treated with ice and water and extracted with ethyl acetate. The extracts are washed with water, dried, filtered through a small siligcagel column and evaporated to give the desired product with m.p. 154–157° C.

Example H12

Preparation of 2-(6-ethoxycarbonyl-5-chloro-3-fluoro-pyridin-2-yl)-5-trifluoromethyl-2.H.-pyridazin-3-one (compound 35.004)

A mixture of 1.7 g 2-(5,6-dichloro-3-fluoropyridin-2yl)-5-trifluoromethyl-2.H.-pyridazin-3-one, 1 g of bis-(triphenylphosphine)-palladium(II)-dichloride, and 2.3 ml triethylamine in 35 ml ethanol was placed in an autoclave and heated under a pressure of 180–235 bar of carbon monoxide at 100° C. for 24 hrs. Then, the reaction mixture was cooled down, filtered end evaporated. Purification of the residue by HPLC-chromatography (ethyl acetate-hexane) led to the desired product. $^1$H-NMR (CDCl$_3$): 8.11 ppm (s, 1H); 7.80 ppm (d,1H); 7.35 ppm (s, 1H); 4.46 ppm (q, 2H); 1.41 ppm (t, 3H).

In an analogous manner, 2-(6-ethoxycarbonyl-5-chloro-3-fluoro-pyridin-2-yl)-4-methyl-5-trifluoromethyl-2.H.-pyridazin-3-one (39.004) was obtained.

Example H13

Preparation of 2-(5,6-dichloro-3-fluoro-pyridin)-2-yl-4-methyl-5-trifluoromethyl-2.H.-pyridazine-3-one A mixture of 1.6 g 2-(5-chloro-3-fluoro-1-oxy-pyridin-2-yl)-4-methyl-5-trifluoromethyl-2H-pyridazin-3-one and 2 ml of phenyl dichlorophosphate was heated in a sealed tube at 140° C. for 3 hrs. The reaction was then cooled, poured into ice and water, neutralised with aqueous sodium hydrogen carbonate, extracted with ethyl acetate, washed with water and dried over sodium sulfate. After dilution with hexane, the extract was filtered through silicagel and evaporated to give the desired product with m.p. 96–98° C.

Example H14

Preparation of 2-(5-chloro-3-fluoro-1-oxy-pyridin-2-yl)-4-methyl-5-trifluoromethyl-2H-pyridazin-3-one (compound 625.001)

5.01 g of 2-(5-chloro-3-fluoro-pyridin-2-yl)-4-methyl-5-trifluoromethyl-2H-pyridazin-3-one in 150 ml of 1,2-dichloroethane was treated at 0° C. with 2.1 g hydrogen peroxide-urea adduct and 2.7 ml of trifluoroacetic anhydride and allowed to stir at 20° C. until conversion was complete. Then the solution was poured into ice and water, neutralised with aqueous sodium hydrogen carbonate and extracted with dichloromethane. The extracts were combined, washed with water, dried, filtered and evaporated to give the desired product with m.p. 140–143° C.

Example H15

Preparation of 2-(5-chloro-3-fluoro-pyridin-2-yl)-4-methyl-5-trifluoromethyl-2H-pyridazin-3-one (608.001)

A solution of 8.09 g 3((5-chloro-3-fluoro-pyridine-2-yl)-hydrazono)-1,1,1-trifluoro-propan-2-one and 11.5 g 1-carbomethoxyethylidene triphenylphosphine in 200 ml dioxane was stired for 30 min. at 20° C. and then heated until complete conversion at 50° C. The reaction mixture was diluted with hexane, filtered from solid triphenylphosphine oxide through silicagel and evaporated. Further purification of the residue on silicagel (ethyl acetate-hexane 3:7) led to the desired product with m.p. 91–93° C.

Example H16

Preparation of 3-((5-chloro-3-fluoro-pyridin-2-yl)-hydrazono)-1,1,1-trifluoropropan-2-one (intermediate)

6.75 g 1,1-dibromo-3,3,3-trifluoroacetone were stirred for 30 min. at 80° C. in a solution of 9.0 g sodium acetate in 250 ml water. Then the solution was cooled at 0° C. and 4.0 g 2-hydrazino-3-fluoro-5-chloropyridin were added. Stirring was continued for 3.5 hrs. Then the reaction mixture was extracted with ethyl acetate, the extracts were washed with water and dried. After evaporation, the remaining residue was purified on silcagel (hexane-ethyl acetate 8:2) to give the title compound as brownish residue which was directly used for the next step. MS: (M−H )=268.

In analogous manner, 3-((6-chloro-5-cyano-3-fluoro-pyridin-2-yl) -hydrazono)-1,1,1-trifluoro-propan-2-one with m.p. 174–176° C. was obtained.

The preferred compounds listed in the following tables can also be obtained in an analogous manner and according to the methods illustrated in the general reaction schemes 1–11 and described in the cited references.

TABLE 1

A preferred group of compounds of formula I corresponds to the general formula

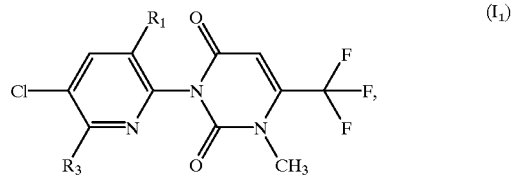

(I$_1$)

wherein substituents R$_1$ and R$_3$ are defined in Table A, constituting the disclosure of 448 specific compounds of formula I$_1$.

TABLE 2

A further preferred group of compounds of formula I corresponds to the general formula

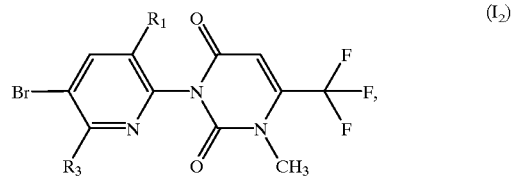

(I$_2$)

wherein substituents R$_1$ and R$_3$ are defined in Table A, constituting the disclosure of 448 specific compounds of formula I$_2$.

TABLE 3

A further preferred group of compounds of
formula I corresponds to the general formula (I₃)

wherein substituents $R_1$ and $R_3$ are defined in Table A, constituting the disclosure of 448 specific compounds of formula $I_3$.

TABLE 4

A further preferred group of compounds of
formula I corresponds to the general formula (I₄)

wherein substituents $R_1$ and $R_3$ are defined in Table A, constituting the disclosure of 448 specific compounds of formula $I_4$.

TABLE 5

A further preferred group of compounds of
formula I corresponds to the general formula (I₅)

wherein substituents $R_1$ and $R_3$ are defined in Table A, constituting the disclosure of 448 specific compounds of formula $I_5$.

TABLE 6

A further preferred group of compounds of
formula I corresponds to the general formula (I₆)

wherein substituents $R_1$ and $R_3$ are defined in Table A, constituting the disclosure of 448 specific compounds of formula $I_6$.

TABLE 7

A further preferred group of compounds of
formula I corresponds to the general formula (I₇)

wherein substituents $R_1$ and $R_3$ are defined in Table A, constituting the disclosure of 448 specific compounds of formula $I_7$.

TABLE 8

A further preferred group of compounds of
formula I corresponds to the general formula (I₈)

wherein substituents $R_1$ and $R_3$ are defined in Table A, constituting the disclosure of 448 specific compounds of formula $I_8$.

TABLE 9

A further preferred group of compounds of
formula I corresponds to the general formula (I₉)

wherein substituents $R_1$ and $R_3$ are defined in Table A, constituting the disclosure of 448 specific compounds of formula $I_9$.

TABLE 10

A further preferred group of compounds of
formula I corresponds to the general formula (I₁₀)

wherein substituents $R_1$ and $R_3$ are defined in Table A, constituting the disclosure of 448 specific compounds of formula $I_{10}$.

TABLE 11

A further preferred group of compounds of formula I corresponds to the general formula

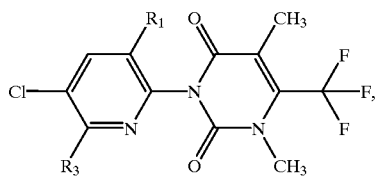
(I₁₁)

wherein substituents R₁ and R₃ are defined in Table A, constituting the disclosure of 448 specific compounds of formula I₁₁.

TABLE 12

A further preferred group of compounds of formula I corresponds to the general formula

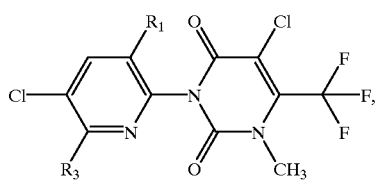
(I₁₂)

wherein substituents R₁ and R₃ are defined in Table A, constituting the disclosure of 448 specific compounds of formula I₁₂.

TABLE 13

A further preferred group of compounds of formula I corresponds to the general formula

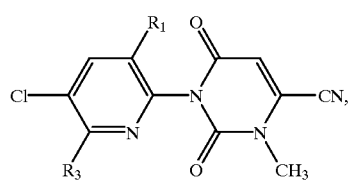
(I₁₃)

wherein substituents R₁ and R₃ are defined in Table A, constituting the disclosure of 448 specific compounds of formula I₁₃.

TABLE 14

A further preferred group of compounds of formula I corresponds to the general formula

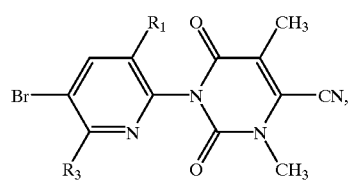
(I₁₄)

wherein substituents R₁ and R₃ are defined in Table A, constituting the disclosure of 448 specific compounds of formula I₁₄.

TABLE 15

A further preferred group of compounds of formula I corresponds to the general formula

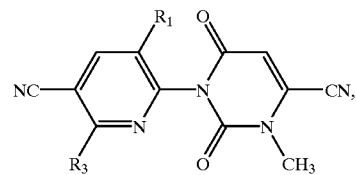
(I₁₅)

wherein substituents R₁ and R₃ are defined in Table A, constituting the disclosure of 448 specific compounds of formula I₁₅.

TABLE 16

A further preferred group of compounds of formula I corresponds to the general formula

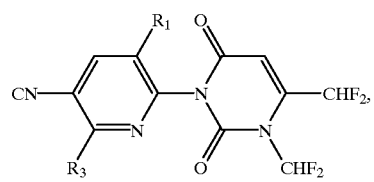
(I₁₆)

wherein substituents R₁ and R₃ are defined in Table A, constituting the disclosure of 448 specific compounds of formula I₁₆.

TABLE 17

A further preferred group of compounds of formula I corresponds to the general formula

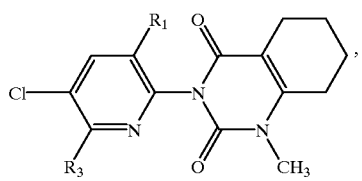
(I₁₇)

wherein substituents R₁ and R₃ are defined in Table A, constituting the disclosure of 448 specific compounds of formula I₁₇.

TABLE 18

A further preferred group of compounds of formula I corresponds to the general formula

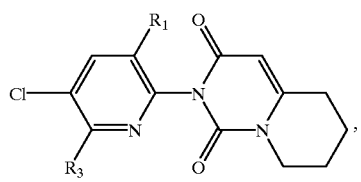
(I₁₈)

wherein substituents R₁ and R₃ are defined in Table A, constituting the disclosure of 448 specific compounds of formula I₁₈.

TABLE 19

A further preferred group of compounds of
formula I corresponds to the general formula

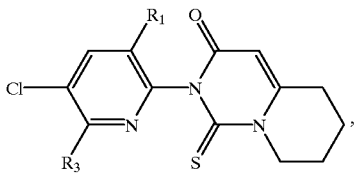
($I_{19}$)

wherein substituents $R_1$ and $R_3$ are defined in Table A, constituting the disclosure of 448 specific compounds of formula $I_{19}$.

TABLE 20

A further preferred group of compounds of
formula I corresponds to the general formula

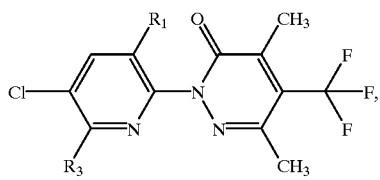
($I_{20}$)

wherein substituents $R_1$ and $R_3$ are defined in Table A, constituting the disclosure of 448 specific compounds of formula $I_{20}$.

TABLE 21

A further preferred group of compounds of
formula I corresponds to the general formula

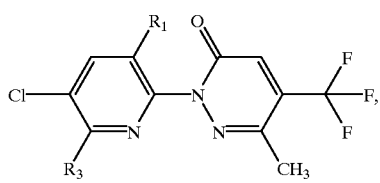
($I_{21}$)

wherein substituents $R_1$ and $R_3$ are defined in Table A, constituting the disclosure of 448 specific compounds of formula $I_{21}$.

TABLE 22

A further preferred group of compounds of
formula I corresponds to the general formula

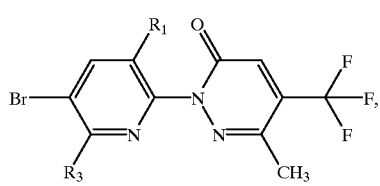
($I_{22}$)

wherein substituents $R_1$ and $R_3$ are defined in Table A, constituting the disclosure of 448 specific compounds of formula $I_{22}$.

TABLE 23

A further preferred group of compounds of
formula I corresponds to the general formula

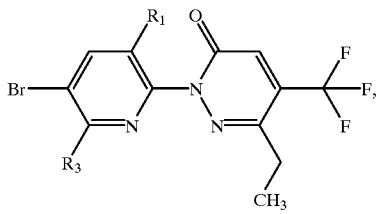
($I_{23}$)

wherein substituents $R_1$ and $R_3$ are defined in Table A, constituting the disclosure of 448 specific compounds of formula $I_{23}$.

TABLE 24

A further preferred group of compounds of
formula I corresponds to the general formula

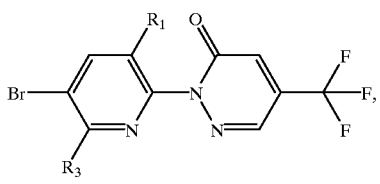
($I_{24}$)

wherein substituents $R_1$ and $R_3$ are defined in Table A, constituting the disclosure of 448 specific compounds of formula $I_{24}$.

TABLE 25

A further preferred group of compounds of
formula I corresponds to the general formula

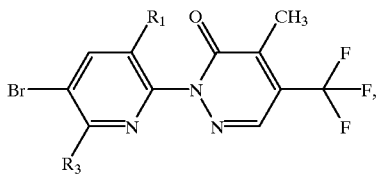
($I_{25}$)

wherein substituents $R_1$ and $R_3$ are defined in Table A, constituting the disclosure of 448 specific compounds of formula $I_{25}$.

TABLE 26

A further preferred group of compounds of
formula I corresponds to the general formula

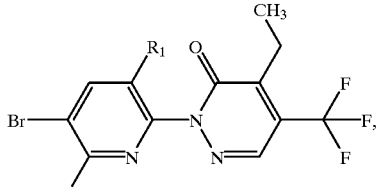
($I_{26}$)

wherein substituents $R_1$ and $R_3$ are defined in Table A, constituting the disclosure of 448 specific compounds of formula $I_{26}$.

TABLE 27

A further preferred group of compounds of
formula I corresponds to the general formula

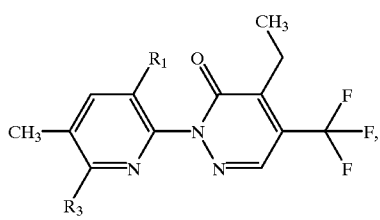
($I_{27}$)

wherein substituents $R_1$ and $R_3$ are defined in Table A, constituting the disclosure of 448 specific compounds of formula $I_{27}$.

TABLE 28

A further preferred group of compounds of
formula I corresponds to the general formula

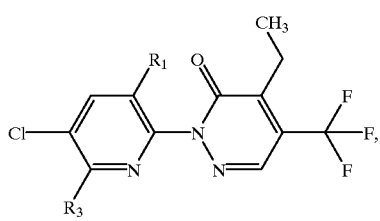
($I_{28}$)

wherein substituents $R_1$ and $R_3$ are defined in Table A, constituting the disclosure of 448 specific compounds of formula $I_{28}$.

TABLE 29

A further preferred group of compounds of
formula I corresponds to the general formula

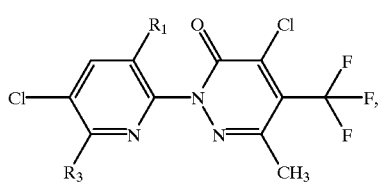
($I_{29}$)

wherein substituents $R_1$ and $R_3$ are defined in Table A, constituting the disclosure of 448 specific compounds of formula $I_{29}$.

TABLE 30

A further preferred group of compounds of
formula I corresponds to the general formula

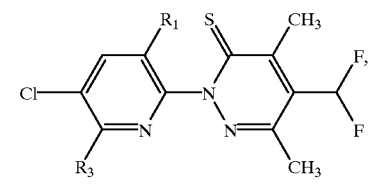
($I_{30}$)

wherein substituents $R_1$ and $R_3$ are defined in Table A, constituting the disclosure of 448 specific compounds of formula $I_{30}$.

TABLE 31

A further preferred group of compounds of
formula I corresponds to the general formula

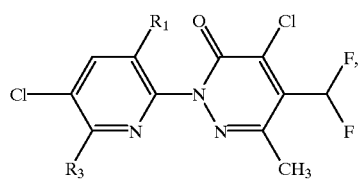
($I_{31}$)

wherein substituents $R_1$ and $R_3$ are defined in Table A, constituting the disclosure of 448 specific compounds of formula $I_{31}$.

TABLE 32

A further preferred group of compounds of
formula I corresponds to the general formula

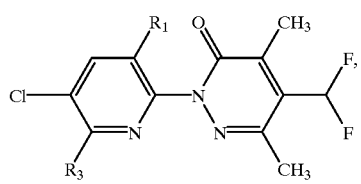
($I_{32}$)

wherein substituents $R_1$ and $R_3$ are defined in Table A, constituting the disclosure of 448 specific compounds of formula $I_{32}$.

TABLE 33

A further preferred group of compounds of
formula I corresponds to the general formula

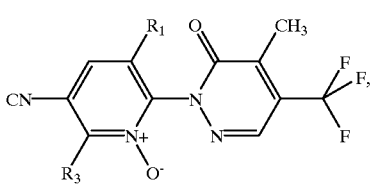
($I_{33}$)

wherein substituents $R_1$ and $R_3$ are defined in Table A, constituting the disclosure of 448 specific compounds of formula $I_{33}$.

TABLE 34

A further preferred group of compounds of
formula I corresponds to the general formula

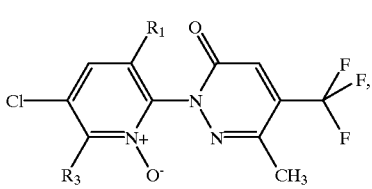
($I_{34}$)

wherein substituents $R_1$ and $R_3$ are defined in Table A, constituting the disclosure of 448 specific compounds of formula $I_{34}$.

TABLE 35

A further preferred group of compounds of
formula I corresponds to the general formula

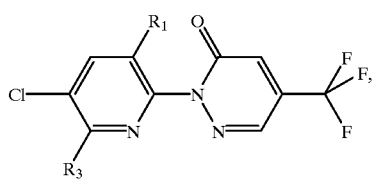 (I$_{35}$)

wherein substituents R$_1$ and R$_3$ are defined in Table A, constituting the disclosure of 448 specific compounds of formula I$_{35}$.

TABLE 36

A further preferred group of compounds of
formula I corresponds to the general formula

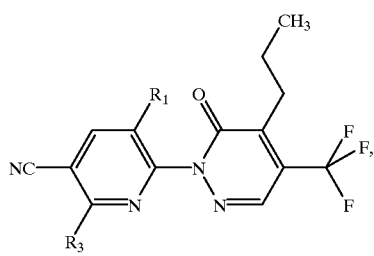 (I$_{36}$)

wherein substituents R$_1$ and R$_3$ are defined in Table A, constituting the disclosure of 448 specific compounds of formula I$_{36}$.

TABLE 37

A further preferred group of compounds of
formula I corresponds to the general formula

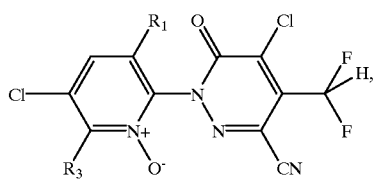 (I$_{37}$)

wherein substituents R$_1$ and R$_3$ are defined in Table A, constituting the disclosure of 448 specific compounds of formula I$_{37}$.

TABLE 38

A further preferred group of compounds of
formula I corresponds to the general formula

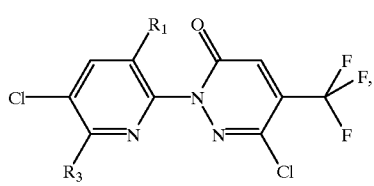 (I$_{38}$)

wherein substituents R$_1$ and R$_3$ are defined in Table A, constituting the disclosure of 448 specific compounds of formula I$_{38}$.

TABLE 39

A further preferred group of compounds of
formula I corresponds to the general formula

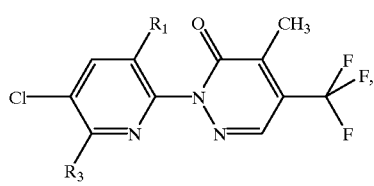 (I$_{39}$)

wherein substituents R$_1$ and R$_3$ are defined in Table A, constituting the disclosure of 448 specific compounds of formula I$_{39}$.

TABLE 40

A further preferred group of compounds of
formula I corresponds to the general formula

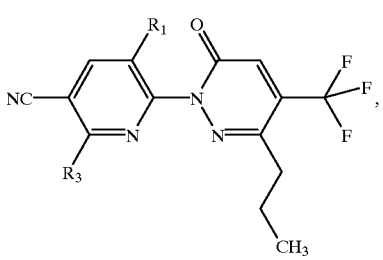 (I$_{40}$)

wherein substituents R$_1$ and R$_3$ are defined in Table A, constituting the disclosure of 448 specific compounds of formula I$_{40}$.

TABLE 41

A further preferred group of compounds of
formula I corresponds to the general formula

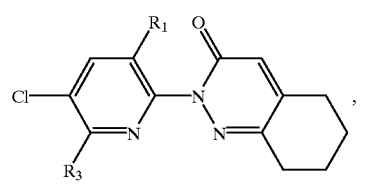 (I$_{41}$)

wherein substituents R$_1$ and R$_3$ are defined in Table A, constituting the disclosure of 448 specific compounds of formula I$_{41}$.

TABLE 42

A further preferred group of compounds of
formula I corresponds to the general formula

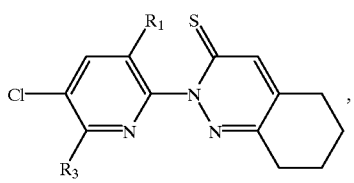 (I$_{42}$)

wherein substituents R$_1$ and R$_3$ are defined in Table A, constituting the disclosure of 448 specific compounds of formula I$_{42}$.

TABLE 43

A further preferred group of compounds of
formula I corresponds to the general formula

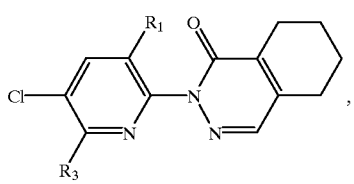 (I$_{43}$)

wherein substituents R$_1$ and R$_3$ are defined in Table A, constituting the disclosure of 448 specific compounds of formula I$_{43}$.

TABLE 44

A further preferred group of compounds of
formula I corresponds to the general formula

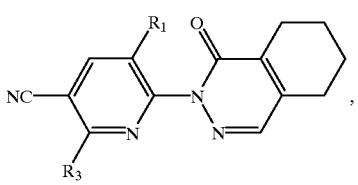 (I$_{44}$)

wherein substituents R$_1$ and R$_3$ are defined in Table A, constituting the disclosure of 448 specific compounds of formula I$_{44}$.

TABLE 45

A further preferred group of compounds of
formula I corresponds to the general formula

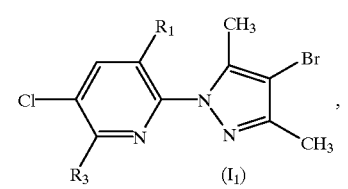 (I$_{45}$)

wherein substituents R$_1$ and R$_3$ are defined in Table A, constituting the disclosure of 448 specific compounds of formula I$_{45}$.

TABLE 46

A further preferred group of compounds of
formula I corresponds to the general formula

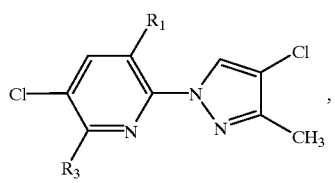 (I$_{46}$)

wherein substituents R$_1$ and R$_3$ are defined in Table A, constituting the disclosure of 448 specific compounds of formula I$_{46}$.

TABLE 47

A further preferred group of compounds of
formula I corresponds to the general formula

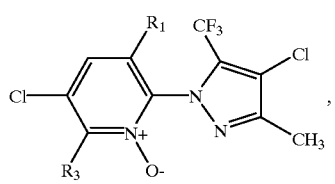 (I$_{47}$)

wherein substituents R$_1$ and R$_3$ are defined in Table A, constituting the disclosure of 448 specific compounds of formula I$_{47}$.

TABLE 48

A further preferred group of compounds of
formula I corresponds to the general formula

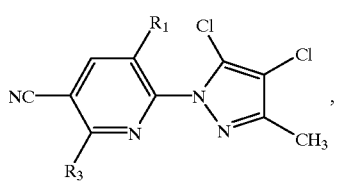 (I$_{48}$)

wherein substituents R$_1$ and R$_3$ are defined in Table A, constituting the disclosure of 448 specific compounds of formula I$_{48}$.

TABLE 49

A further preferred group of compounds of
formula I corresponds to the general formula

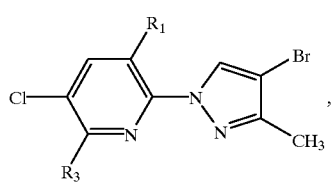 (I$_{49}$)

wherein substituents R$_1$ and R$_3$ are defined in Table A, constituting the disclosure of 448 specific compounds of formula I$_{49}$.

TABLE 50

A further preferred group of compounds of
formula I corresponds to the general formula

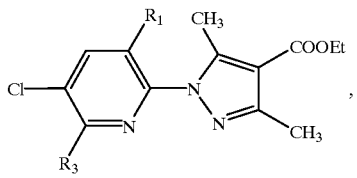

($I_{50}$)

wherein substituents $R_1$ and $R_3$ are defined in Table A, constituting the disclosure of 448 specific compounds of formula $I_{50}$.

TABLE 51

A further preferred group of compounds of
formula I corresponds to the general formula

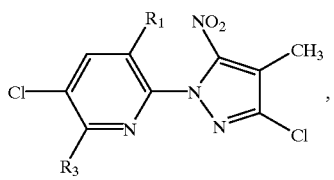

($I_{51}$)

wherein substituents $R_1$ and $R_3$ are defined in Table A, constituting the disclosure of 448 specific compounds of formula $I_{51}$.

TABLE 52

A further preferred group of compounds of
formula I corresponds to the general formula

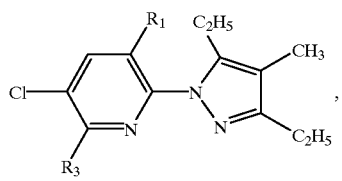

($I_{52}$)

wherein substituents $R_1$ and $R_3$ are defined in Table A, constituting the disclosure of 448 specific compounds of formula $I_{52}$.

TABLE 53

A further preferred group of compounds of
formula I corresponds to the general formula

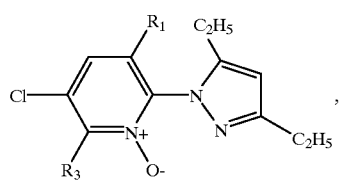

($I_{53}$)

wherein substituents $R_1$ and $R_3$ are defined in Table A, constituting the disclosure of 448 specific compounds of formula $I_{53}$.

TABLE 54

A further preferred group of compounds of
formula I corresponds to the general formula

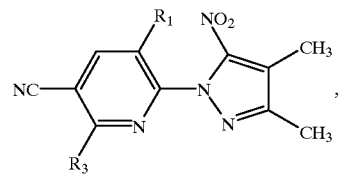

($I_{54}$)

wherein substituents $R_1$ and $R_3$ are defined in Table A, constituting the disclosure of 448 specific compounds of formula $I_{54}$.

TABLE 55

A further preferred group of compounds of
formula I corresponds to the general formula

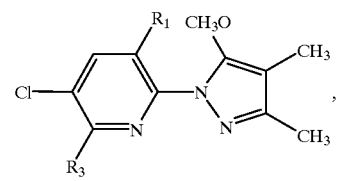

($I_{55}$)

wherein substituents $R_1$ and $R_3$ are defined in Table A, constituting the disclosure of 448 specific compounds of formula $I_{55}$.

TABLE 56

A further preferred group of compounds of
formula I corresponds to the general formula

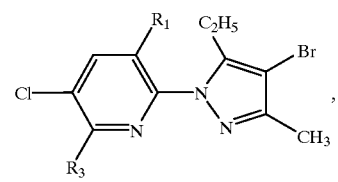

($I_{56}$)

wherein substituents $R_1$ and $R_3$ are defined in Table A, constituting the disclosure of 448 specific compounds of formula $I_{56}$.

TABLE 57

A further preferred group of compounds of
formula I corresponds to the general formula

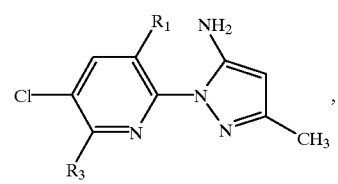

($I_{57}$)

wherein substituents $R_1$ and $R_3$ are defined in Table A, constituting the disclosure of 448 specific compounds of formula $I_{57}$.

TABLE 58

A further preferred group of compounds of
formula I corresponds to the general formula

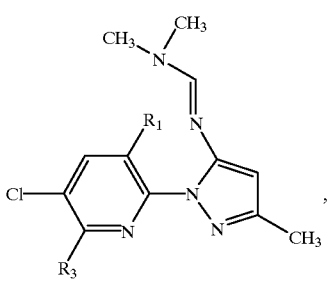

($I_{58}$)

wherein substituents $R_1$ and $R_3$ are defined in Table A, constituting the disclosure of 448 specific compounds of formula $I_{58}$.

TABLE 59

A further preferred group of compounds of
formula I corresponds to the general formula ($I_{59}$)

wherein substituents $R_1$ and $R_3$ are defined in Table A, constituting the disclosure of 448 specific compounds of formula $I_{59}$.

TABLE 60

A further preferred group of compounds of
formula I corresponds to the general formula

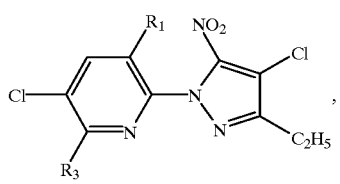

($I_{60}$)

wherein substituents $R_1$ and $R_3$ are defined in Table A, constituting the disclosure of 448 specific compounds of formula $I_{60}$.

TABLE 61

A further preferred group of compounds of
formula I corresponds to the general formula

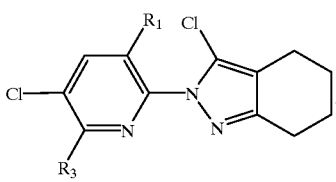

($I_{61}$)

wherein substituents $R_1$ and $R_3$ are defined in Table A, constituting the disclosure of 448 specific compounds of formula $I_{61}$.

TABLE 62

A further preferred group of compounds of
formula I corresponds to the general formula

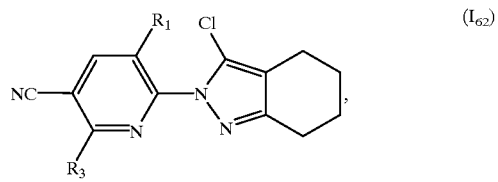

($I_{62}$)

wherein substituents $R_1$ and $R_3$ are defined in Table A, constituting the disclosure of 448 specific compounds of formula $I_{62}$.

TABLE 63

A further preferred group of compounds of
formula I corresponds to the general formula

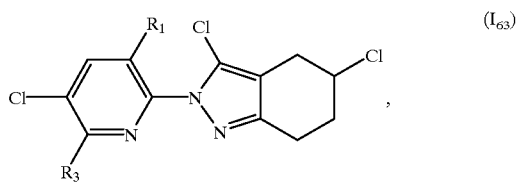

($I_{63}$)

wherein substituents $R_1$ and $R_3$ are defined in Table A, constituting the disclosure of 448 specific compounds of formula $I_{63}$.

TABLE 64

A further preferred group of compounds of
formula I corresponds to the general formula

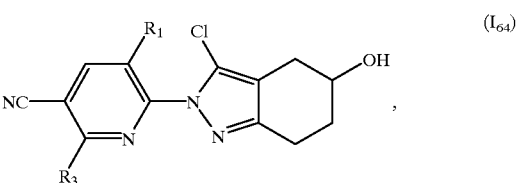

($I_{64}$)

wherein substituents $R_1$ and $R_3$ are defined in Table A, constituting the disclosure of 448 specific compounds of formula $I_{64}$.

TABLE 65

A further preferred group of compounds of
formula I corresponds to the general formula

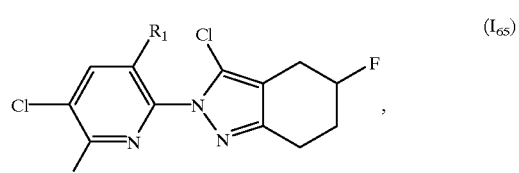

($I_{65}$)

wherein substituents $R_1$ and $R_3$ are defined in Table A, constituting the disclosure of 448 specific compounds of formula $I_{65}$.

TABLE 66

A further preferred group of compounds of
formula I corresponds to the general formula

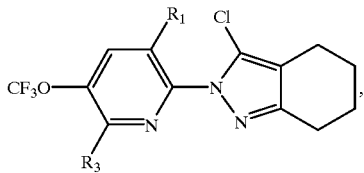
(I₆₆)

wherein substituents $R_1$ and $R_3$ are defined in Table A, constituting the disclosure of 448 specific compounds of formula $I_{66}$.

TABLE 67

A further preferred group of compounds of
formula I corresponds to the general formula

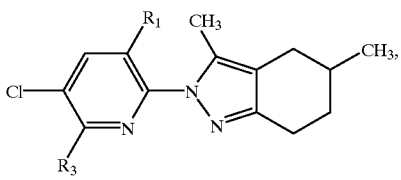
(I₆₇)

wherein substituents $R_1$ and $R_3$ are defined in Table A, constituting the disclosure of 448 specific compounds of formula $I_{67}$.

TABLE 68

A further preferred group of compounds of
formula I corresponds to the general formula

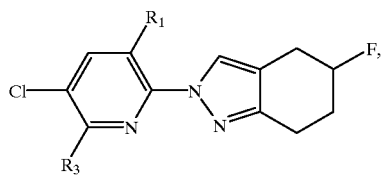
(I₆₈)

wherein substituents $R_1$ and $R_3$ are defined in Table A, constituting the disclosure of 448 specific compounds of formula $I_{68}$.

TABLE 69

A further preferred group of compounds of
formula I corresponds to the general formula

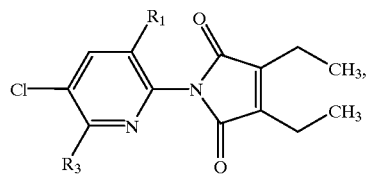
(I₆₉)

wherein substituents $R_1$ and $R_3$ are defined in Table A, constituting the disclosure of 448 specific compounds of formula $I_{69}$.

TABLE 70

A further preferred group of compounds of
formula I corresponds to the general formula

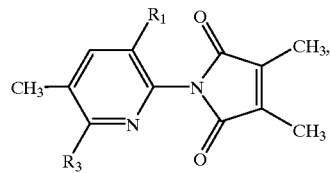
(I₇₀)

wherein substituents $R_1$ and $R_3$ are defined in Table A, constituting the disclosure of 448 specific compounds of formula $I_{70}$.

TABLE 71

A further preferred group of compounds of
formula I corresponds to the general formula

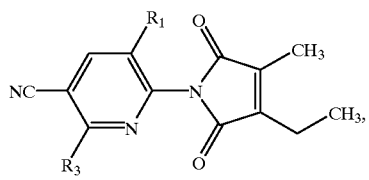
(I₇₁)

wherein substituents $R_1$ and $R_3$ are defined in Table A, constituting the disclosure of 448 specific compounds of formula $I_{71}$.

TABLE 72

A further preferred group of compounds of
formula I corresponds to the general formula

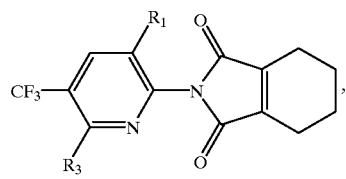
(I₇₂)

wherein substituents $R_1$ and $R_3$ are defined in Table A, constituting the disclosure of 448 specific compounds of formula $I_{72}$.

TABLE 73

A further preferred group of compounds of
formula I corresponds to the general formula

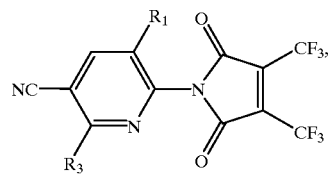
(I₇₃)

wherein substituents $R_1$ and $R_3$ are defined in Table A, constituting the disclosure of 448 specific compounds of formula $I_{73}$.

TABLE 74

A further preferred group of compounds of
formula I corresponds to the general formula

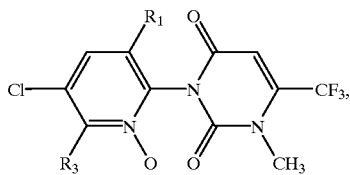
(I$_{74}$)

wherein substituents R$_1$ and R$_3$ are defined in Table A, constituting the disclosure of 448 specific compounds of formula I$_{74}$.

TABLE 75

A further preferred group of compounds of
formula I corresponds to the general formula

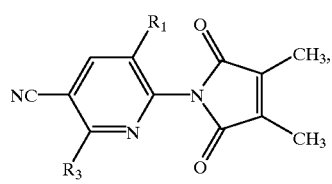
(I$_{75}$)

wherein substituents R$_1$ and R$_3$ are defined in Table A, constituting the disclosure of 448 specific compounds of formula I$_{75}$.

TABLE 76

A further preferred group of compounds of
formula I corresponds to the general formula

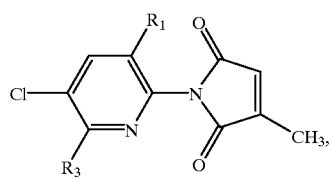
(I$_{76}$)

wherein substituents R$_1$ and R$_3$ are defined in Table A, constituting the disclosure of 448 specific compounds of formula I$_{76}$.

TABLE 77

A further preferred group of compounds of
formula I corresponds to the general formula

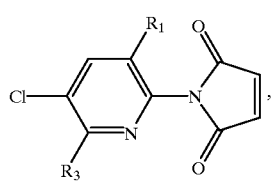
(I$_{77}$)

wherein substituents R$_1$ and R$_3$ are defined in Table A, constituting the disclosure of 448 specific compounds of formula I$_{77}$.

TABLE 78

A further preferred group of compounds of
formula I corresponds to the general formula

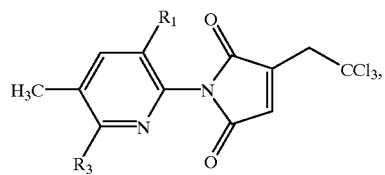
(I$_{78}$)

wherein substituents R$_1$ and R$_3$ are defined in Table A, constituting the disclosure of 448 specific compounds of formula I$_{78}$.

TABLE 79

A further preferred group of compounds of
formula I corresponds to the general formula

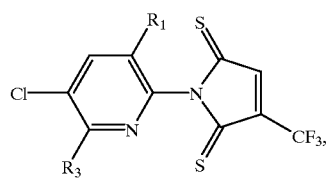
(I$_{79}$)

wherein substituents R$_1$ and R$_3$ are defined in Table A, constituting the disclosure of 448 specific compounds of formula I$_{79}$.

TABLE 80

A further preferred group of compounds of
formula I corresponds to the general formula

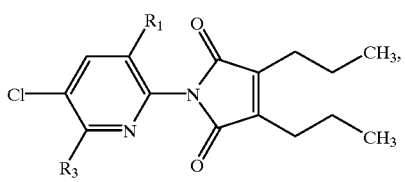
(I$_{80}$)

wherein substituents R$_1$ and R$_3$ are defined in Table A, constituting the disclosure of 448 specific compounds of formula I$_{80}$.

TABLE 81

A further preferred group of compounds of
formula I corresponds to the general formula

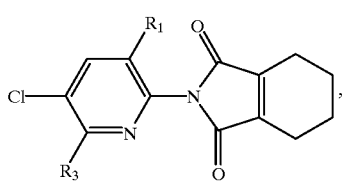
(I$_{81}$)

wherein substituents R$_1$ and R$_3$ are defined in Table A, constituting the disclosure of 448 specific compounds of formula I$_{81}$.

TABLE 82

A further preferred group of compounds of
formula I corresponds to the general formula

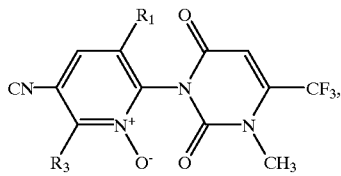 (I$_{82}$)

wherein substituents R$_1$ and R$_3$ are defined in Table A, constituting the disclosure of 448 specific compounds of formula I$_{82}$.

TABLE 83

A further preferred group of compounds of
formula I corresponds to the general formula

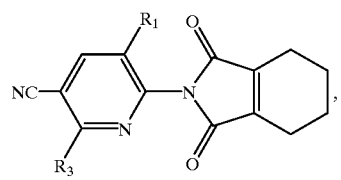 (I$_{83}$)

wherein substituents R$_1$ and R$_3$ are defined in Table A, constituting the disclosure of 448 specific compounds of formula I$_{83}$.

TABLE 84

A further preferred group of compounds of
formula I corresponds to the general formula

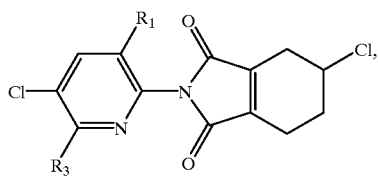 (I$_{84}$)

wherein substituents R$_1$ and R$_3$ are defined in Table A, constituting the disclosure of 448 specific compounds of formula I$_{84}$.

TABLE 85

A further preferred group of compounds of
formula I corresponds to the general formula

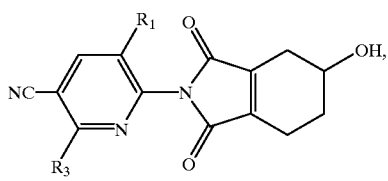 (I$_{85}$)

wherein substituents R$_1$ and R$_3$ are defined in Table A, constituting the disclosure of 448 specific compounds of formula I$_{85}$.

TABLE 86

A further preferred group of compounds of
formula I corresponds to the general formula

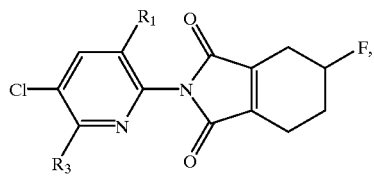 (I$_{86}$)

wherein substituents R$_1$ and R$_3$ are defined in Table A, constituting the disclosure of 448 specific compounds of formula I$_{86}$.

TABLE 87

A further preferred group of compounds of
formula I corresponds to the general formula

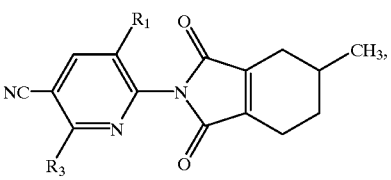 (I$_{87}$)

wherein substituents R$_1$ and R$_3$ are defined in Table A, constituting the disclosure of 448 specific compounds of formula I$_{87}$.

TABLE 88

A further preferred group of compounds of
formula I corresponds to the general formula

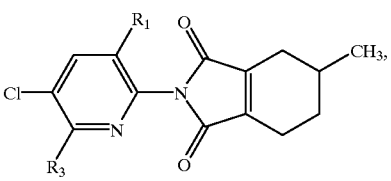 (I$_{88}$)

wherein substituents R$_1$ and R$_3$ are defined in Table A, constituting the disclosure of 448 specific compounds of formula I$_{88}$.

TABLE 89

A further preferred group of compounds of
formula I corresponds to the general formula

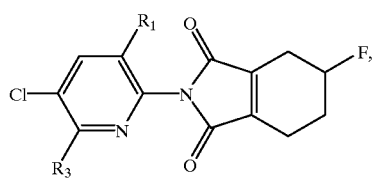 (I$_{89}$)

wherein substituents R$_1$ and R$_3$ are defined in Table A, constituting the disclosure of 448 specific compounds of formula I$_{89}$.

TABLE 90

A further preferred group of compounds of
formula I corresponds to the general formula

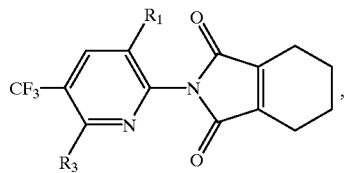
($I_{90}$)

wherein substituents $R_1$ and $R_3$ are defined in Table A, constituting the disclosure of 448 specific compounds of formula $I_{90}$.

TABLE 91

A further preferred group of compounds of
formula I corresponds to the general formula

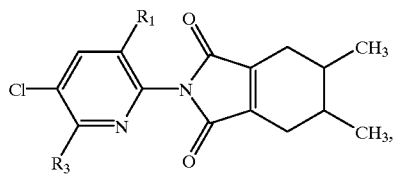
($I_{91}$)

wherein substituents $R_1$ and $R_3$ are defined in Table A, constituting the disclosure of 448 specific compounds of formula $I_{91}$.

TABLE 92

A further preferred group of compounds of
formula I corresponds to the general formula

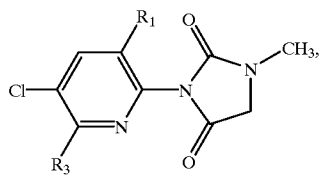
($I_{92}$)

wherein substituents $R_1$ and $R_3$ are defined in Table A, constituting the disclosure of 448 specific compounds of formula $I_{92}$.

TABLE 93

A further preferred group of compounds of
formula I corresponds to the general formula

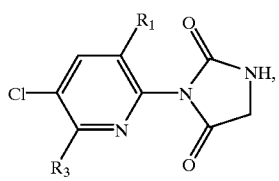
($I_{93}$)

wherein substituents $R_1$ and $R_3$ are defined in Table A, constituting the disclosure of 448 specific compounds of formula $I_{93}$.

TABLE 94

A further preferred group of compounds of
formula I corresponds to the general formula

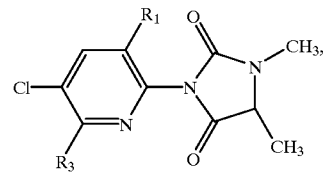
($I_{94}$)

wherein substituents $R_1$ and $R_3$ are defined in Table A, constituting the disclosure of 448 specific compounds of formula $I_{94}$.

TABLE 95

A further preferred group of compounds of
formula I corresponds to the general formula

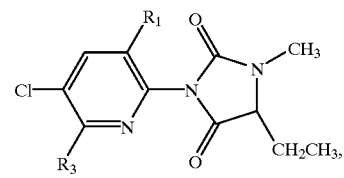
($I_{95}$)

wherein substituents $R_1$ and $R_3$ are defined in Table A, constituting the disclosure of 448 specific compounds of formula $I_{95}$.

TABLE 96

A further preferred group of compounds of
formula I corresponds to the general formula

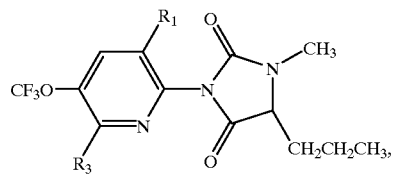
($I_{96}$)

wherein substituents $R_1$ and $R_3$ are defined in Table A, constituting the disclosure of 448 specific compounds of formula $I_{96}$.

TABLE 97

A further preferred group of compounds of
formula I corresponds to the general formula

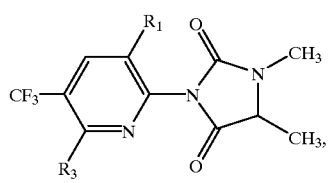
($I_{97}$)

wherein substituents $R_1$ and $R_3$ are defined in Table A, constituting the disclosure of 448 specific compounds of formula $I_{97}$.

TABLE 98

A further preferred group of compounds of
formula I corresponds to the general formula

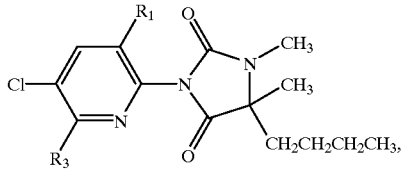
($I_{98}$)

wherein substituents $R_1$ and $R_3$ are defined in Table A, constituting the disclosure of 448 specific compounds of formula $I_{98}$.

TABLE 99

A further preferred group of compounds of
formula I corresponds to the general formula

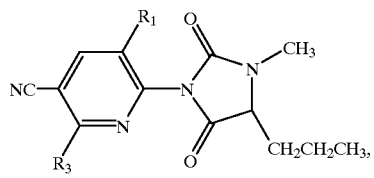
($I_{99}$)

wherein substituents $R_1$ and $R_3$ are defined in Table A, constituting the disclosure of 448 specific compounds of formula $I_{99}$.

TABLE 100

A further preferred group of compounds of
formula I corresponds to the general formula

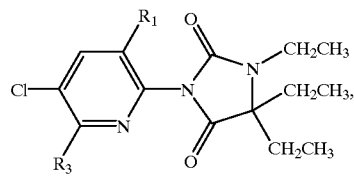
($I_{100}$)

wherein substituents $R_1$ and $R_3$ are defined in Table A, constituting the disclosure of 448 specific compounds of formula $I_{100}$.

TABLE 101

A further preferred group of compounds of
formula I corresponds to the general formula

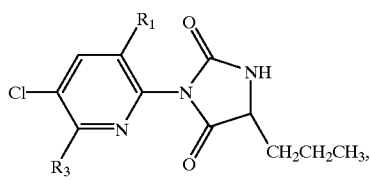
($I_{101}$)

wherein substituents $R_1$ and $R_3$ are defined in Table A, constituting the disclosure of 448 specific compounds of formula $I_{101}$.

TABLE 102

A further preferred group of compounds of
formula I corresponds to the general formula

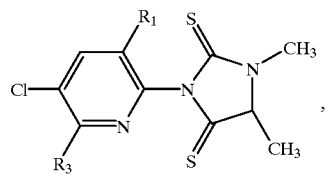
($I_{102}$)

wherein substituents $R_1$ and $R_3$ are defined in Table A, constituting the disclosure of 448 specific compounds of formula $I_{102}$.

TABLE 103

A further preferred group of compounds of
formula I corresponds to the general formula

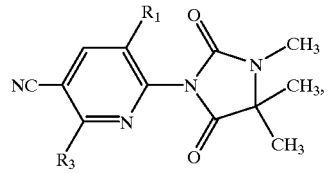
($I_{103}$)

wherein substituents $R_1$ and $R_3$ are defined in Table A, constituting the disclosure of 448 specific compounds of formula $I_{103}$.

TABLE 104

A further preferred group of compounds of
formula I corresponds to the general formula

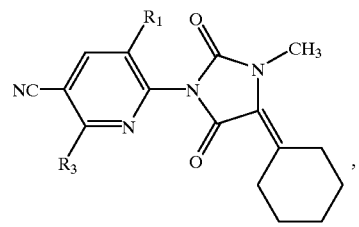
($I_{104}$)

wherein substituents $R_1$ and $R_3$ are defined in Table A, constituting the disclosure of 448 specific compounds of formula $I_{104}$.

TABLE 105

A further preferred group of compounds of
formula I corresponds to the general formula

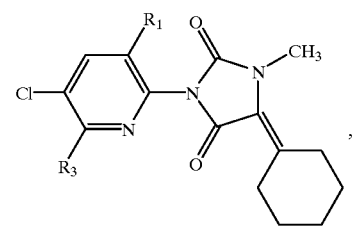
($I_{105}$)

TABLE 106

A further preferred group of compounds of
formula I corresponds to the general formula

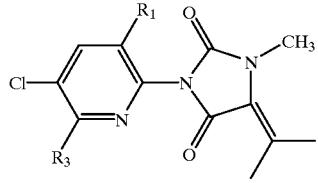 (I$_{106}$)

wherein substituents R$_1$ and R$_3$ are defined in Table A, constituting the disclosure of 448 specific compounds of formula I$_{106}$.

TABLE 107

A further preferred group of compounds of
formula I corresponds to the general formula

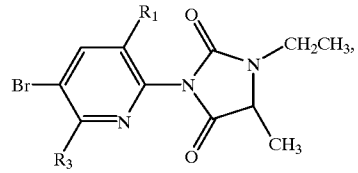 (I$_{107}$)

wherein substituents R$_1$ and R$_3$ are defined in Table A, constituting the disclosure of 448 specific compounds of formula I$_{107}$.

TABLE 108

A further preferred group of compounds of
formula I corresponds to the general formula

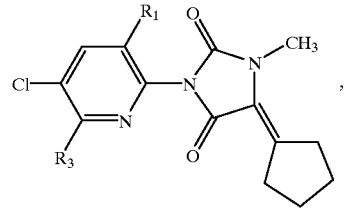 (I$_{108}$)

wherein substituents R$_1$ and R$_3$ are defined in Table A, constituting the disclosure of 448 specific compounds of formula I$_{108}$.

TABLE 109

A further preferred group of compounds of
formula I corresponds to the general formula

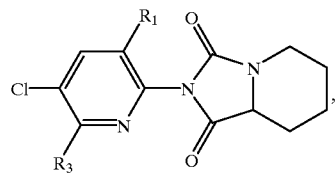 (I$_{109}$)

wherein substituents R$_1$ and R$_3$ are defined in Table A, constituting the disclosure of 448 specific compounds of formula I$_{109}$.

TABLE 110

A further preferred group of compounds of
formula I corresponds to the general formula

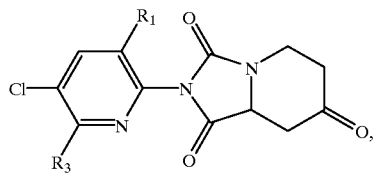 (I$_{110}$)

wherein substituents R$_1$ and R$_3$ are defined in Table A, constituting the disclosure of 448 specific compounds of formula I$_{110}$.

TABLE 111

A further preferred group of compounds of
formula I corresponds to the general formula

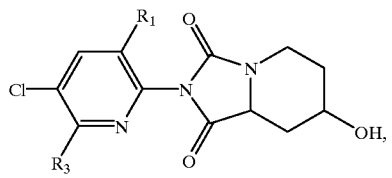 (I$_{111}$)

wherein substituents R$_1$ and R$_3$ are defined in Table A, constituting the disclosure of 448 specific compounds of formula I$_{111}$.

TABLE 112

A further preferred group of compounds of
formula I corresponds to the general formula

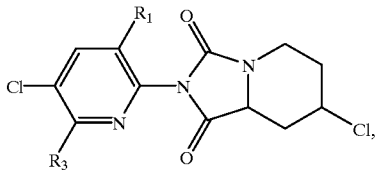 (I$_{112}$)

wherein substituents R$_1$ and R$_3$ are defined in Table A, constituting the disclosure of 448 specific compounds of formula I$_{112}$.

TABLE 113

A further preferred group of compounds of
formula I corresponds to the general formula

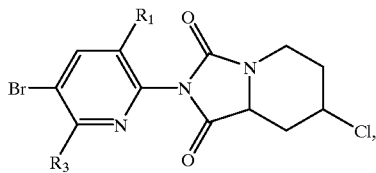
($I_{113}$)

wherein substituents $R_1$ and $R_3$ are defined in Table A, constituting the disclosure of 448 specific compounds of formula $I_{113}$.

TABLE 114

A further preferred group of compounds of
formula I corresponds to the general formula

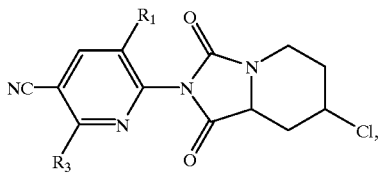
($I_{114}$)

wherein substituents $R_1$ and $R_3$ are defined in Table A, constituting the disclosure of 448 specific compounds of formula $I_{114}$.

TABLE 115

A further preferred group of compounds of
formula I corresponds to the general formula

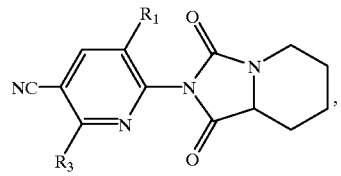
($I_{115}$)

wherein substituents $R_1$ and $R_3$ are defined in Table A, constituting the disclosure of 448 specific compounds of formula $I_{115}$.

TABLE 116

A further preferred group of compounds of
formula I corresponds to the general formula

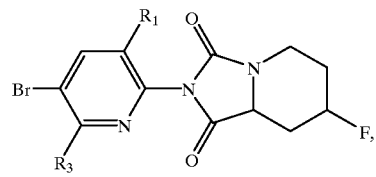
($I_{116}$)

wherein substituents $R_1$ and $R_3$ are defined in Table A, constituting the disclosure of 448 specific compounds of formula $I_{116}$.

TABLE 117

A further preferred group of compounds of
formula I corresponds to the general formula

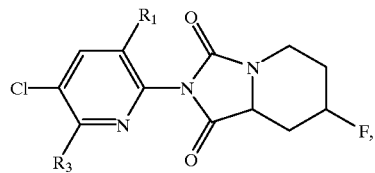
($I_{117}$)

wherein substituents $R_1$ and $R_3$ are defined in Table A, constituting the disclosure of 448 specific compounds of formula $I_{117}$.

TABLE 118

A further preferred group of compounds of
formula I corresponds to the general formula

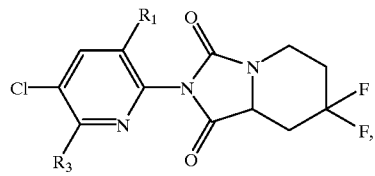
($I_{118}$)

wherein substituents $R_1$ and $R_3$ are defined in Table A, constituting the disclosure of 448 specific compounds of formula $I_{118}$.

TABLE 119

A further preferred group of compounds of
formula I corresponds to the general formula

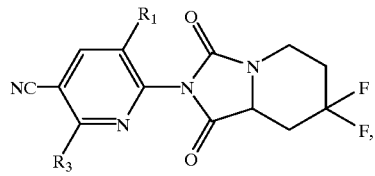
($I_{119}$)

wherein substituents $R_1$ and $R_3$ are defined in Table A, constituting the disclosure of 448 specific compounds of formula $I_{119}$.

TABLE 120

A further preferred group of compounds of
formula I corresponds to the general formula

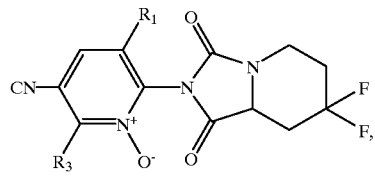
($I_{120}$)

wherein substituents $R_1$ and $R_3$ are defined in Table A, constituting the disclosure of 448 specific compounds of formula $I_{120}$.

TABLE 121

A further preferred group of compounds of
formula I corresponds to the general formula

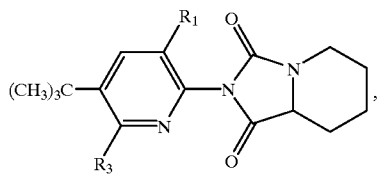
(I₁₂₁)

wherein substituents $R_1$ and $R_3$ are defined in Table A, constituting the disclosure of 448 specific compounds of formula $I_{121}$.

TABLE 122

A further preferred group of compounds of
formula I corresponds to the general formula

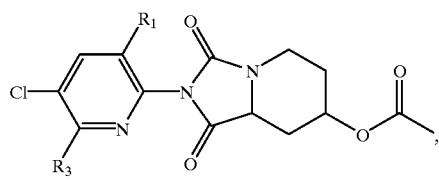
(I₁₂₂)

wherein substituents $R_1$ and $R_3$ are defined in Table A, constituting the disclosure of 448 specific compounds of formula $I_{122}$.

TABLE 123

A further preferred group of compounds of
formula I corresponds to the general formula

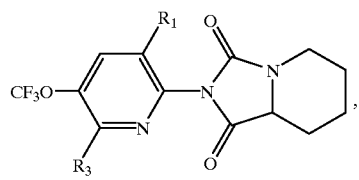
(I₁₂₃)

wherein substituents $R_1$ and $R_3$ are defined in Table A, constituting the disclosure of 448 specific compounds of formula $I_{123}$.

TABLE 124

A further preferred group of compounds of
formula I corresponds to the general formula

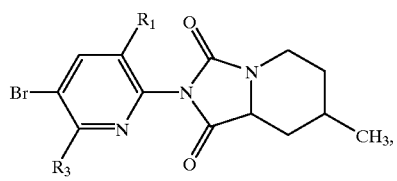
(I₁₂₄)

wherein substituents $R_1$ and $R_3$ are defined in Table A, constituting the disclosure of 448 specific compounds of formula $I_{124}$.

TABLE 125

A further preferred group of compounds of
formula I corresponds to the general formula

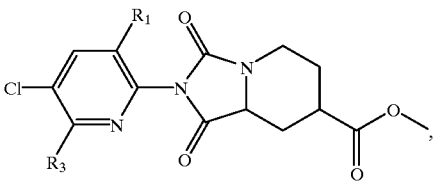
(I₁₂₅)

wherein substituents $R_1$ and $R_3$ are defined in Table A, constituting the disclosure of 448 specific compounds of formula $I_{125}$.

TABLE 126

A further preferred group of compounds of
formula I corresponds to the general formula

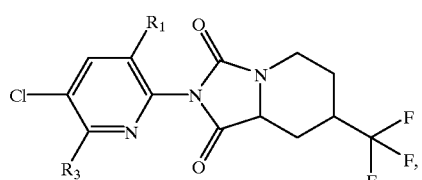
(I₁₂₆)

wherein substituents $R_1$ and $R_3$ are defined in Table A, constituting the disclosure of 448 specific compounds of formula $I_{126}$.

TABLE 127

A further preferred group of compounds of
formula I corresponds to the general formula

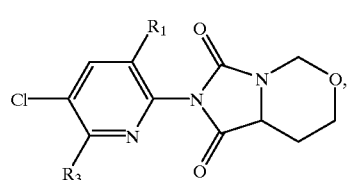
(I₁₂₇)

wherein substituents $R_1$ and $R_3$ are defined in Table A, constituting the disclosure of 448 specific compounds of formula $I_{127}$.

TABLE 128

A further preferred group of compounds of
formula I corresponds to the general formula

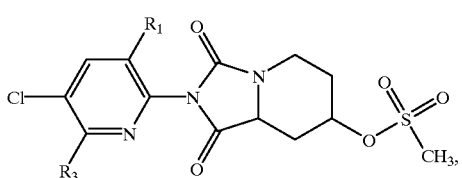
(I₁₂₈)

wherein substituents $R_1$ and $R_3$ are defined in Table A, constituting the disclosure of 448 specific compounds of formula $I_{128}$.

TABLE 129

A further preferred group of compounds of
formula I corresponds to the general formula

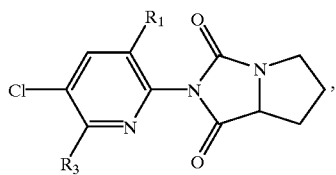
(I$_{129}$)

wherein substituents $R_1$ and $R_3$ are defined in Table A, constituting the disclosure of 448 specific compounds of formula I$_{129}$.

TABLE 130

A further preferred group of compounds of
formula I corresponds to the general formula

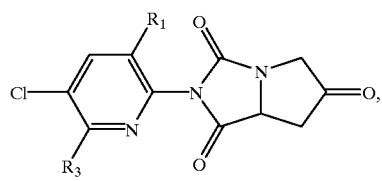
(I$_{130}$)

wherein substituents $R_1$ and $R_3$ are defined in Table A, constituting the disclosure of 448 specific compounds of formula I$_{130}$.

TABLE 131

A further preferred group of compounds of
formula I corresponds to the general formula

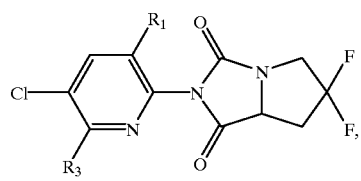
(I$_{131}$)

wherein substituents $R_1$ and $R_3$ are defined in Table A, constituting the disclosure of 448 specific compounds of formula I$_{131}$.

TABLE 132

A further preferred group of compounds of
formula I corresponds to the general formula

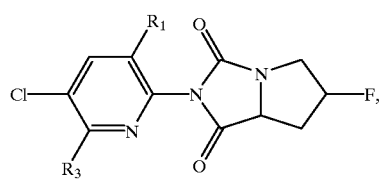
(I$_{132}$)

wherein substituents $R_1$ and $R_3$ are defined in Table A, constituting the disclosure of 448 specific compounds of formula I$_{132}$.

TABLE 133

A further preferred group of compounds of
formula I corresponds to the general formula

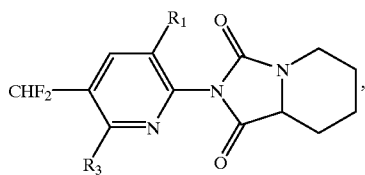
(I$_{133}$)

wherein substituents $R_1$ and $R_3$ are defined in Table A, constituting the disclosure of 448 specific compounds of formula I$_{133}$.

TABLE 134

A further preferred group of compounds of
formula I corresponds to the general formula

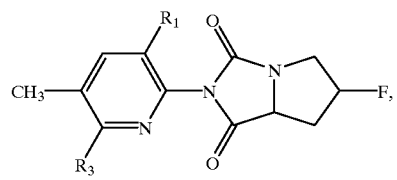
(I$_{134}$)

wherein substituents $R_1$ and $R_3$ are defined in Table A, constituting the disclosure of 448 specific compounds of formula I$_{134}$.

TABLE 135

A further preferred group of compounds of
formula I corresponds to the general formula

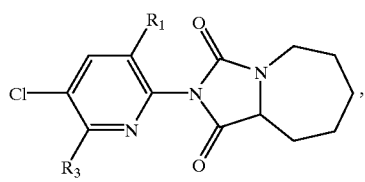
(I$_{135}$)

wherein substituents $R_1$ and $R_3$ are defined in Table A, constituting the disclosure of 448 specific compounds of formula I$_{135}$.

TABLE 136

A further preferred group of compounds of
formula I corresponds to the general formula

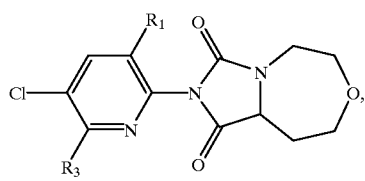
(I$_{136}$)

wherein substituents $R_1$ and $R_3$ are defined in Table A, constituting the disclosure of 448 specific compounds of formula I$_{136}$.

TABLE 137

A further preferred group of compounds of
formula I corresponds to the general formula

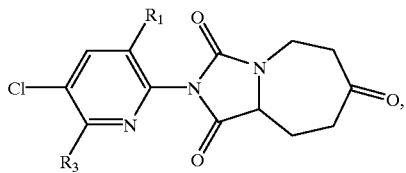

(I$_{137}$)

wherein substituents $R_1$ and $R_3$ are defined in Table A, constituting the disclosure of 448 specific compounds of formula I$_{137}$.

TABLE 138

A further preferred group of compounds of
formula I corresponds to the general formula

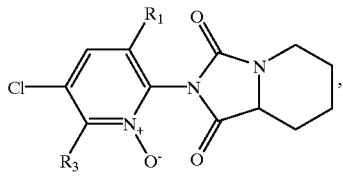

(I$_{138}$)

wherein substituents $R_1$ and $R_3$ are defined in Table A, constituting the disclosure of 448 specific compounds of formula I$_{138}$.

TABLE 139

A further preferred group of compounds of
formula I corresponds to the general formula

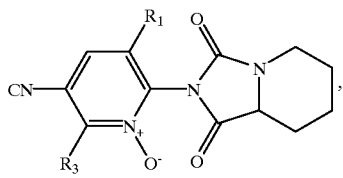

(I$_{139}$)

wherein substituents $R_1$ and $R_3$ are defined in Table A, constituting the disclosure of 448 specific compounds of formula I$_{139}$.

TABLE 140

A further preferred group of compounds of
formula I corresponds to the general formula

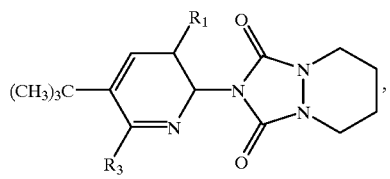

(I$_{140}$)

wherein substituents $R_1$ and $R_3$ are defined in Table A, constituting the disclosure of 448 specific compounds of formula I$_{140}$.

TABLE 141

A further preferred group of compounds of
formula I corresponds to the general formula

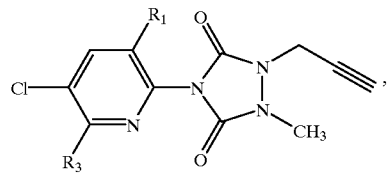

(I$_{141}$)

wherein substituents $R_1$ and $R_3$ are defined in Table A, constituting the disclosure of 448 specific compounds of formula I$_{141}$.

TABLE 142

A further preferred group of compounds of
formula I corresponds to the general formula

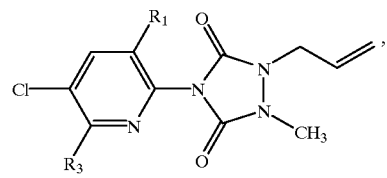

(I$_{142}$)

wherein substituents $R_1$ and $R_3$ are defined in Table A, constituting the disclosure of 448 specific compounds of formula I$_{142}$.

TABLE 143

A further preferred group of compounds of
formula I corresponds to the general formula

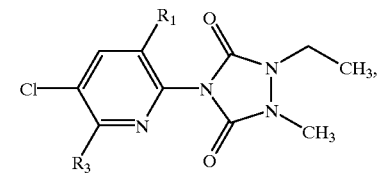

(I$_{143}$)

wherein substituents $R_1$ and $R_3$ are defined in Table A, constituting the disclosure of 448 specific compounds of formula I$_{143}$.

TABLE 144

A further preferred group of compounds of
formula I corresponds to the general formula

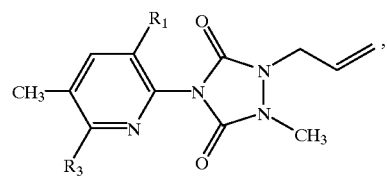

(I$_{144}$)

wherein substituents $R_1$ and $R_3$ are defined in Table A, constituting the disclosure of 448 specific compounds of formula I$_{144}$.

TABLE 145

A further preferred group of compounds of formula I corresponds to the general formula

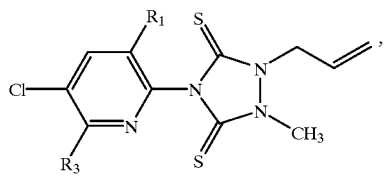 (I₁₄₅)

wherein substituents $R_1$ and $R_3$ are defined in Table A, constituting the disclosure of 448 specific compounds of formula $I_{145}$.

TABLE 146

A further preferred group of compounds of formula I corresponds to the general formula

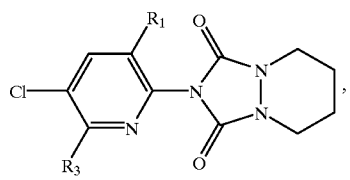 (I₁₄₆)

wherein substituents $R_1$ and $R_3$ are defined in Table A, constituting the disclosure of 448 specific compounds of formula $I_{146}$.

TABLE 147

A further preferred group of compounds of formula I corresponds to the general formula

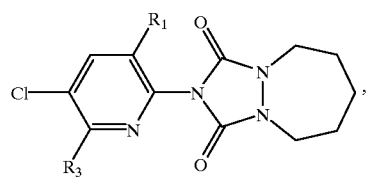 (I₁₄₇)

wherein substituents $R_1$ and $R_3$ are defined in Table A, constituting the disclosure of 448 specific compounds of formula $I_{147}$.

TABLE 148

A further preferred group of compounds of formula I corresponds to the general formula

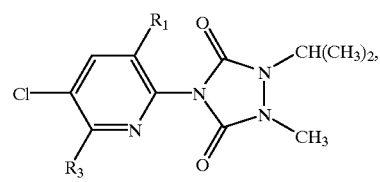 (I₁₄₈)

wherein substituents $R_1$ and $R_3$ are defined in Table A, constituting the disclosure of 448 specific compounds of formula $I_{148}$.

TABLE 149

A further preferred group of compounds of formula I corresponds to the general formula

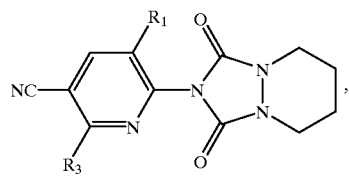 (I₁₄₉)

wherein substituents $R_1$ and $R_3$ are defined in Table A, constituting the disclosure of 448 specific compounds of formula $I_{149}$.

TABLE 150

A further preferred group of compounds of formula I corresponds to the general formula

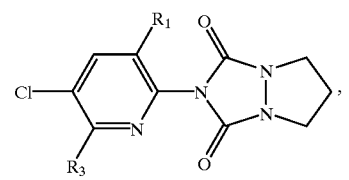 (I₁₅₀)

wherein substituents $R_1$ and $R_3$ are defined in Table A, constituting the disclosure of 448 specific compounds of formula $I_{150}$.

TABLE 151

A further preferred group of compounds of formula I corresponds to the general formula

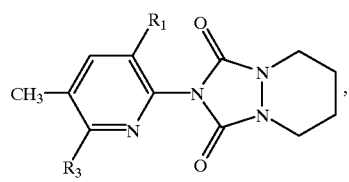 (I₁₅₁)

wherein substituents $R_1$ and $R_3$ are defined in Table A, constituting the disclosure of 448 specific compounds of formula $I_{151}$.

TABLE 152

A further preferred group of compounds of formula I corresponds to the general formula

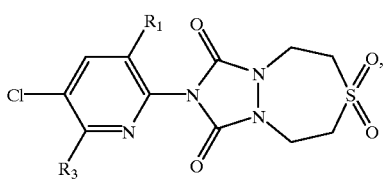 (I₁₅₂)

wherein substituents $R_1I$ and $R_3$ are defined in Table A, constituting the disclosure of 448 specific compounds of formula $I_{152}$.

TABLE 153

A further preferred group of compounds of
formula I corresponds to the general formula

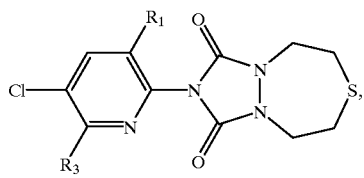
(I$_{153}$)

wherein substituents R$_1$ and R$_3$ are defined in Table A, constituting the disclosure of 448 specific compounds of formula I$_{153}$.

TABLE 154

A further preferred group of compounds of
formula I corresponds to the general formula

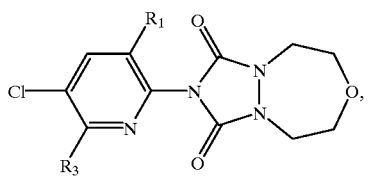
(I$_{154}$)

wherein substituents R$_1$ and R$_3$ are defined in Table A constituting the disclosure of 448 specific compounds of formula I$_{154}$.

TABLE 155

A further preferred group of compounds of
formula I corresponds to the general formula

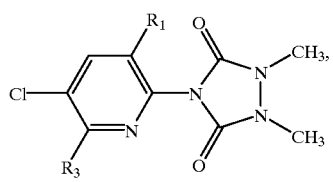
(I$_{155}$)

wherein substituents R$_1$ and R$_3$ are defined in Table A, constituting the disclosure of 448 specific compounds of formula I$_{155}$.

TABLE 156

A further preferred group of compounds of
formula I corresponds to the general formula

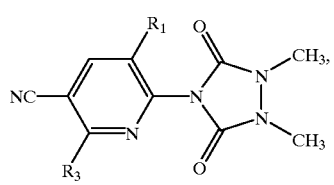
(I$_{156}$)

wherein substituents R$_1$ and R$_3$ are defined in Table A, constituting the disclosure of 448 specific compounds of formula I$_{156}$.

TABLE 157

A further preferred group of compounds of
formula I corresponds to the general formula

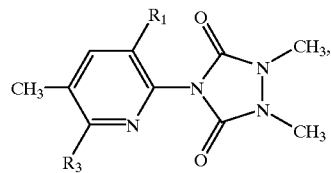
(I$_{157}$)

wherein substituents R$_1$ and R$_3$ are defined in Table A, constituting the disclosure of 448 specific compounds of formula I$_{157}$.

TABLE 158

A further preferred group of compounds of
formula I corresponds to the general formula

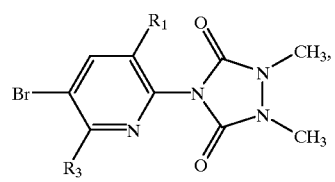
(I$_{158}$)

wherein substituents R$_1$ and R$_3$ are defined in Table A, constituting the disclosure of 448 specific compounds of formula I$_{158}$.

TABLE 159

A further preferred group of compounds of
formula I corresponds to the general formula

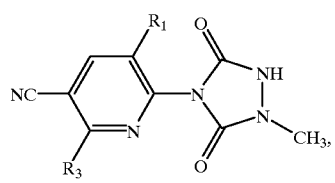
(I$_{159}$)

wherein substituents R$_1$ and R$_3$ are defined in Table A, constituting the disclosure of 448 specific compounds of formula I$_{159}$.

TABLE 160

A further preferred group of compounds of
formula I corresponds to the general formula

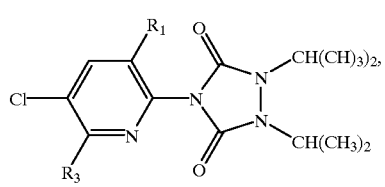
(I$_{160}$)

wherein substituents R$_1$ and R$_3$ are defined in Table A, constituting the disclosure of 448 specific compounds of formula I$_{160}$.

TABLE 161

A further preferred group of compounds of
formula I corresponds to the general formula

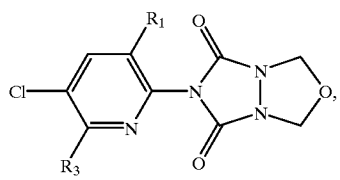

(I$_{161}$)

wherein substituents R$_1$ and R$_3$ are defined in Table A, constituting the disclosure of 448 specific compounds of formula I$_{161}$.

TABLE 162

A further preferred group of compounds of
formula I corresponds to the general formula

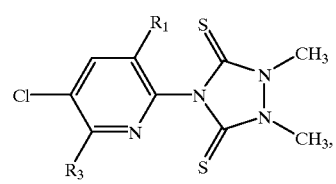

(I$_{162}$)

wherein substituents R$_1$ and R$_3$ are defined in Table A, constituting the disclosure of 448 specific compounds of formula I$_{162}$.

TABLE 163

A further preferred group of compounds of
formula I corresponds to the general formula

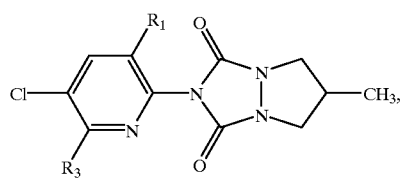

(I$_{163}$)

wherein substituents R$_1$ and R$_3$ are defined in Table A, constituting the disclosure of 448 specific compounds of formula I$_{163}$.

TABLE 164

A further preferred group of compounds of
formula I corresponds to the general formula

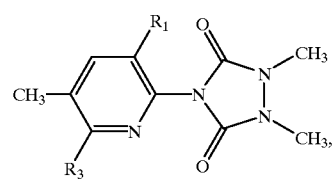

(I$_{164}$)

wherein substituents R$_1$ and R$_3$ are defined in Table A, constituting the disclosure of 448 specific compounds of formula I$_{164}$.

TABLE 165

A further preferred group of compounds of
formula I corresponds to the general formula

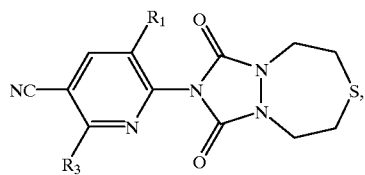

(I$_{165}$)

wherein substituents R$_1$ and R$_3$ are defined in Table A, constituting the disclosure of 448 specific compounds of formula I$_{165}$.

TABLE 166

A further preferred group of compounds of
formula I corresponds to the general formula

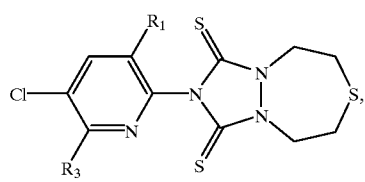

(I$_{166}$)

wherein substituents R$_1$ and R$_3$ are defined in Table A, constituting the disclosure of 448 specific compounds of formula I$_{166}$.

TABLE 167

A further preferred group of compounds of
formula I corresponds to the general formula

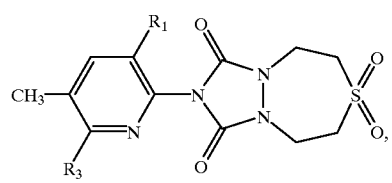

(I$_{167}$)

wherein substituents R$_1$ and R$_3$ are defined in Table A, constituting the disclosure of 448 specific compounds of formula I$_{167}$.

TABLE 168

A further preferred group of compounds of
formula I corresponds to the general formula

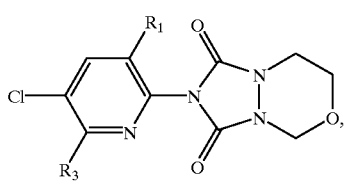

(I$_{168}$)

wherein substituents R$_1$ and R$_3$ are defined in Table A, constituting the disclosure of 448 specific compounds of formula I$_{168}$.

TABLE 169

A further preferred group of compounds of
formula I corresponds to the general formula

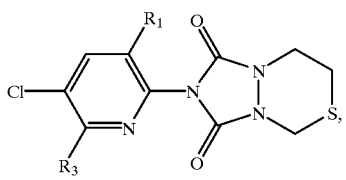
($I_{169}$)

wherein substituents $R_1$ and $R_3$ are defined in Table A, constituting the disclosure of 448 specific compounds of formula $I_{169}$.

TABLE 170

A further preferred group of compounds of
formula I corresponds to the general formula

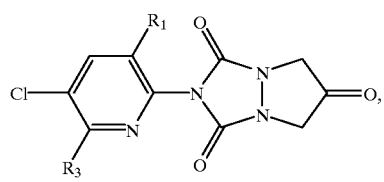
($I_{170}$)

wherein substituents $R_1$ and $R_3$ are defined in Table A, constituting the disclosure of 448 specific compounds of formula $I_{170}$.

TABLE 171

A further preferred group of compounds of
formula I corresponds to the general formula

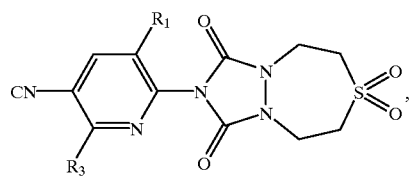
($I_{171}$)

wherein substituents $R_1$ and $R_3$ are defined in Table A, constituting the disclosure of 448 specific compounds of formula $I_{171}$.

TABLE 172

A further preferred group of compounds of
formula I corresponds to the general formula

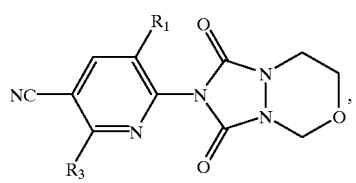
($I_{172}$)

wherein substituents $R_1$ and $R_3$ are defined in Table A, constituting the disclosure of 448 specific compounds of formula $I_{172}$.

TABLE 173

A further preferred group of compounds of
formula I corresponds to the general formula

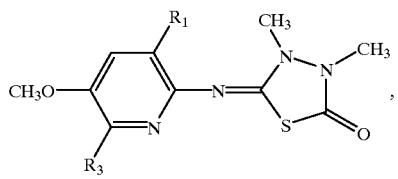
($I_{173}$)

wherein substituents $R_1$ and $R_3$ are defined in Table A, constituting the disclosure of 448 specific compounds of formula $I_{173}$.

TABLE 174

A further preferred group of compounds of
formula I corresponds to the general formula

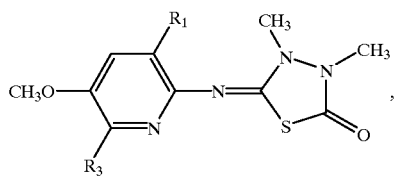
($I_{174}$)

wherein substituents $R_1$ and $R_3$ are defined in Table A, constituting the disclosure of 448 specific compounds of formula $I_{174}$.

TABLE 175

A further preferred group of compounds of
formula I corresponds to the general formula

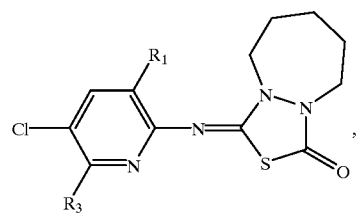
($I_{175}$)

wherein substituents $R_1$ and $R_3$ are defined in Table A, constituting the disclosure of 448 specific compounds of formula $I_{175}$.

TABLE 176

A further preferred group of compounds of
formula I corresponds to the general formula

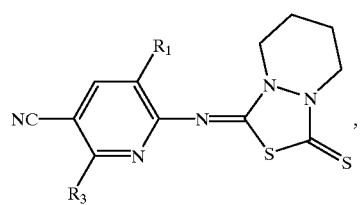
($I_{176}$)

wherein substituents $R_1$ and $R_3$ are defined in Table A, constituting the disclosure of 448 specific compounds of formula 176.

TABLE 177

A further preferred group of compounds of
formula I corresponds to the general formula

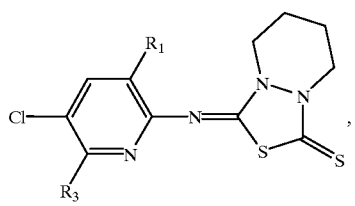
($I_{177}$)

wherein substituents $R_1$ and $R_3$ are defined in Table A, constituting the disclosure of 448 specific compounds of formula $I_{177}$.

TABLE 178

A further preferred group of compounds of
formula I corresponds to the general formula

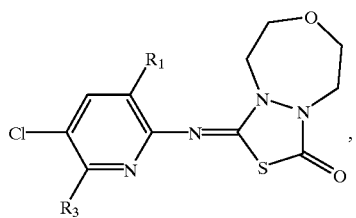
($I_{178}$)

wherein substituents $R_1$ and $R_3$ are defined in Table A, constituting the disclosure of 448 specific compounds of formula $I_{178}$.

TABLE 179

A further preferred group of compounds of
formula I corresponds to the general formula

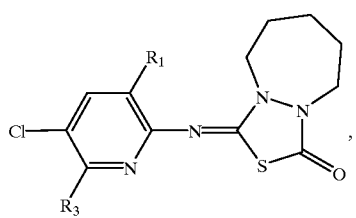
($I_{179}$)

wherein substituents $R_1$ and $R_3$ are defined in Table A, constituting the disclosure of 448 specific compounds of formula $I_{179}$.

TABLE 180

A further preferred group of compounds of
formula I corresponds to the general formula

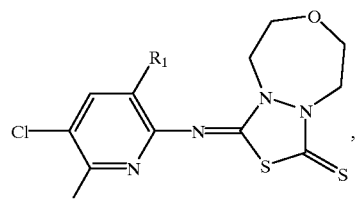
($I_{180}$)

wherein substituents $R_1$ and $R_3$ are defined in Table A, constituting the disclosure of 448 specific compounds of formula $I_{180}$.

TABLE 181

A further preferred group of compounds of
formula I corresponds to the general formula

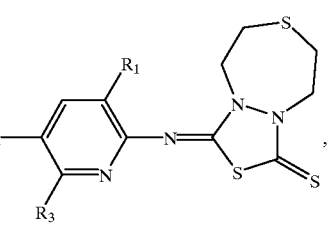
($I_{181}$)

wherein substituents $R_1$ and $R_3$ are defined in Table A, constituting the disclosure of 448 specific compounds of formula $I_{181}$.

TABLE 182

A further preferred group of compounds of
formula I corresponds to the general formula

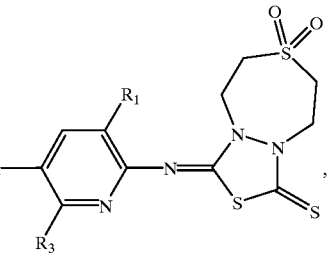
($I_{182}$)

wherein substituents $R_1$ and $R_3$ are defined in Table A, constituting the disclosure of 448 specific compounds of formula $I_{182}$.

TABLE 183

A further preferred group of compounds of formula I corresponds to the general formula

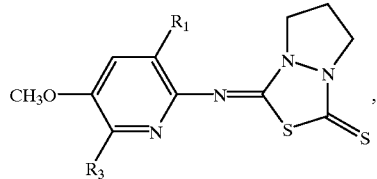

(I$_{183}$)

wherein substituents R$_1$ and R$_3$ are defined in Table A, constituting the disclosure of 448 specific compounds of formula I$_{183}$.

TABLE 184

A further preferred group of compounds of formula I corresponds to the general formula

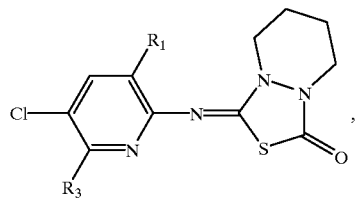

(I$_{184}$)

wherein substituents R$_1$ and R$_3$ are defined in Table A, constituting the disclosure of 448 specific compounds of formula I$_{184}$.

TABLE 185

A further preferred group of compounds of formula I corresponds to the general formula

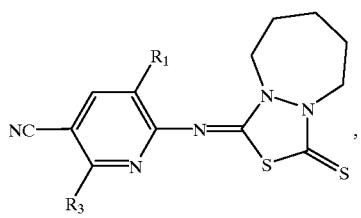

(I$_{185}$)

wherein substituents R$_1$ and R$_3$ are defined in Table A, constituting the disclosure of 448 specific compounds of formula I$_{185}$.

TABLE 186

A further preferred group of compounds of formula I corresponds to the general formula

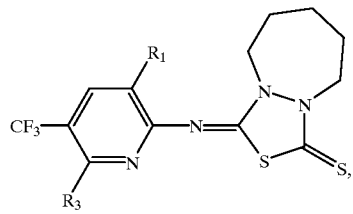

(I$_{186}$)

wherein substituents R$_1$ and R$_3$ are defined in Table A, constituting the disclosure of 448 specific compounds of formula I$_{186}$

TABLE 187

A further preferred group of compounds of formula I corresponds to the general formula

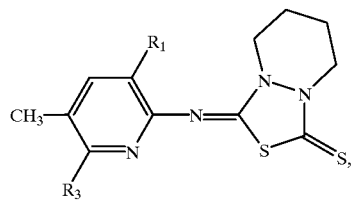

(I$_{187}$)

wherein substituents R$_1$ and R$_3$ are defined in Table A, constituting the disclosure of 448 specific compounds of formula I$_{187}$.

TABLE 188

A further preferred group of compounds of formula I corresponds to the general formula

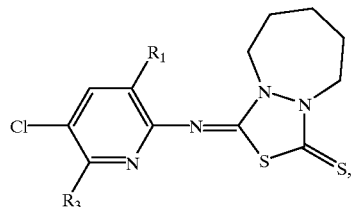

(I$_{188}$)

wherein substituents R$_1$ and R$_3$ are defined in Table A, constituting the disclosure of 448 specific compounds of formula I$_{188}$.

TABLE 189

A further preferred group of compounds of formula I corresponds to the general formula

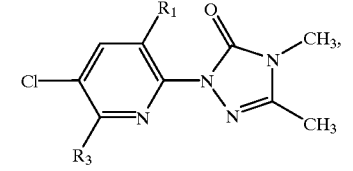

(I$_{189}$)

wherein substituents $R_1$ and $R_3$ are defined in Table A, constituting the disclosure of 448 specific compounds of formula $I_{189}$.

TABLE 190

A further preferred group of compounds of formula I corresponds to the general formula

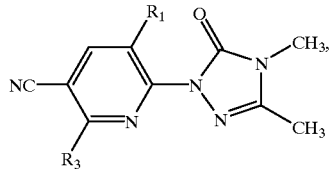
($I_{190}$)

wherein substituents $R_1$ and $R_3$ are defined in Table A, constituting the disclosure of 448 specific compounds of formula $I_{190}$.

TABLE 191

A further preferred group of compounds of formula I corresponds to the general formula

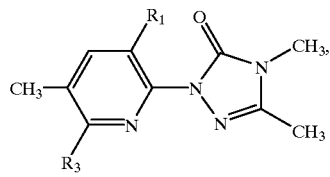
($I_{191}$)

wherein substituents $R_1$ and $R_3$ are defined in Table A, constituting the disclosure of 448 specific compounds of formula $I_{191}$.

TABLE 192

A further preferred group of compounds of formula I corresponds to the general formula

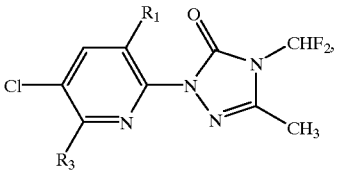
($I_{192}$)

wherein substituents $R_1$ and $R_3$ are defined in Table A, constituting the disclosure of 448 specific compounds of formula $I_{192}$.

TABLE 193

A further preferred group of compounds of formula I corresponds to the general formula

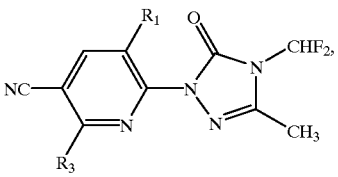
($I_{193}$)

wherein substituents $R_1$ and $R_3$ are defined in Table A, constituting the disclosure of 448 specific compounds of formula $I_{193}$.

TABLE 194

A further preferred group of compounds of formula I corresponds to the general formula

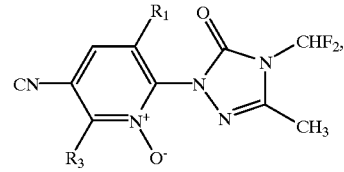
($I_{194}$)

wherein substituents $R_1$ and $R_3$ are defined in Table A, constituting the disclosure of 448 specific compounds of formula $I_{194}$.

TABLE 195

A further preferred group of compounds of formula I corresponds to the general formula

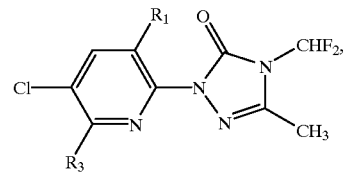
($I_{195}$)

wherein substituents $R_1$ and $R_3$ are defined in Table A, constituting the disclosure of 448 specific compounds of formula $I_{195}$.

TABLE 196

A further preferred group of compounds of formula I corresponds to the general formula

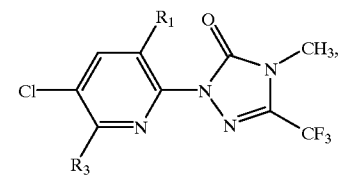
($I_{196}$)

wherein substituents $R_1$ and $R_3$ are defined in Table A, constituting the disclosure of 448 specific compounds of formula $I_{196}$.

TABLE 197

A further preferred group of compounds of formula I corresponds to the general formula

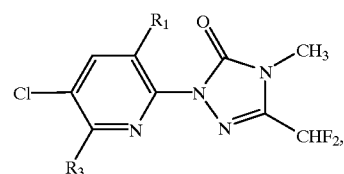
($I_{197}$)

wherein substituents $R_1$ and $R_3$ are defined in Table A, constituting the disclosure of 448 specific compounds of formula $I_{197}$.

TABLE 198

A further preferred group of compounds of
formula I corresponds to the general formula

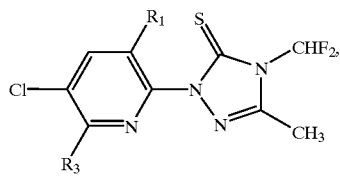
(I$_{198}$)

wherein substituents R$_1$ and R$_3$ are defined in Table A, constituting the disclosure of 448 specific compounds of formula I$_{198}$.

TABLE 199

A further preferred group of compounds of
formula I corresponds to the general formula

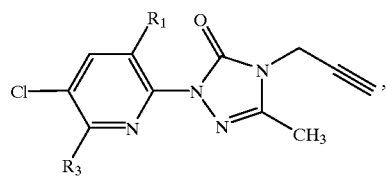
(I$_{199}$)

wherein substituents R$_1$ and R$_3$ are defined in Table A, constituting the disclosure of 448 specific compounds of formula I$_{199}$.

TABLE 200

A further preferred group of compounds of
formula I corresponds to the general formula

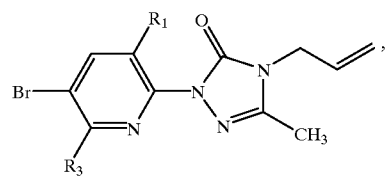
(I$_{200}$)

wherein substituents R$_1$ and R$_3$ are defined in Table A, constituting the disclosure of 448 specific compounds of formula I$_{200}$.

TABLE 201

A further preferred group of compounds of
formula I corresponds to the general formula

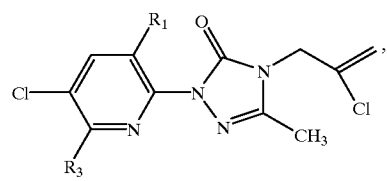
(I$_{201}$)

wherein substituents R$_1$ and R$_3$ are defined in Table A, constituting the disclosure of 448 specific compounds of formula I$_{201}$.

TABLE 202

A further preferred group of compounds of
formula I corresponds to the general formula

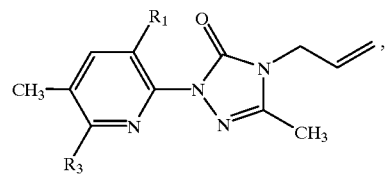
(I$_{202}$)

wherein substituents R$_1$ and R$_3$ are defined in Table A, constituting the disclosure of 448 specific compounds of formula I$_{202}$.

TABLE 203

A further preferred group of compounds of
formula I corresponds to the general formula

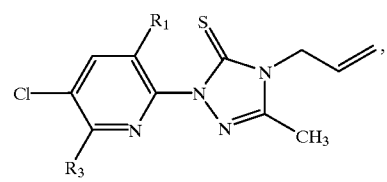
(I$_{203}$)

wherein substituents R$_1$ and R$_3$ are defined in Table A, constituting the disclosure of 448 specific compounds of formula I$_{203}$.

TABLE 204

A further preferred group of compounds of
formula I corresponds to the general formula

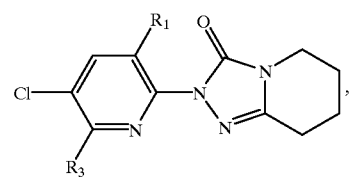
(I$_{204}$)

wherein substituents R$_1$ and R$_3$ are defined in Table A, constituting the disclosure of 448 specific compounds of formula I$_{204}$.

TABLE 205

A further preferred group of compounds of
formula I corresponds to the general formula

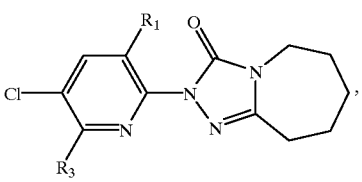
(I$_{205}$)

wherein substituents R$_1$ and R$_3$ are defined in Table A, constituting the disclosure of 448 specific compounds of formula I$_{205}$.

TABLE 206

A further preferred group of compounds of formula I corresponds to the general formula

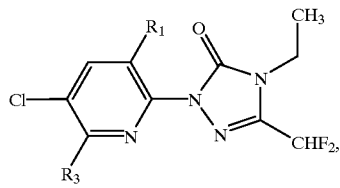
($I_{206}$)

wherein substituents $R_1$ and $R_3$ are defined in Table A, constituting the disclosure of 448 specific compounds of formula $I_{206}$.

TABLE 207

A further preferred group of compounds of formula I corresponds to the general formula ($I_{207}$)

wherein substituents $R_1$ and $R_3$ are defined in Table A, constituting the disclosure of 448 specific compounds of formula $I_{207}$.

TABLE 208

A further preferred group of compounds of formula I corresponds to the general formula ($I_{208}$)

wherein substituents $R_1$ and $R_3$ are defined in Table A, constituting the disclosure of 448 specific compounds of formula $I_{208}$.

TABLE 209

A further preferred group of compounds of formula I corresponds to the general formula ($I_{209}$)

wherein substituents $R_1$ and $R_3$ are defined in Table A, constituting the disclosure of 448 specific compounds of formula $I_{209}$.

TABLE 210

A further preferred group of compounds of formula I corresponds to the general formula

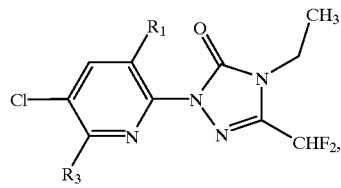
($I_{210}$)

wherein substituents $R_1$ and $R_3$ are defined in Table A, constituting the disclosure of 448 specific compounds of formula $I_{210}$.

TABLE 211

A further preferred group of compounds of formula I corresponds to the general formula ($I_{211}$)

wherein substituents $R_1$ and $R_3$ are defined in Table A, constituting the disclosure of 448 specific compounds of formula $I_{211}$.

TABLE 212

A further preferred group of compounds of formula I corresponds to the general formula ($I_{212}$)

wherein substituents $R_1$ and $R_3$ are defined in Table A, constituting the disclosure of 448 specific compounds of formula $I_{212}$.

TABLE 213

A further preferred group of compounds of formula I corresponds to the general formula ($I_{213}$)

wherein substituents $R_1$ and $R_3$ are defined in Table A, constituting the disclosure of 448 specific compounds of formula $I_{213}$.

TABLE 214

A further preferred group of compounds of formula I corresponds to the general formula

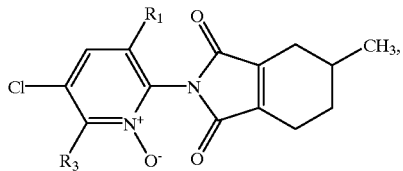
($I_{214}$)

wherein substituents $R_1$ and $R_3$ are defined in Table A, constituting the disclosure of 448 specific compounds of formula $I_{214}$.

TABLE 215

A further preferred group of compounds of formula I corresponds to the general formula

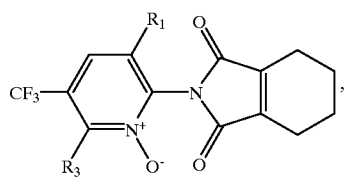
($I_{215}$)

wherein substituents $R_1$ and $R_3$ are defined in Table A, constituting the disclosure of 448 specific compounds of formula $I_{215}$.

TABLE 216

A further preferred group of compounds of formula I corresponds to the general formula

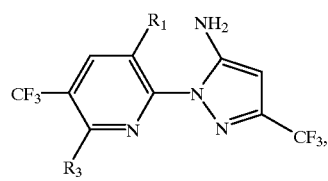
($I_{216}$)

wherein substituents $R_1$ and $R_3$ are defined in Table A, constituting the disclosure of 448 specific compounds of formula $I_{216}$.

TABLE 217

A further preferred group of compounds of formula I corresponds to the general formula

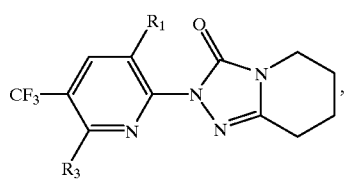
($I_{217}$)

wherein substituents $R_1$ and $R_3$ are defined in Table A, constituting the disclosure of 448 specific compounds of formula $I_{217}$.

TABLE 218

A further preferred group of compounds of formula I corresponds to the general formula

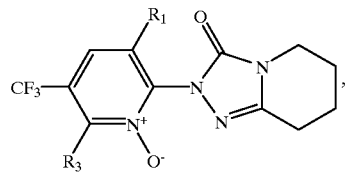
($I_{218}$)

wherein substituents $R_1$ and $R_3$ are defined in Table A, constituting the disclosure of 448 specific compounds of formula $I_{218}$.

TABLE 219

A further preferred group of compounds of formula I corresponds to the general formula

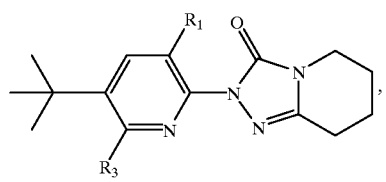
($I_{219}$)

wherein substituents $R_1$ and $R_3$ are defined in Table A, constituting the disclosure of 448 specific compounds of formula $I_{219}$.

TABLE 220

A further preferred group of compounds of formula I corresponds to the general formula

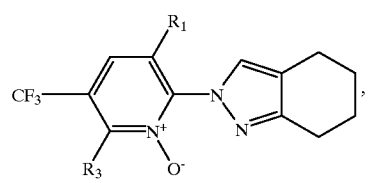
($I_{220}$)

wherein substituents $R_1$ and $R_3$ are defined in Table A, constituting the disclosure of 448 specific compounds of formula $I_{220}$.

TABLE 221

A further preferred group of compounds of formula I corresponds to the general formula

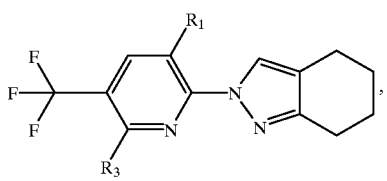
($I_{221}$)

wherein substituents $R_1$ and $R_3$ are defined in Table A, constituting the disclosure of 448 specific compounds of formula $I_{221}$.

TABLE 222

A further preferred group of compounds of formula I corresponds to the general formula

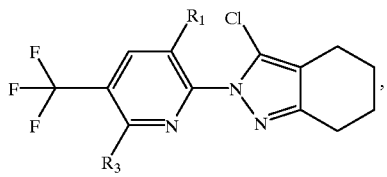

($I_{222}$)

wherein substituents $R_1$ and $R_3$ are defined in Table A, constituting the disclosure of 448 specific compounds of formula $I_{222}$.

TABLE A

| Cmpd no. | $R_1$ | $R_3$ |
|---|---|---|
| .001 | F | CN |
| .002 | F | CHO |
| .003 | F | $COCH_3$ |
| .004 | F | $COOCH_2CH_3$ |
| .005 | F | $COOCH_2C_6H_5$ |
| .006 | F | COCl |
| .007 | F | $COCH_2CH_2Cl$ |
| .008 | F | COOH |
| .009 | F | $COOCH_3$ |
| .010 | F | $COOCH_2CH_3$ |
| .011 | F | $COOCH(CH_3)_2$ |
| .012 | F | $COOCH_2CH=CH_2$ |
| .013 | F | $COO(CH_2)_5CH_3$ |
| .014 | F | $COOCH(CH_3)CH=CH_2$ |
| .015 | F | $COOCH_2(2\text{-}F\text{—}C_6H_5)$ |
| .016 | F | $COOC_6H_5$ |
| .017 | F | $COOCH_2CH_2OCH_3$ |
| .018 | F | $COOCH(CH_3)CH_2SCH_3$ |
| .019 | F | COO(oxetanyl) |
| .020 | F | $COOCH_2$(oxiranyl) |
| .021 | F | COO(cylopentyl) |
| .022 | F | $COSCH_3$ |
| .023 | F | $COSCH(CH_3)_2$ |
| .024 | F | $COSCH_2C_6H_5$ |
| .025 | F | $CONH_2$ |
| .026 | F | $CONH(CH_2CH=CH_2)$ |
| .027 | F | $CONHCH_2C_6H_5$ |
| .028 | F | $CON(CH_2CH=CH_2)_2$ |
| .029 | F | $CON(CH_3)OCH_3$ |
| .030 | F | $COOCH_2CH_2COOH$ |
| .031 | F | $COOCH(CH_3)COOCH_3$ |
| .032 | F | $COOCH(CH_3)COOCH_2C_6H_5$ |
| .033 | F | $COOCH(CH_3)CH_2COOCH_2CH_3$ |
| .034 | F | $(S)\text{-}COOCH(CH_3)CH_2COOCH_2CH=CH_2$ |
| .035 | F | $(R)\text{-}COOCH(CH_3)CH_2COOCH_2CH=CH_2$ |
| .036 | F | $COOCH(CH_3)CH_2CONHCH_2CH_3$ |
| .037 | F | $COOCH(CH_3)CH_2CON(CH_3)_2$ |
| .038 | F | $(R)\text{-}COOCH(CH_3)CH_2COOCH_3$ |
| .039 | F | $COOCH(CH_3)CH_2COOCH_2CH=CH_2$ |
| .040 | F | $COOC(CH_3)_2COCH_3$ |
| .041 | F | $COOC(CH_3)_2COOH$ |
| .042 | F | $COOC(CH_3)_2COOCH_3$ |
| .043 | F | $COOC(CH_3)_2COOCH_2CH_3$ |
| .044 | F | $COOC(CH_3)_2COOCH(CH_3)_2$ |
| .045 | F | $COOC(CH_3)_2COO(CH_2)_4CH_3$ |
| .046 | F | $COOC(CH_3)_2COOCH_2C_6H_5$ |
| .047 | F | $COOC(CH_3)_2COOCH_2(2\text{-}F\text{—}C_6H_5)$ |
| .048 | F | $COOC(CH_3)_2COOCH_2CH=CH_2$ |
| .049 | F | $(R)\text{-}COOCH(CH_3)COOCH_2CH_3$ |
| .050 | F | $COOC(CH_3)_2COOCH_2C\equiv CH$ |
| .051 | F | $COO(CH_3)_2COOCH_2CH_2OCH_2CH_3$ |
| .052 | F | $COOC(CH_3)_2COSCH_3$ |
| .053 | F | $COOC(CH_3)_2COSCH(CH_3)_2$ |
| .054 | F | $COOC(CH_3)_2COSCH_2C_6H_5$ |
| .055 | F | $COOC(CH_3)_2CONH_2$ |
| .056 | F | $COOC(CH_3)_2CONHCH_2CH=CH_2$ |
| .057 | F | $COOC(CH_3)_2CON(CH_2CH_3)_2$ |
| .058 | F | $COOC(CH_3)_2CON(CH_3)CH_2CH_2OCH_3$ |
| .059 | F | $COSCH(CH_3)COOH$ |
| .060 | F | $COSCH(CH_3)COOCH_3$ |
| .061 | F | $COSCH(CH_3)CONHCH_2CH=CH_2$ |
| .062 | F | $CON(CH_3)CH_2COOH$ |
| .063 | F | $CON(CH_3)C(CH_3)_2COOCH_2CH_3$ |
| .064 | F | $CON(CH_3)OCH_2COOCH_3$ |
| .065 | F | $CON(CH_3)OH$ |
| .066 | F | $CH_3$ |
| .067 | F | $CH_2CH_3$ |
| .068 | F | $CH(OH)CH_3$ |
| .069 | F | $CH(OCH_2CH=CH_2)CH_3$ |
| .070 | F | $CH_2Cl$ |
| .071 | F | $CH_2OH$ |
| .072 | F | $CH_2OCOCH_3$ |
| .073 | F | $CHClCH_3$ |
| .074 | F | $CH_2CH_2CF_3$ |
| .075 | F | $CH=CHCF_3$ |
| .076 | F | $CH_2CH=CH_2$ |
| .077 | F | $CH=CHCH_3$ |
| .078 | F | $C\equiv CH$ |
| .079 | F | $CCCH_2OH$ |
| .080 | F | $CH_2CHClCOOH$ |
| .081 | F | $(R)\text{-}CH_2CHClCOOH$ |
| .082 | F | $(S)\text{-}CH_2CHClCOOH$ |
| .083 | F | $CH_2CH(CH_3)COOH$ |
| .084 | F | $CH_2CH(CH_3)COOCH_2CH_3$ |
| .085 | F | $CH(Cl)CH_2COOCH_3$ |
| .086 | F | $CH(Cl)C(Cl)_2COOH$ |
| .087 | F | $CH(Cl)CH(Cl)COOCH_2CH_3$ |
| .088 | F | $CH_2CH(CH_3)COOH$ |
| .089 | F | $CH_2CH(CH_3)COCH_2CH=CH_2$ |
| .090 | F | $CH_2CH(CH_3)CONH(CH_2CH=CH_2)$ |
| .091 | F | $CH_2CH(CH_3)CON(CH_3)_2$ |
| .092 | F | $CH_2CH(CH_3)COSCH(CH_3)_2$ |
| .093 | F | $CH_2CHClCOOC(CH_3)_3$ |
| .094 | F | $CH_2CHClCOOCH_3$ |
| .095 | F | $CH_2CHClCOOCH_2CH_3$ |
| .096 | F | $CH_2CHClCOOCH(CH_3)_2$ |
| .097 | F | $CH_2CHClCOOCH_2CH=CH_2$ |
| .098 | F | $CH_2CHClCOOCH_2C_6H_5$ |
| .099 | F | $CH_2CHClCOSCH_3$ |
| .100 | F | $CH_2CHClCOSCH(CH_3)_2$ |
| .101 | F | $CH_2CHClCOSCH_2C_6H_5$ |
| .102 | F | $CH_2CHClCONH_2$ |
| .103 | F | $CH_2CHClCONH(CH_2CH=CH_2)$ |
| .104 | F | $CH_2CHClCON(CH_3)_2$ |
| .105 | F | $CH_2CHClCONH(CH_2C_6H_5)$ |
| .106 | F | $CH_2CHClCON(CH_3)CH_2C_6H_5$ |
| .107 | F | $CH=CHCOOH$ |
| .108 | F | $(E)\text{-}CH=CHCOOH$ |
| .109 | F | $(Z)\text{-}CH=CHCOOH$ |
| .110 | F | $CH=CHCOOCH_3$ |
| .111 | F | $CH=CHCOOCH_2C_6H_5$ |
| .112 | F | $CH=CHCONH_2$ |
| .113 | F | $CH=CHCONH(CH_2CH=CH_2)$ |
| .114 | F | $CH=C(Cl)COOH$ |
| .115 | F | $CH=C(Cl)CONH_2$ |
| .116 | F | $CH=C(Cl)CONH(CH_2CH_3)$ |
| .117 | F | $CH=C(Cl)CON(CH_2CH_3)_2$ |
| .118 | F | $CH=C(Cl)CONH(CH_2C_6H_5)$ |
| .119 | F | $CH=C(Cl)COSCH_3$ |
| .120 | F | $CH=C(Cl)COSCH(CH_3)_2$ |
| .121 | F | $CH=C(CH_3)COOH$ |
| .122 | F | $CH=C(CH_3)CONH(CH_2CH=CH_2)$ |
| .123 | F | $CH=C(CH_3)CON(CH_3)_2$ |
| .124 | F | $CH=C(CH_3)COSCH_2CH_3$ |
| .125 | F | $CH=C(CN)COOH$ |
| .126 | F | $CH=C(CN)COOC(CH_3)_3$ |
| .127 | F | $CH=C(CN)CON(CH_2CH=CH_2)_2$ |
| .128 | F | $CH=C(COOH)_2$ |
| .129 | F | $CH=C(C_6H_5)COOH$ |
| .130 | F | $CH=CHCH_2OH$ |
| .131 | Cl | CN |
| .132 | Cl | CHO |
| .133 | Cl | $COCH_3$ |

TABLE A-continued

| Cmpd no. | $R_1$ | $R_3$ |
|---|---|---|
| .134 | Cl | COOCH$_2$CH$_3$ |
| .135 | Cl | COOCH$_2$C$_6$H$_5$ |
| .136 | Cl | COCl |
| .137 | Cl | COCH$_2$CH$_2$Cl |
| .138 | Cl | COOH |
| .139 | Cl | COOCH$_3$ |
| .140 | Cl | COOCH$_2$CH$_3$ |
| .141 | Cl | COOCH(CH$_3$)$_2$ |
| .142 | Cl | COOCH$_2$CH=CH$_2$ |
| .143 | Cl | COO(CH$_2$)$_5$CH$_3$ |
| .144 | Cl | COOCH(CH$_3$)CH=CH$_2$ |
| .145 | Cl | COOCH$_2$(2-F—C$_6$H$_5$) |
| .146 | Cl | COOC$_6$H$_5$ |
| .147 | Cl | COOCH$_2$CH$_2$OCH$_2$CH$_3$ |
| .148 | Cl | COOCH(CH$_3$)CH$_2$SCH$_3$ |
| .149 | Cl | COO(oxetanyl) |
| .150 | Cl | COOCH$_2$(oxiranyl) |
| .151 | Cl | COO(cylopentyl) |
| .152 | Cl | COSCH$_3$ |
| .153 | Cl | COSCH(CH$_3$)$_2$ |
| .154 | Cl | COSCH$_2$C$_6$H$_5$ |
| .155 | Cl | CONH$_2$ |
| .156 | Cl | CONH(CH$_2$CH=CH$_2$) |
| .157 | Cl | CONHCH$_2$C$_6$H$_5$ |
| .158 | Cl | CON(CH$_2$CH=CH$_2$)$_2$ |
| .159 | Cl | CON(CH$_3$)OCH$_3$ |
| .160 | Cl | COOCH$_2$CH$_2$COOH |
| .161 | Cl | COOCH(CH$_3$)COOCH$_3$ |
| .162 | Cl | COOCH(CH$_3$)COOCH$_2$C$_6$H$_5$ |
| .163 | Cl | COOCH(CH$_3$)CH$_2$COOCH$_2$CH$_3$ |
| .164 | Cl | (S)-COOCH(CH$_3$)CH$_2$COOCH$_2$CH=CH$_2$ |
| .165 | Cl | (R)-COOCH(CH$_3$)CH$_2$COOCH$_2$CH=CH$_2$ |
| .166 | Cl | COOCH(CH$_3$)CH$_2$CONHCH$_2$CH$_3$ |
| .167 | Cl | COOCH(CH$_3$)CH$_2$CON(CH$_3$)$_2$ |
| .168 | Cl | COOCH(CH$_3$)CH$_2$COSCH$_2$CH$_3$ |
| .169 | Cl | COOCH(CH$_3$)CH$_2$COOCH$_2$CH=CH$_2$ |
| .170 | Cl | COOC(CH$_3$)$_2$COCH$_3$ |
| .171 | Cl | COOC(CH$_3$)$_2$COOH |
| .172 | Cl | COOC(CH$_3$)$_2$COOCH$_3$ |
| .173 | Cl | COOC(CH$_3$)$_2$COOCH$_2$CH$_3$ |
| .174 | Cl | COOC(CH$_3$)$_2$COOCH(CH$_3$)$_2$ |
| .175 | Cl | COOC(CH$_3$)$_2$COO(CH$_2$)$_4$CH$_3$ |
| .176 | Cl | COOC(CH$_3$)$_2$COOCH$_2$C$_6$H$_5$ |
| .177 | Cl | COOC(CH$_3$)$_2$COOCH$_2$(2-F—C$_6$H$_5$) |
| .178 | Cl | COOC(CH$_3$)$_2$COOCH$_2$CH=CH$_2$ |
| .179 | Cl | COOC(CH$_3$)$_2$COOCH(CH$_3$)CH=CH$_2$ |
| .180 | Cl | COOC(CH$_3$)$_2$COOCH$_2$C≡CH |
| .181 | Cl | COO(CH$_3$)$_2$COOCH$_2$CH$_2$OCH$_2$CH$_3$ |
| .182 | Cl | COOC(CH$_3$)$_2$COSCH$_3$ |
| .183 | Cl | COOC(CH$_3$)$_2$COSCH(CH$_3$)$_2$ |
| .184 | Cl | COOC(CH$_3$)$_2$COSCH$_2$C$_6$H$_5$ |
| .185 | Cl | COOC(CH$_3$)$_2$CONH$_2$ |
| .186 | Cl | COOC(CH$_3$)$_2$CONHCH$_2$CH=CH$_2$ |
| .187 | Cl | COOC(CH$_3$)$_2$CON(CH$_2$CH$_3$)$_2$ |
| .188 | Cl | COOC(CH$_3$)$_2$CON(CH$_3$)CH$_2$CH$_2$OCH$_3$ |
| .189 | Cl | COSCH(CH$_3$)COOH |
| .190 | Cl | COSCH(CH$_3$)COOCH$_3$ |
| .191 | Cl | COSCH(CH$_3$)CONHCH$_2$CH=CH$_2$ |
| .192 | Cl | CON(CH$_3$)CH$_2$COOH |
| .193 | Cl | CON(CH$_3$)C(CH$_3$)$_2$COOCH$_2$CH$_3$ |
| .194 | Cl | CON(CH$_3$)OCH$_2$COOCH$_3$ |
| .195 | Cl | CON(CH$_3$)OH |
| .196 | Cl | CH$_3$ |
| .197 | Cl | CH$_2$CH$_3$ |
| .198 | Cl | CH(OH)CH$_3$ |
| .199 | Cl | CH(OCH$_2$CH=CH$_2$)CH$_3$ |
| .200 | Cl | CH$_2$Cl |
| .201 | Cl | CH$_2$OH |
| .202 | Cl | CH$_2$OCOCH$_3$ |
| .203 | Cl | CHClCH$_3$ |
| .204 | Cl | CH$_2$CH$_2$CF$_3$ |
| .205 | Cl | CH=CHCF$_3$ |
| .206 | Cl | CH$_2$CH=CH$_2$ |
| .207 | Cl | CH=CH(CH$_3$) |
| .208 | Cl | C≡CH |
| .209 | Cl | C≡CCH$_2$OH |
| .210 | Cl | CH$_2$CHClCOOH |
| .211 | Cl | (R)-CH$_2$CHClCOOH |
| .212 | Cl | (S)-CH$_2$CHClCOOH |
| .213 | Cl | CH$_2$CH(CH$_3$)COOH |
| .214 | Cl | CH$_2$CH(CH$_3$)COOCH$_2$CH$_3$ |
| .215 | Cl | CH(Cl)CH$_2$COOCH$_3$ |
| .216 | Cl | CH(Cl)C(Cl)$_2$COOH |
| .217 | Cl | CH(Cl)CH(Cl)COOCH$_2$CH$_3$ |
| .218 | Cl | CH$_2$CH(CH$_3$)COOH |
| .219 | Cl | CH$_2$CH(CH$_3$)COCH$_2$CH=CH$_2$ |
| .220 | Cl | CH$_2$CH(CH$_3$)CONH(CH$_2$CH=CH$_2$) |
| .221 | Cl | CH$_2$CH(CH$_3$)CON(CH$_3$)$_2$ |
| .222 | Cl | CH$_2$CH(CH$_3$)COSCH(CH$_3$)$_2$ |
| .223 | Cl | CH$_2$CHClCOOC(CH$_3$)$_3$ |
| .224 | Cl | CH$_2$CHClCOOCH$_3$ |
| .225 | Cl | CH$_2$CHClCOOCH$_2$CH$_3$ |
| .226 | Cl | CH$_2$CHClCOOCH(CH$_3$)$_2$ |
| .227 | Cl | CH$_2$CHClCOOCH$_2$CH=CH$_2$ |
| .228 | Cl | CH$_2$CHClCOOCH$_2$C$_6$H$_5$ |
| .229 | Cl | CH$_2$CHClCOSCH$_3$ |
| .230 | Cl | CH$_2$CHClCOSCH(CH$_3$)$_2$ |
| .231 | Cl | CH$_2$CHClCOSCH$_2$C$_6$H$_5$ |
| .232 | Cl | CH$_2$CHClCONH$_2$ |
| .233 | Cl | CH$_2$CHClCONH(CH$_2$CH=CH$_2$) |
| .234 | Cl | CH$_2$CHClCON(CH$_2$CH$_3$)$_2$ |
| .235 | Cl | CH$_2$CHClCONH(CH$_2$C$_6$H$_5$) |
| .236 | Cl | CH$_2$CHClCON(CH$_3$)CH$_2$C$_6$H$_5$ |
| .237 | Cl | CH=CHCOOH |
| .238 | Cl | (E)-CH=CHCOOH |
| .239 | Cl | (Z)-CH=CHCOOH |
| .240 | Cl | CH=CHCOOCH$_3$ |
| .241 | Cl | CH=CHCOOCH$_2$C$_6$H$_5$ |
| .242 | Cl | CH=CHCOONH$_2$ |
| .243 | Cl | CH=CHCONH(CH$_2$CH=CH$_2$) |
| .244 | Cl | CH=C(Cl)COOH |
| .245 | Cl | CH=C(Cl)CONH$_2$ |
| .246 | Cl | CH=C(Cl)CONH(CH$_2$CH$_3$) |
| .247 | Cl | CH=C(Cl)CON(CH$_2$CH$_3$)$_2$ |
| .248 | Cl | CH=C(Cl)CONH(CH$_2$C$_6$H$_5$) |
| .249 | Cl | CH=C(Cl)COSCH$_3$ |
| .250 | Cl | CH=C(Cl)COSCH(CH$_3$)$_2$ |
| .251 | Cl | CH=C(CH$_3$)COOH |
| .252 | Cl | CH=C(CH$_3$)CONH(CH$_2$CH=CH$_2$) |
| .253 | Cl | CH=C(CH$_3$)CON(CH$_3$)$_2$ |
| .254 | Cl | CH=C(CH$_3$)COSCH$_2$CH$_3$ |
| .255 | Cl | CH=C(CN)COOH |
| .256 | Cl | CH=C(CN)COOC(CH$_3$)$_3$ |
| .257 | Cl | CH=C(CN)CON(CH$_2$CH=CH$_2$)$_2$ |
| .258 | Cl | CH=C(COOH)$_2$ |
| .259 | Cl | CH=C(C$_6$H$_5$)COOH |
| .260 | Cl | CH=CHCH$_2$OH |
| .261 | H | CH$_2$OCOCH$_3$ |
| .262 | H | COOH |
| .263 | H | COCl |
| .264 | H | COOCH$_3$ |
| .265 | H | COOCH(CH$_3$)$_2$ |
| .266 | H | COOCH$_2$C$_6$H$_5$ |
| .267 | H | COSCH(CH$_3$)$_2$ |
| .268 | H | CONH$_2$ |
| .269 | H | CONHCH$_2$C$_6$H$_5$ |
| .270 | H | CON(CH$_2$CH=CH$_2$)$_2$ |
| .271 | H | CON(CH$_3$)OCH$_3$ |
| .272 | H | COOCH(CH$_3$)CH$_2$COOH |
| .273 | H | COOCH(CH$_3$)COOCH$_2$CH$_3$ |
| .274 | H | COOCH(CH$_3$)CH$_2$COOCH$_2$CH=CH$_2$ |
| .275 | H | COOCH(CH$_3$)CH$_2$COSCH$_2$CH$_3$ |
| .276 | H | COOCH(CH$_3$)CH$_2$CONH$_2$ |
| .277 | H | COOCH(CH$_3$)CH$_2$CONH(CH$_2$CH=CH$_2$) |
| .278 | H | COOCH(CH$_3$)COOH |
| .279 | H | COOC(CH$_3$)$_2$COOH |
| .280 | H | COOC(CH$_3$)$_2$COOCH$_3$ |
| .281 | H | COOC(CH$_3$)$_2$COOCH(CH$_3$)$_2$ |
| .282 | H | COOC(CH$_3$)$_2$COOCH$_2$C$_6$H$_5$ |
| .283 | H | COOC(CH$_3$)$_2$COOCH$_2$CH=CH$_2$ |
| .284 | H | COOC(CH$_3$)$_2$COOCH$_2$CH$_2$OCH$_2$CH$_3$ |
| .285 | H | Cyclopropyl |
| .286 | H | COOC(CH$_3$)$_2$CON(CH$_3$)$_2$ |
| .287 | H | COOC(CH$_3$)$_2$CONH(CH$_2$CH=CH$_2$) |

TABLE A-continued

| Cmpd no. | $R_1$ | $R_3$ |
|---|---|---|
| 288 | H | COSCH(CH$_3$)COOH |
| 289 | H | CON(CH$_3$)C(CH$_3$)$_2$COOH |
| 290 | H | CH$_3$ |
| 291 | H | CH$_2$CH$_3$ |
| 292 | H | CH(OH)CH$_3$ |
| 293 | H | CH$_2$Cl |
| 294 | H | CH$_2$OH |
| 295 | H | CH$_2$OCOCH$_3$ |
| 296 | H | CH=CHCF$_3$ |
| 297 | H | CH$_2$CH$_2$CF$_3$ |
| 298 | H | CH$_2$CH=CH$_2$ |
| 299 | H | CH$_2$CHClCOOH |
| 300 | H | CH$_2$CHClCOOCH$_2$CH$_3$ |
| 301 | H | CH$_2$CHClCOOCH$_2$C$_6$H$_5$ |
| 302 | H | CH$_2$CHClCOOCH$_2$CH=CH$_2$ |
| 303 | H | CH$_2$CHClCOOC(CH$_3$)$_3$ |
| 304 | H | CH$_2$CHClCOSCH(CH$_3$)$_2$ |
| 305 | H | CH$_2$CHClCONH$_2$ |
| 306 | H | CH$_2$CHClCONH(CH$_2$CH$_3$) |
| 307 | H | CH$_2$CHClCON(CH$_3$)$_2$ |
| 308 | H | CH(Cl)CH(Cl)COOH |
| 309 | H | CH$_2$C(CH$_3$)ClCOOH |
| 310 | H | CH$_2$C(CH$_3$)ClCOOCH$_2$CH$_3$ |
| 311 | H | CH$_2$C(CH$_3$)ClCOSCH$_3$ |
| 312 | H | CH$_2$C(CH$_3$)ClCONH(CH$_2$CH=CH$_2$) |
| 313 | H | Cyclopropyl |
| 314 | H | CH=CHCOOH |
| 315 | H | CH=C(CH$_3$)COOH |
| 316 | H | CH=C(Cl)COOH |
| 317 | H | CH=C(CN)COOH |
| 318 | H | CH=C(CN)COOCH$_2$CH=CH$_2$ |
| 319 | H | CH=C(Cl)COOCH$_2$CH$_3$ |
| 320 | H | CCCH$_3$ |
| 321 | H | CH=C(Cl)COSCH$_2$CH$_3$ |
| 322 | H | CH=C(Cl)CON(CH$_3$)$_2$ |
| 323 | CH$_3$ | CH$_2$OCOCH$_3$ |
| 324 | CH$_3$ | COOH |
| 325 | CH$_3$ | COCl |
| 326 | CH$_3$ | COOCH$_3$ |
| 327 | CH$_3$ | COOCH(CH$_3$)$_2$ |
| 328 | CH$_3$ | COOCH$_2$C$_6$H$_5$ |
| 329 | CH$_3$ | COSCH(CH$_3$)$_2$ |
| 330 | CH$_3$ | CONH$_2$ |
| 331 | CH$_3$ | CONHCH$_2$C$_6$H$_5$ |
| 332 | CH$_3$ | CON(CH$_2$CH=CH$_2$)$_2$ |
| 333 | CH$_3$ | CON(CH$_3$)OCH$_3$ |
| 334 | CH$_3$ | COOCH(CH$_3$)CH$_2$COOH |
| 335 | F | CCH |
| 336 | CH$_3$ | COOCH(CH$_3$)CH$_2$COOCH$_2$CH=CH$_2$ |
| 337 | CH$_3$ | COOCH(CH$_3$)CH$_2$COSCH$_2$CH$_3$ |
| 338 | CH$_3$ | COOCH(CH$_3$)CH$_2$CONH$_2$ |
| 339 | CH$_3$ | COOCH(CH$_3$)CH$_2$CONH(CH$_2$CH=CH$_2$) |
| 340 | CH$_3$ | COOCH(CH$_3$)COOH |
| 341 | CH$_3$ | COOC(CH$_3$)$_2$COOH |
| 342 | CH$_3$ | COOC(CH$_3$)$_2$COOCH$_3$ |
| 343 | CH$_3$ | COOC(CH$_3$)$_2$COOCH(CH$_3$)$_2$ |
| 344 | CH$_3$ | COOC(CH$_3$)$_2$COOCH$_2$CH$_3$ |
| 345 | CH$_3$ | COOC(CH$_3$)$_2$COOCH$_2$CH=CH$_2$ |
| 346 | CH$_3$ | COOC(CH$_3$)$_2$COOCH$_2$CH$_2$OCH$_2$CH$_3$ |
| 347 | CH$_3$ | COOC(CH$_3$)$_2$CONH$_2$ |
| 348 | CH$_3$ | COOC(CH$_3$)$_2$CON(CH$_3$)$_2$ |
| 349 | CH$_3$ | COOC(CH$_3$)$_2$CONH(CH$_2$CH=CH$_2$) |
| 350 | CH$_3$ | COSCH(CH$_3$)COOH |
| 351 | F | CCC(CH$_3$)$_2$OH |
| 352 | F | CF$_3$ |
| 353 | CH$_3$ | CH$_2$CH$_3$ |
| 354 | CH$_3$ | CH(OH)CH$_3$ |
| 355 | CH$_3$ | CH$_2$Cl |
| 356 | CH$_3$ | CH$_2$OH |
| 357 | CH$_3$ | CH$_2$OCOCH$_3$ |
| 358 | CH$_3$ | CH=CHCF$_3$ |
| 359 | CH$_3$ | CH$_2$CH$_2$CF$_3$ |
| 360 | CH$_3$ | CH$_2$CH=CH$_2$ |
| 361 | CH$_3$ | CH$_2$CHClCOOH |
| 362 | CH$_3$ | CH$_2$CHClCOOCH$_2$CH$_3$ |
| 363 | CH$_3$ | CH$_2$CHClCOOCH$_2$C$_6$H$_5$ |
| 364 | CH$_3$ | CH$_2$CHClCOOCH$_2$CH=CH$_2$ |
| 365 | CH$_3$ | CH$_2$CHClCOOC(CH$_3$)$_3$ |
| 366 | CH$_3$ | CH$_2$CHClCOSCH(CH$_3$)$_2$ |
| 367 | CH$_3$ | CH$_2$CHClCONH$_2$ |
| 368 | Cl | CCC(CH$_3$)$_2$OCH$_3$ |
| 369 | F | CCC(CH$_3$)$_2$OCH$_3$ |
| 370 | CH$_3$ | CH(Cl)CH(Cl)COOH |
| 371 | CH$_3$ | CH$_2$C(CH$_3$)ClCOOH |
| 372 | CH$_3$ | CH$_2$C(CH$_3$)ClCOOCH$_2$CH$_3$ |
| 373 | CH$_3$ | CH$_2$C(CH$_3$)ClCOSCH$_3$ |
| 374 | CH$_3$ | CH$_2$C(CH$_3$)ClCONH(CH$_2$CH=CH$_2$) |
| 375 | CH$_3$ | CH$_2$C(CH$_3$)ClCON(CH$_3$)(CH$_2$CH=CH$_2$) |
| 376 | CH$_3$ | CH=CHCOOH |
| 377 | CH$_3$ | CH=C(CH$_3$)COOH |
| 378 | CH$_3$ | CH=C(Cl)COOH |
| 379 | CH$_3$ | CH=C(CN)COOCH$_2$CH=CH$_2$ |
| 380 | CH$_3$ | CH=C(CN)COOH |
| 381 | CH$_3$ | CH=C(Cl)COOCH$_2$CH$_3$ |
| 382 | CH$_3$ | CH=C(CH$_3$)CONH(CH$_2$CH=CH$_2$) |
| 383 | CH$_3$ | CH=C(Cl)COSCH$_2$CH$_3$ |
| 384 | CH$_3$ | CH=C(Cl)CON(CH$_3$)$_2$ |
| 385 | H | COOCH$_2$CH$_3$ |
| 386 | CH$_3$ | COOCH$_2$CH$_3$ |
| 387 | F | CH=CH$_2$ |
| 388 | F | COSCH$_2$CH$_3$ |
| 389 | F | COO$^-$$^+$NH$_2$(CH(CH$_3$)$_2$)$_2$ |
| 390 | F | COO$^-$$^+$NH(CH$_2$CH$_2$OH)$_3$ |
| 391 | F | COO$^-$$^+$K |
| 392 | F | COOCH$_2$CH(CH$_3$)CF$_3$ |
| 393 | F | COOCH(CH$_3$)COOCH$_2$CH$_3$ |
| 394 | F | CON(CH$_2$CH$_2$CH$_3$)$_2$ |
| 395 | F | COOCH$_2$CH$_2$CH$_2$CH$_3$ |
| 396 | F | COOCH$_2$CH$_2$SCH$_2$CH$_2$CH$_3$ |
| 397 | F | COOCH$_2$CH$_2$CN |
| 398 | F | COOCH$_2$CH$_2$SCH(CH$_3$)$_2$ |
| 399 | F | COOCH$_2$CH$_2$CH$_2$C$_6$H$_5$ |
| 400 | F | COOCH(CH$_3$)CH$_2$CH$_3$ |
| 401 | F | COO(CH$_2$)$_5$COOCH$_2$CH$_3$ |
| 402 | F | COOC(CH$_3$)$_3$ |
| 403 | F | CH=C(CH$_3$)COOCH$_2$CH$_3$ |
| 404 | F | COO-cyclopropyl |
| 405 | F | COO-cyclohexyl |
| 406 | F | COOCH$_2$-cyclopropyl |
| 407 | F | COOCH$_2$C$_6$H$_5$ |
| 408 | F | COOCH$_2$CH$_2$OCH$_3$ |
| 409 | F | COOCH$_2$CH$_2$CH$_3$ |
| 410 | F | COOCH(CH$_3$)$_2$ |
| 411 | F | COOCH$_2$CH$_2$CH$_3$ |
| 412 | F | COOCH$_2$CH(CH$_3$)CH$_2$CH$_3$ |
| 413 | F | COOCH$_2$(p-Cl—C$_6$H$_4$) |
| 414 | F | COOCH(CH$_3$)C$_6$H$_5$ |
| 415 | F | COSCH$_2$(o-F—C$_6$H$_4$) |
| 416 | F | COSCH(CH$_3$)CH$_2$CH$_3$ |
| 417 | F | COSCH(CH$_3$)C$_6$H$_5$ |
| 418 | F | COSCH$_2$CH$_2$CH$_3$ |
| 419 | F | COSCH$_2$CH=CH$_2$ |
| 420 | F | CON(CH$_2$CH=CH$_2$)CH$_2$CH$_3$ |
| 421 | F | CON(SO$_2$CH$_3$)CH$_3$ |
| 422 | F | CON(SO$_2$CH$_3$)CH$_2$CH=CH$_2$ |
| 423 | Cl | COO-cyclopropyl |
| 424 | Cl | COO-cyclohexyl |
| 425 | Cl | COOCH$_2$-cyclopropyl |
| 426 | Cl | COOCH$_2$C$_6$H$_5$ |
| 427 | Cl | COOCH$_2$CH$_2$OCH$_3$ |
| 428 | Cl | COOCH$_2$CH$_2$CH$_3$ |
| 429 | Cl | COOCH$_2$CH(CH$_3$)$_2$ |
| 430 | Cl | COOCH$_2$CH$_2$CH$_2$CH$_3$ |
| 431 | Cl | COOCH$_2$CH(CH$_3$)CH$_2$CH$_3$ |
| 432 | Cl | COOCH$_2$(p-Cl—C$_6$H$_4$) |
| 433 | Cl | COOCH(CH$_3$)C$_6$H$_5$ |
| 434 | Cl | COOCH(CH$_3$)C$_6$H$_5$ |
| 435 | Cl | COSCH$_2$(o-F—C$_6$H$_4$) |
| 436 | Cl | COSCH(CH$_3$)CH$_2$CH$_3$ |
| 437 | Cl | COSCH(CH$_3$)C$_6$H$_5$ |
| 438 | Cl | COSCH$_2$CH$_2$CH$_3$ |
| 439 | Cl | COSCH$_2$CH=CH$_2$ |
| 440 | Cl | CON(CH$_2$CH=CH$_2$)CH$_2$CH$_3$ |
| 441 | Cl | CON(SO$_2$CH$_3$)CH$_3$ |

TABLE A-continued

| Cmpd no. | $R_1$ | $R_3$ |
|---|---|---|
| .442 | Cl | $CON(SO_2CH_3)CH_2CH=CH_2$ |
| .443 | H | $COOC(CH_3)_2COCl$ |
| .444 | F | $CH=C(F)COOCH_2CH_3(E/Z)$ |
| .445 | F | $CH=C(Cl)COOCH_2CH_3(E/Z)$ |
| .446 | F | Cl |
| .447 | F | Br |
| .448 | F | I |

The intermediate products of formulae XXXIX and XXXX (e.g. in reaction scheme 12) are new and likewise comprise part of the invention. The following tables 600 to 647 exemplify preferred compounds of formulae XXXIX and XXXX.

TABLE 600

A preferred group of compounds of formula XXXIX corresponds to the general formula

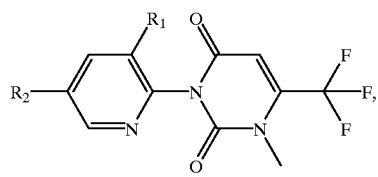
($I_{600}$)

wherein substituents $R_1$ and $R_2$ are defined in Table B, constituting the disclosure of 34 specific compounds of formula $XXXIX_{600}$.

TABLE 601

A further preferred group of compounds of formula XXXIX corresponds to the general formula

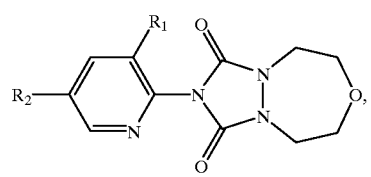
($I_{601}$)

wherein substituents $R_1$ and $R_2$ are defined in Table B, constituting the disclosure of 34 specific compounds of formula $XXXIX_{601}$.

TABLE 602

A further preferred group of compounds of formula XXXIX corresponds to the general formula

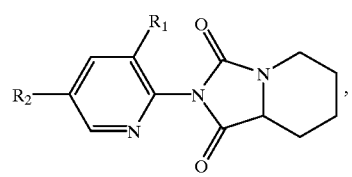
($I_{602}$)

wherein substituents $R_1$ and $R_2$ are defined in Table B, constituting the disclosure of 34 specific compounds of formula $XXXIX_{602}$.

TABLE 603

A further preferred group of compounds of formula XXXIX corresponds to the general formula

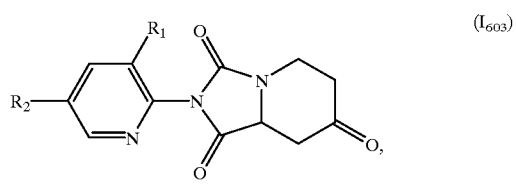
($I_{603}$)

wherein substituents $R_1$ and $R_2$ are defined in Table B, constituting the disclosure of 34 specific compounds of formula $XXXIX_{603}$.

TABLE 604

A further preferred group of compounds of formula XXXIX corresponds to the general formula

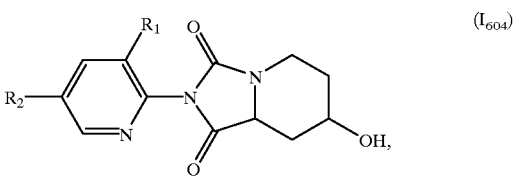
($I_{604}$)

wherein substituents $R_1$ and $R_2$ are defined in Table B, constituting the disclosure of 34 specific compounds of formula $XXXIX_{604}$.

TABLE 605

A further preferred group of compounds of formula XXXIX corresponds to the general formula

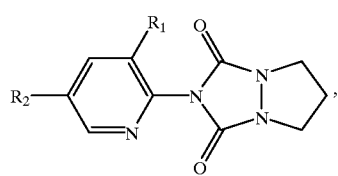
($I_{605}$)

wherein substituents $R_1$ and $R_2$ are defined in Table B, constituting the disclosure of 34 specific compounds of formula $XXXIX_{605}$.

TABLE 606

A further preferred group of compounds of formula XXXIX corresponds to the general formula

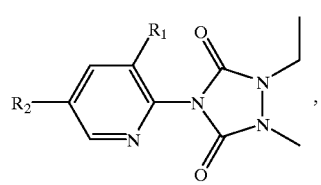
($I_{606}$)

wherein substituents $R_1$ and $R_2$ are defined in Table B, constituting the disclosure of 34 specific compounds of formula $XXXIX_{606}$.

TABLE 607

A further preferred group of compounds of
formula XXXIX corresponds to the general formula

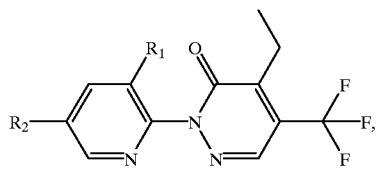
($I_{607}$)

wherein substituents $R_1$ and $R_2$ are defined in Table B, constituting the disclosure of 34 specific compounds of formula $XXXIX_{607}$.

TABLE 608

A further preferred group of compounds of
formula XXXIX corresponds to the general formula

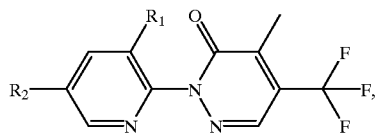
($I_{608}$)

wherein substituents $R_1$ and $R_2$ are defined in Table B, constituting the disclosure of 34 specific compounds of formula $XXXIX_{608}$.

TABLE 609

A further preferred group of compounds of
formula XXXIX corresponds to the general formula

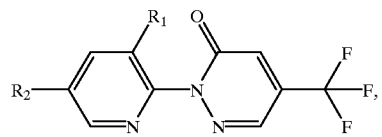
($I_{609}$)

wherein substituents $R_1$ and $R_2$ are defined in Table B, constituting the disclosure of 34 specific compounds of formula $XXXIX_{609}$.

TABLE 610

A further preferred group of compounds of
formula XXXIX corresponds to the general formula

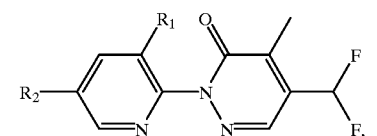
($I_{610}$)

wherein substituents $R_1$ and $R_2$ are defined in Table B, constituting the disclosure of 34 specific compounds of formula $XXXIX_{610}$.

TABLE 611

A further preferred group of compounds of
formula XXXIX corresponds to the general formula

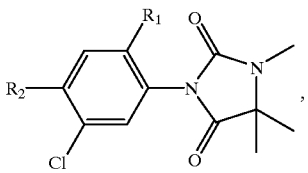
($I_{611}$)

wherein substituents $R_1$ and $R_2$ are defined in Table B, constituting the disclosure of 34 specific compounds of formula $XXXIX_{611}$.

TABLE 612

A further preferred group of compoumnds of
formula XXXIX corresponds to the general formula

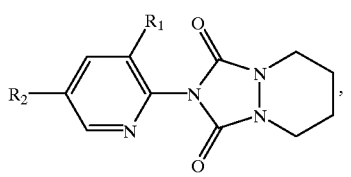
($XXXIX_{612}$)

wherein substituents $R_1$ and $R_2$ are defined in Table B, constituting the disclosure of 34 specific compounds of formula $XXXIX_{612}$.

TABLE 613

A further preferred group of compoumnds of
formula XXXIX corresponds to the general formula

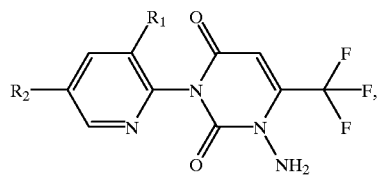
($XXXIX_{613}$)

wherein substituents $R_1$ and $R_2$ are defined in Table B, constituting the disclosure of 34 specific compounds of formula $XXXIX_{613}$.

TABLE 614

A further preferred group of compoumnds of
formula XXXIX corresponds to the general formula

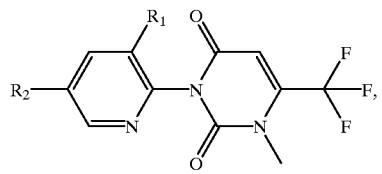
($XXXIX_{614}$)

wherein substituents $R_1$ and $R_2$ are defined in Table B, constituting the disclosure of 34 specific compounds of formula $XXXIX_{614}$.

TABLE 615

A further preferred group of compoumnds of formula XXXIX corresponds to the general formula

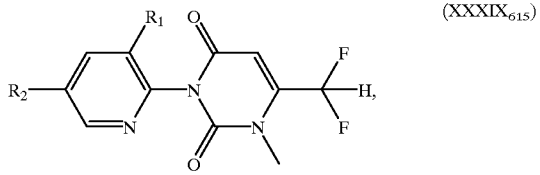

(XXXIX$_{615}$)

wherein substituents R$_1$ and R2 are defined in Table B, constituting the disclosure of 34 specific compounds of formula XXXIX$_{615}$.

TABLE 616

A further preferred group of compoumnds of formula XXXIX corresponds to the general formula

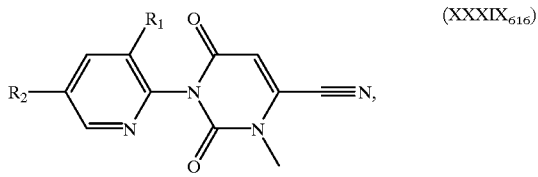

(XXXIX$_{616}$)

wherein substituents R$_1$ and R$_2$ are defined in Table B, constituting the disclosure of 34 specific compounds of formula XXXIX$_{616}$.

TABLE 617

A further preferred group of compoumnds of formula XXXIX corresponds to the general formula

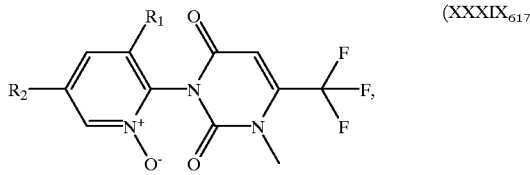

(XXXIX$_{617}$)

wherein substituents R$_1$ and R$_2$ are defined in Table A, constituting the disclosure of 34 specific compounds of formula XXXX$_{617}$.

TABLE 618

A further preferred group of compoumnds of formula XXXIX corresponds to the general formula

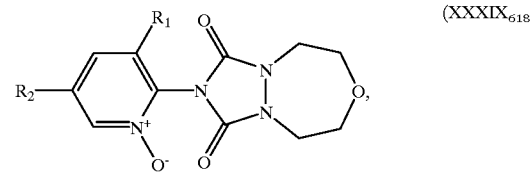

(XXXIX$_{618}$)

wherein substituents R$_1$ and R$_2$ are defined in Table B, constituting the disclosure of 34 specific compounds of formula XXXX$_{618}$.

TABLE 619

A further preferred group of compoumnds of formula XXXIX corresponds to the general formula

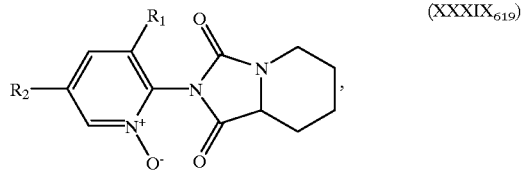

(XXXIX$_{619}$)

wherein substituents R$_1$ and R$_2$ are defined in Table B, constituting the disclosure of 34 specific compounds of formula XXXX$_{619}$.

TABLE 620

A further preferred group of compoumnds of formula XXXIX corresponds to the general formula

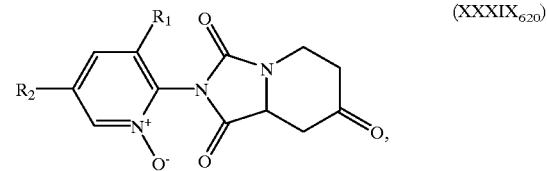

(XXXIX$_{620}$)

wherein substituents R$_1$ and R$_2$ are defined in Table B, constituting the disclosure of 34 specific compounds of formula XXXX$_{620}$.

TABLE 621

A further preferred group of compoumnds of formula XXXIX corresponds to the general formula

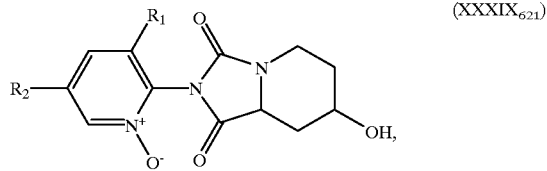

(XXXIX$_{621}$)

wherein substituents R$_1$ and R$_2$ are defined in Table B, constituting the disclosure of 34 specific compounds of formula XXXX$_{621}$.

TABLE 622

A further preferred group of compoumnds of formula XXXIX corresponds to the general formula

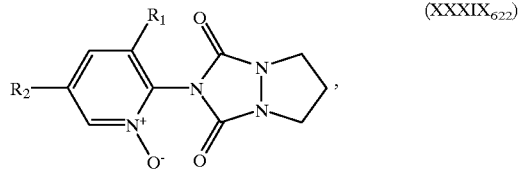

(XXXIX$_{622}$)

wherein substituents R$_1$ and R$_2$ are defined in Table B, constituting the disclosure of 34 specific compounds of formula XXXX$_{622}$.

TABLE 623

A further preferred group of compoumnds of formula XXXIX corresponds to the general formula

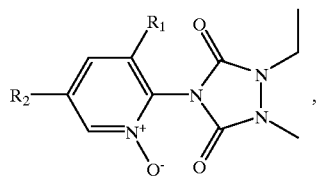
(XXXIX$_{623}$)

wherein substituents $R_1$ and $R_2$ are defined in Table B, constituting the disclosure of 34 specific compounds of formula XXXX$_{623}$.

TABLE 624

A further preferred group of compoumnds of formula XXXIX corresponds to the general formula

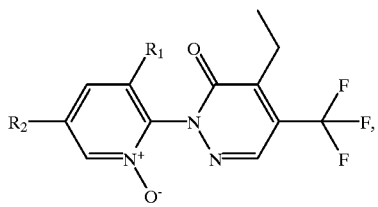
(XXXIX$_{624}$)

wherein substituents $R_1$ and $R_2$ are defined in Table B, constituting the disclosure of 34 specific compounds of formula XXXX$_{624}$.

TABLE 625

A further preferred group of compoumnds of formula XXXIX corresponds to the general formula

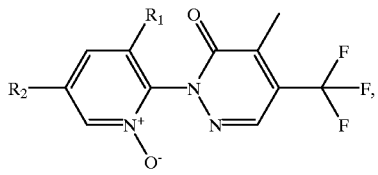
(XXXIX$_{625}$)

wherein substituents $R_1$ and $R_2$ are defined in Table B, constituting the disclosure of 34 specific compounds of formula XXXX$_{625}$.

TABLE 626

A further preferred group of compoumnds of formula XXXIX corresponds to the general formula

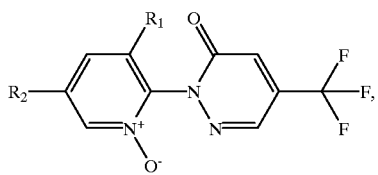
(XXXIX$_{626}$)

wherein substituents $R_1$ and $R_2$ are defined in Table B, constituting the disclosure of 34 specific compounds of formula XXXX$_{626}$.

TABLE 627

A further preferred group of compoumnds of formula XXXIX corresponds to the general formula

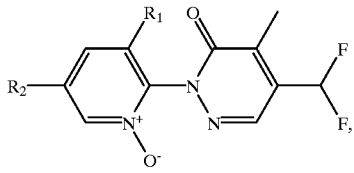
(XXXIX$_{627}$)

wherein substituents $R_1$ and $R_2$ are defined in Table B, constituting the disclosure of 34 specific compounds of formula XXXX$_{627}$.

TABLE 628

A further preferred group of compounds of formula XXXX corresponds to the general formula

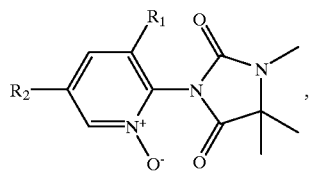
(XXXX$_{628}$)

wherein substituents $R_1$ and $R_2$ are defined in Table B, constituting the disclosure of 34 specific compounds of formula XXXX$_{628}$.

TABLE 629

A further preferred group of compounds of formula XXXX corresponds to the general formula

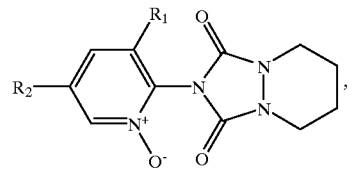
(XXXX$_{629}$)

wherein substituents $R_1$ and $R_2$ are defined in Table B, constituting the disclosure of 34 specific compounds of formula XXXX$_{629}$.

TABLE 630

A further preferred group of compounds of formula XXXX corresponds to the general formula

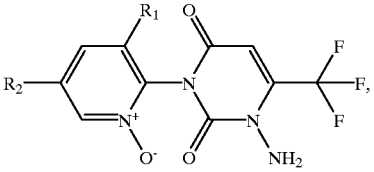
(XXXX$_{630}$)

wherein substituents $R_1$ and $R_2$ are defined in Table B, constituting the disclosure of 34 specific compounds of formula XXXX$_{630}$.

TABLE 631

A further preferred group of compounds of formula XXXX corresponds to the general formula

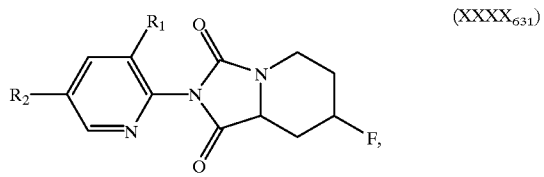

(XXXX$_{631}$)

wherein substituents $R_1$ and $R_2$ are defined in Table B, constituting the disclosure of 34 specific compounds of formula XXXIX$_{631}$.

TABLE 632

A further preferred group of compounds of formula XXXX corresponds to the general formula

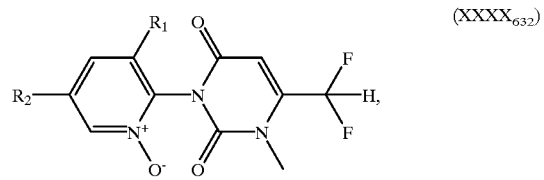

(XXXX$_{632}$)

wherein substituents $R_1$ and $R_2$ are defined in Table B, constituting the disclosure of 34 specific compounds of formula XXXX$_{632}$.

TABLE 633

A further preferred group of compounds of formula XXXX corresponds to the general formula

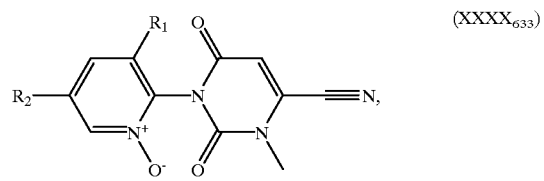

(XXXX$_{633}$)

wherein substituents $R_1$ and $R_2$ are defined in Table B, constituting the disclosure of 34 specific compounds of formula XXXX$_{633}$.

TABLE 634

A further preferred group of compounds of formula XXXX corresponds to the general formula

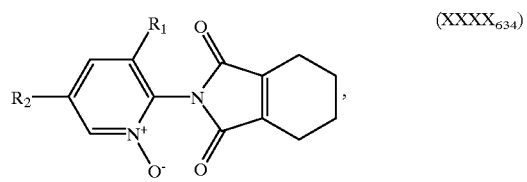

(XXXX$_{634}$)

wherein substituents $R_1$ and $R_2$ are defined in Table B, constituting the disclosure of 34 specific compounds of formula XXXX$_{634}$.

TABLE 635

A further preferred group of compounds of formula XXXX corresponds to the general formula

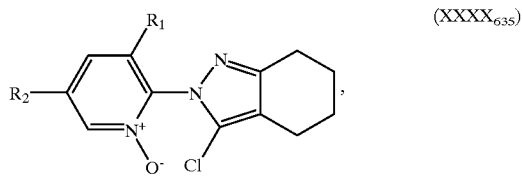

(XXXX$_{635}$)

wherein substituents $R_1$ and $R_2$ are defined in Table B, constituting the disclosure of 34 specific compounds of formula XXXX$_{635}$.

TABLE 636

A further preferred group of compounds of formula XXXX corresponds to the general formula

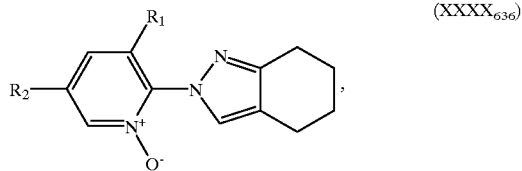

(XXXX$_{636}$)

wherein substituents $R_1$ and $R_2$ are defined in Table B, constituting the disclosure of 34 specific compounds of formula XXXX$_{636}$.

TABLE 637

A further preferred group of compounds of formula XXXX corresponds to the general formula

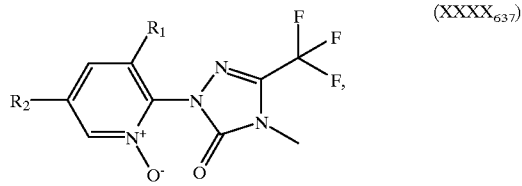

(XXXX$_{637}$)

wherein substituents $R_1$ and $R_2$ are defined in Table B, constituting the disclosure of 34 specific compounds of formula XXXx$_{637}$.

TABLE 638

A further preferred group of compounds of formula XXXX corresponds to the general formula

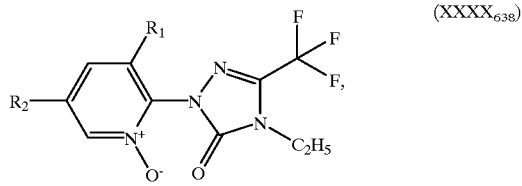

(XXXX$_{638}$)

wherein substituents $R_1$ and $R_2$ are defined in Table B, constituting the disclosure of 34 specific compounds of formula XXXX$_{638}$.

TABLE 639

A further preferred group of compounds of
formula XXXX corresponds to the general formula

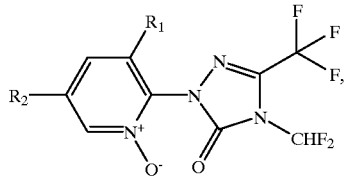
(XXXX$_{639}$)

wherein substituents R$_1$ and R$_2$ are defined in Table B, constituting the disclosure of 34 specific compounds of formula XXXX$_{639}$.

TABLE 640

A further preferred group of compounds of
formula XXXX corresponds to the general formula

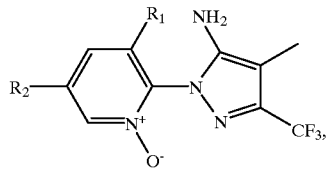
(XXXX$_{640}$)

wherein substituents R$_1$ and R$_2$ are defined in Table B, constituting the disclosure of 34 specific compounds of formula XXXX$_{640}$.

TABLE 641

A further preferred group of compounds of
formula XXXX corresponds to the general formula

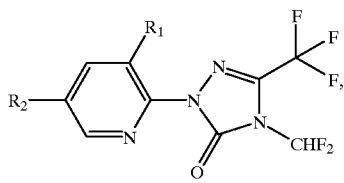
(XXXX$_{641}$)

wherein substituents R$_1$ and R$_2$ are defined in Table A, constituting the disclosure of 34 specific compounds of formula XXXIX$_{641}$.

TABLE 642

A further preferred group of compounds of
formula XXXX corresponds to the general formula

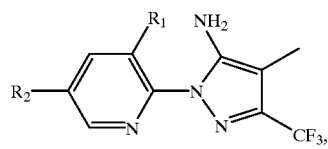
(XXXX$_{642}$)

wherein substituents R$_1$ and R$_2$ are defined in Table B, constituting the disclosure of 34 specific compounds of formula XXXIX$_{642}$.

TABLE 643

A further preferred group of compounds of
formula XXXX corresponds to the general formula

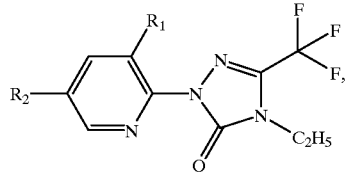
(XXXX$_{643}$)

wherein substituents R$_1$ and R$_2$ are defined in Table B, constituting the disclosure of 34 specific compounds of formula XXXIX$_{643}$.

TABLE 644

A further preferred group of compounds of
formula XXXIX corresponds to the general formula

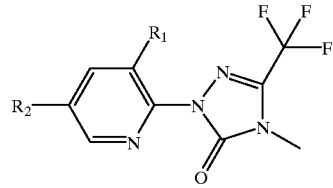
(XXXIX$_{644}$)

wherein substituents R$_1$ and R$_2$ are defined in Table B, constituting the disclosure of 34 specific compounds of formula XXXX$_{644}$.

TABLE 645

A further preferred group of compounds of
formula I corresponds to the general formula

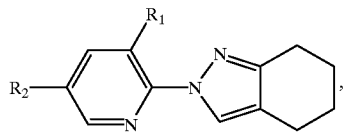
(XXXIX$_{645}$)

wherein substituents R$_1$ and R$_2$ are defined in Table A, constituting the disclosure of 34 specific compounds of formula XXXIX$_{645}$.

TABLE 646

A further preferred group of compounds of
formula I corresponds to the general formula

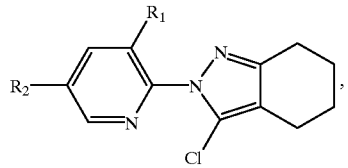
(XXXIX$_{646}$)

wherein substituents R$_1$ and R$_2$ are defined in Table A, constituting the disclosure of 34 specific compounds of formula XXXIX$_{646}$.

TABLE 647

A further preferred group of compounds of formula I corresponds to the general formula

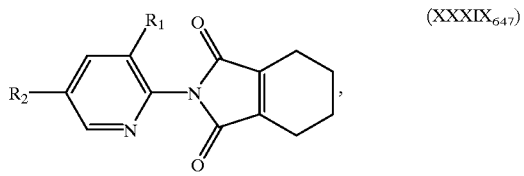

(XXXIX$_{647}$)

wherein substituents $R_1$ and $R_2$ are defined in Table A, constituting the disclosure of 34 specific compounds of formula XXXIX$_{647}$.

TABLE B

| Cpmd no. | $R_1$ | $R_2$ |
|---|---|---|
| .001 | F | Cl |
| .002 | F | CN |
| .003 | F | OCH$_3$ |
| .004 | F | OCF$_3$ |
| .005 | F | CF$_3$ |
| .006 | F | Br |
| .007 | F | NO$_2$ |
| .008 | F | CH$_3$ |
| .010 | F | OCH$_2$≡CH |
| .011 | Cl | CN |
| .012 | Cl | OCH$_3$ |
| .013 | Cl | OCF$_3$ |
| .014 | Cl | CF$_3$ |
| .015 | Cl | Br |
| .016 | Cl | NO$_2$ |
| .017 | Cl | CH$_3$ |
| .018 | Cl | Cl |
| .019 | Cl | CF$_2$H |
| .020 | H | F |
| .021 | H | Cl |
| .022 | H | Br |
| .023 | H | CF$_3$ |
| .024 | H | OCF$_3$ |
| .025 | H | NO$_2$ |
| .026 | H | CN |
| .027 | H | i-Pr |
| .028 | F | C$_2$H$_5$ |
| .029 | F | OCH$_2$CF$_3$ |
| .030 | H | OCH$_2$CF$_3$ |
| .031 | H | t-Bu |
| .032 | F | t-Bu |
| .033 | Cl | t-Bu |
| .034 | H | J |

TABLE C

Physicochemical data for prepared compounds from the above tables. The figure before the point indicates the number of the table, e.g. 1.004 means in Table 1 compound no. 004 of Table A and 634.001 means in Table 634 compound nb. 001 of Table B.

| Cmpd no. | physic. data |
|---|---|
| 1.004 | nD(40° C.) 1.5159 |
| 1.038 | αD(20° C.) + 10.10 |
| 1.352 | m.p. 110–112° C. |
| 35.004 | $^1$H-NMR (CDCl$_3$): 8.11 ppm (s, 1H); 7.80 ppm (d, 1H); 7.35 ppm (s, 1H); 4.46 ppm (q, 2H); 1.41 ppm (t, 3H) |
| 600.001 | m.p. 133–134° C. |
| 608.001 | m.p. 91–93° C. |
| 609.001 | m.p. 114–116° C. |
| 617.001 | m.p. 143–145° C. |
| 625.001 | m.p. 140–143° C. |
| 626.001 | m.p. 143–145° C. |

TABLE C-continued

Physicochemical data for prepared compounds from the above tables. The figure before the point indicates the number of the table, e.g. 1.004 means in Table 1 compound no. 004 of Table A and 634.001 means in Table 634 compound nb. 001 of Table B.

| Cmpd no. | physic. data |
|---|---|
| 631.001 | m.p. 154–157° C. |
| 634.001 | m.p. 162–164° C. |

Examples of specific formulations for active ingredients of formula I such as emulsifiable concentrates, solutions, wettable powders, coating granules, extruder granulates, dusts and suspension concentrates, are described in WO 97/34485 on pages 9–13.

Biological Examples

Example B1

Preemergence Herbicidal Action

Monocot and dicot test plants are sown in standard soil in plastic pots. Immediately after sowing, the plants are sprayed at a concentration of 2 kg active ingredient/ha with an aqueous suspension of the test compound prepared from a 25% wettable powder (Example F3, b)) according to WO 97/34485) or an emulsion of the test compound prepared from a 25% emulsifiable concentrate (Example F1 c)) according to WO 97/34485) (500 l of water/ha). The test plants are then cultivated in the greenhouse under optimum conditions. The test is evaluated 3 weeks later on a rating scale of 1–9 (1=total damage, 9=no action). Ratings of 1 to 4 (especially of 1 to 3) denote good to very good herbicidal action.

Test plants: Lolium, Setaria, Sinapis, Solanum, Ipomea.

The compounds of the invention show good herbicidal action.

An example of good herbicidal efficacy of compounds of formula I is given in Table B1.

TABLE B1

Pre-emergent action:

| Cmpd No. | Lolium | Setaria | Sinapis | Solanum | Ipomea | Dose [g a.i./ha] |
|---|---|---|---|---|---|---|
| 1.004 | 2 | 1 | 1 | 1 | 1 | 2000 |
| 1.038 | 7 | 1 | 1 | 2 | 3 | 2000 |
| 1.352 | 1 | 1 | 1 | 1 | 1 | 2000 |

The same results are obtained by formulating the compounds of formula I in accordance with Examples F2 and F4 to F8 as described in WO 97/34485.

Example B2

Post-emergent Herbicidal Action

In a greenhouse, monocot and dicot test plants are sown in standard soil in plastic pots and sprayed in the 4- to 6-leaf stage with an aqueous suspension of the test compounds of formula I prepared from a 25% wettable powder (Example F3, b) according to WO 97/34485) or with an emulsion of the test compound prepared from a 25% emulsifiable concentrate (Example F1 c)) according to WO 97/34485 ) at a concentration of 2 kg a.i./ha (500 l of water/ha). The test plants are then further cultivated in the greenhouse under optimum conditions. The test is evaluated about 18 days later on a rating scale of 1–9 (1=total damage, 9=no action).

Ratings of 1 to 4 (especially of 1 to 3) denote good to very good herbicidal action. In this test the compounds of formula I exhibit a pronounced herbicidal action.

Test plants: Lolium, Setaria, Sinapis, Solanum, Ipomea.

In this test too the compounds of formula I exhibit a pronounced herbicidal action.

An example of good herbicidal efficacy of compounds of formula I is given in Table B2.

TABLE B2

| | Post-emergente action: | | | | | |
|---|---|---|---|---|---|---|
| | Test plant: | | | | | Dose |
| Cmpd No. | Lolium | Setaria | Sinapis | Solanum | Ipomea | [g a.i./ha] |
| 1.004 | 1 | 1 | 1 | 1 | 1 | 2000 |
| 1.038 | 1 | 1 | 1 | 1 | 1 | 2000 |
| 1.352 | 1 | 1 | 1 | 1 | 1 | 2000 |

The same results are obtained by formulating the compounds of formula I in accordance with Examples F2 and F4 to F8 as described in WO 97/34485.

The active ingredients of formula I can also be used for weed control by mixing with known herbicides as co-herbicides, for example as ready-for-use formulations or as tank mix. Suitable compounds for mixing with active ingredients of formula I are for example the following co-herbicides: compound of formula I+acetochlor; compound of formula I+acifluorfen; compound of formula I+aclonifen; compound of formula I+alachlor; compound of formula I+ametryn; compound of formula I+aminotriazol; compound of formula I+amidosulfuron; compound of formula I+asulam; compound of formula I+atrazine; compound of formula I+BAY FOE 5043; compound of formula I+benazolin; compound of formula I+bensulfuron; compound of formula I+bentazone; compound of formula I+bifenox; compound of formula I+bispyribac sodium; compound of formula I+bialaphos; compound of formula I+bromacil; compound of formula I+bromoxynil; compound of formula I+bromophenoxim; compound of formula I+butachlor; compound of formula I+butylate; compound of formula I+cafenstrole; compound of formula I+carbetamide; compound of formula I+chloridazone; compound of formula I+chlorimuron ethyl; compound of formula I+chlorbromuron; compound of formula I+chlorsulfuron; compound of formula I+chlortoluron; compound of formula I+cinosulfuron; compound of formula I+clethodim; compound of formula I+clodinafop; compound of formula I+clomazone; compound of formula I+clopyralid; compound of formula I+cloransulam; compound of formula I+cyanazine; compound of formula I+cyhalofop; compound of formula I+dalapon; compound of formula I+2,4-D; compound of formula I+2,4-DB; compound of formula I+desmetryn; compound of formula I+desmedipham; compound of formula I+dicamba; compound of formula I+diclofop; compound of formula I+difenzoquat methyl sulfate; compound of formula I+diflufenican; compound of formula I+dimefuron; compound of formula I+dimepiperate; compound of formula I+dimethachlor; compound of formula I+dimethametryn; compound of formula I+dimethenamid; compound of formula I+S-dimethenamid; compound of formula I+dinitramine; compound of formula I+dinoterb; compound of formula I+dipropetryn; compound of formula I+diuron; compound of formula I+diquat; compound of formula I+DSMA; compound of formula I+EPTC; compound of formula I+esprocarb; compound of formula I+ethalfluralin; compound of formula I+ethametsulfuron; compound of formula I+ethephon; compound of formula I+ethofumesate; compound of formula I+ethoxysulfuron; compound of formula I+fenclorim; compound of formula I+flamprop; compound of formula I+fluazasulfuron; compound of formula I+fluazifop; compound of formula I+flumetralin; compound of formula I+flumetsulam; compound of formula I+fluometuron; compound of formula I+flurchloridone; compound of formula I+fluoxaprop; compound of formula I+fluroxypyr; compound of formula I+fluthiacet-methyl; compound of formula I+fluxofenim; compound of formula I+fomesafen; compound of formula I+glufosinate; compound of formula I+glyphosate; compound of formula I+halosulfuron; compound of formula I+haloxyfop; compound of formula I+hexazinone; compound of formula I+imazamethabenz; compound of formula I+imazapyr; compound of formula I+imazaquin; compound of formula I+imazethapyr; compound of formula I+imazosulfuron; compound of formula I+ioxynil; compound of formula I+isoproturon; compound of formula I+isoxaben; compound of formula I+isoxaflutole; compound of formula I+karbutylate; compound of formula I+lactofen; compound of formula I+lenacil; compound of formula I+linuron; compound of formula I+MCPP; compound of formula I+metamitron; compound of formula I+metazachlor; compound of formula I+methabenzthiazuron; compound of formula I+methazole; compound of formula I+metobromuron; compound of formula I+metolachlor; compound of formula I+S-metolachlor; compound of formula I+metosulam; compound of formula I+metribuzin; compound of formula I+metsulfuron methyl; compound of formula I+molinate; compound of formula I+MCPA; compound of formula I+MSMA; compound of formula I+napropamide; compound of formula I+NDA-402989; compound of formula I+n; compound of formula I+nicosulfuron; compound of formula I+norflurazon; compound of formula I+oryzalin; compound of formula I+oxadiazon; compound of formula I+oxasulfuron; compound of formula I+oxyfluorfen; compound of formula I+paraquat; compound of formula I+pendimethalin; compound of formula I+phenmedipham; compound of formula I+phenoxaprop-P-ethyl (R); compound of formula I+picloram; compound of formula I+pretilachlor; compound of formula I+primisulfuron; compound of formula I+prometon; compound of formula I+prometryn; compound of formula I+propachlor; compound of formula I+propanil; compound of formula I+propazine; compound of formula I+propaquizafop; compound of formula I+propyzamide; compound of formula I+prosulfuron; compound of formula I+pyrazolynate; compound of formula I+pyrazosulfuron ethyl; compound of formula I+pyrazoxyphen; compound of formula I+pyridate; compound of formula I+pyriminobac methyl; compound of formula I+pyrithiobac sodium; compound of formula I+quinclorac; compound of formula I+quizalofop; compound of formula I+rimsulfuron; compound of formula I+sequestren; compound of formula I+sethoxydim; compound of formula I+simetryn; compound of formula I+simazin; compound of formula I+sulcotrione; compound of formula I+sulfosate; compound of formula I+sulfosulfuron methyl; compound of formula I+tebutam; compound of formula I+tebuthiuron; compound of formula I+terbacil; compound of formula I+terbumeton; compound of formula I+terbuthylazin; compound of formula I+terbutryn; compound of formula I+thiazafluron; compound of formula I+thiazopyr; compound of formula I+thifensulfuron methyl; compound of formula I+thiobencarb; compound of formula I+tralkoxydim; compound of formula I+triallate; compound of formula I+triasulfuron; compound of formula I+trifluralin; compound of formula I+tribenuron methyl; compound of formula I+triclopyr; compound of formula I+triflusulfuron; compound of formula I+trinexapac ethyl, as well as esters and salts of these compounds for mixing with a compound of formula I, which named for example in The Pesticide Manual, Eleventh Edition, 1997, BCPC.

What is claimed is:

1. A compound of formula I

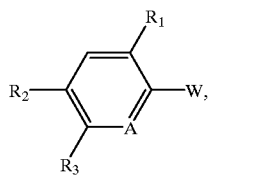

(I)

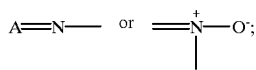

$R_1$ is hydrogen, fluorine, chlorine, bromine or methyl;
$R_2$ is $C_1$–$C_4$alkyl, $C_1$–$C_4$halogenalkyl or halogen;
$R_3$ is cyano or $R_4C(O)$—;
$R_4$ is hydrogen, fluorine, chlorine, $C_1$–$C_8$alkyl, $C_2$–$C_8$alkenyl, $C_2$–$C_8$alkinyl, $C_3$–$C_6$cycloalkyl, $C_1$–$C_8$halogenalkyl, cyano-$C_1$–$C_4$alkyl, $C_2$–$C_8$halogenalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl substituted once to three times by halogen, $C_1$–$C_4$alkyl or $C_1$–$C_4$halogenalkyl, benzyl or benzyl substituted once to three times on the phenyl ring by halogen, $C_1$–$C_4$alkyl or $C_1$–$C_4$halogenalkyl; or
$R_3$ is $R_5X_1C(O)$—;
$X_1$ is oxygen, sulfur,

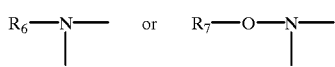

$R_5$ is hydrogen, $C_1$–$C_8$alkyl, $C_3$–$C_8$alkenyl, $C_3$–$C_8$alkinyl, $C_3$–$C_6$cycloalkyl, $C_3$–$C_6$cycloalkyl-$C_1$–$C_6$alkyl, $C_1$–$C_8$halogenalkyl, $C_3$–$C_8$halogenalkenyl, cyano-$C_1$–$C_4$alkyl, $C_1$–$C_4$alkoxy-$C_1$–$C_4$alkyl, $C_3$–$C_6$alkenyloxy-$C_1$–$C_4$alkyl, (oxiranyl)-$CH_2$—, oxetanyl-, $C_1$–$C_4$alkylthio-$C_1$–$C_4$alkyl, phenyl, phenyl substituted once to three times by halogen, $C_1$–$C_4$alkyl or $C_1$–$C_4$halogenalkyl, benzyl or benzyl substituted once to three times on the phenyl ring by halogen, $C_1$–$C_4$alkyl or $C_1$–$C_4$-halogenalkyl, phenyl-$C_2$–$C_6$alkyl, $C_1$–$C_6$alkyl-CO—$C_1$–$C_4$alkyl,

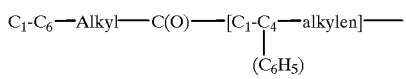

$R_8X_2C(O)$—$C_1$–$C_6$-alkyl,

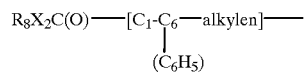

or $R_8X_2C(O)$—$C_3$–$C_6$cycloalkyl;
$X_2$ is oxygen, sulfur,

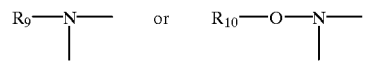

$R_8$ is hydrogen, $C_1$–$C_8$alkyl, $C_3$–$C_8$alkenyl, $C_3$–$C_8$alkinyl, $C_3$–$C_6$cycloalkyl, $C_1$–$C_8$halogenalkyl, $C_3$–$C_8$halogenalkenyl, cyano-$C_1$–$C_4$alkyl, $C_1$–$C_4$alkoxy-$C_1$–$C_4$alkyl, $C_3$–$C_6$alkenyloxy-$C_1$–$C_4$alkyl, (oxiranyl)-$CH_2$—, oxetanyl, $C_1$–$C_4$alkylthio-$C_1$–$C_4$alkyl, phenyl, phenyl substituted once to three times by halogen, $C_1$–$C_4$alkyl or $C_1$–$C_4$halogenalkyl, benzyl, benzyl substituted once to three times on the phenyl ring by halogen, $C_1$–$C_4$alkyl or $C_1$–$C_4$halogenalkyl, or phenyl-$C_2$–$C_6$alkyl; $R_6$, $R_7$, $R_9$ and $R_{10}$ are independently of one another hydrogen, $C_1$–$C_8$alkyl, $C_3$–$C_8$alkenyl, $C_3$–$C_8$alkinyl, $C_1$–$C_8$halogenalkyl or benzyl; or
$R_3$ is $B_1$—$C_1$–$C_8$alkyl, $B_1$—$C_2$–$C_8$alkenyl, $B_1$—$C_2$–$C_8$alkinyl, $B_1$—$C_1$–$C_8$halogenalkyl, $B_1$—$C_2$–$C_8$halogenalkenyl, $B_1$—$C_1$–$C_4$alkoxy-$C_1$–$C_4$alkyl, $B_1$—$C_1$–$C_4$alkylthio-$C_1$–$C_4$alkyl or $B_1$—$C_3$–$C_6$cycloalkyl;
$B_1$ is hydrogen, cyano, hydroxy, $C_1$–$C_8$alkoxy, $C_3$–$C_8$alkenyloxy, $R_{11}X_3C(O)$—, $C_1$–$C_4$alkylcarbonyl or $C_1$–$C_4$halogenalkylcarbonyl;
$X_3$ has the same meaning as $X_2$;
$R_{11}$ has the same meaning as $R_8$; or
$R_3$ is $B_2$—$C(R_{12})$=$CH$—;
$B_2$ is nitro, cyano or $R_{13}X_4C(O)$—;
$R_{12}$ is cyano or $R_{14}X_5C(O)$—;
$X_4$ and $X_5$ have the same meaning as $X_2$; and
$R_{13}$ and $R_{14}$ have the same meaning as $R_8$;

W is a

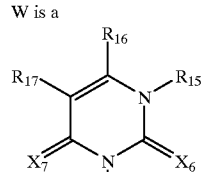

(W$_1$)

or

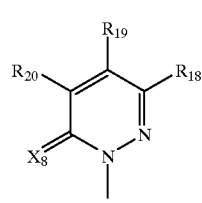

(W$_2$)

$R_{15}$ is $C_1$–$C_3$alkyl, $C_1$–$C_3$halogenalkyl or amino;
$R_{16}$ is $C_1$–$C_3$halogenalkyl, $C_1$–$C_3$alkyl-$S(O)_{n1}$, $C_1$–$C_3$halogenalkyl-$S(O)_{n1}$ or cyano; or $R_{16}$ and $R_{15}$ together form a $C_3$— or $C_4$alkylene or $C_3$— or $C_4$alkenylene bridge which may be substituted by halogen, $C_1$–$C_3$halogenalkyl or cyano;

$n_1$ is 0, 1 or 2;

$R_{17}$ is hydrogen, $C_1$–$C_3$alkyl, halogen, $C_1$–$C_3$halogenalkyl or cyano; or $R_{17}$ and $R_{16}$ together form a $C_3$— or $C_4$alkylene or $C_3$— or $C_4$alkenylene bridge which may be substituted by halogen, $C_1$–$C_3$halogenalkyl or cyano;

$R_{18}$ is hydrogen, $C_1$–$C_3$alkyl, halogen or cyano;

$R_{19}$ is $C_1$–$C_3$halogenalkyl; or $R_{19}$ and $R_{18}$ together form a $C_3$— or $C_4$alkylene or $C_3$— or $C_4$alkenylene bridge which may be substituted by halogen, $C_1$–$C_3$halogenalkyl or cyano;

$R_{20}$ is hydrogen or $C_1$–$C_3$alkyl or halogen; or $R_{20}$ and $R_{19}$ together form a $C_3$— or $C_4$alkylene or $C_3$— or $C_4$alkenylene bridge which may be substituted by halogen, $C_1$–$C_3$halogenalkyl or cyano; and $X_6$, $X_7$, and $X_8$ are independently of one another oxygen or sulfur, and the agrochemically acceptable salts and stereoisomers of these compounds of formula I.

2. A compound of formula I of claim 1, wherein $R_2$ is methyl or halogen.

3. A method for the preparation of compounds of formula I,

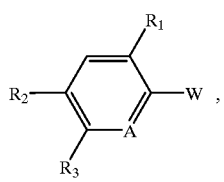

(I)

wherein $R_1$, $R_2$, $R_3$, A and W are as defined in claim 1, comprising treating a compound of formula II

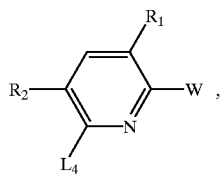

(II)

wherein $R_1$, $R_2$ and W have the meanings indicated, and $L_4$ is a leaving group, either a) in a suitable solvent, where appropriate in the presence of a base, a catalyst and a compound of formula V $R_5$—OH (V), wherein $R_5$ is hydrogen or $C_1$–$C_4$alkyl, under positive pressure with carbon monoxide, or b) in a suitable solvent in the presence of a tertiary amine, a catalyst, and an olefin by means of the Heck reaction, or under said conditions by means of reaction with a Grignard reagent of formula Va $R_3$—Mg-halogenide (Va), wherein $R_3$ is $B_1$—$C_1$–$C_8$alkyl, $B_1$—$C_2$–$C_8$alkenyl, $B_1$—$C_2$–$C_8$alkinyl, $B_1$—$C_1$–$C_8$halogenalkyl, $B_1$—$C_2$–$C_8$halogenalkenyl, $B_1$—$C_1$–$C_4$alkoxy-$C_1$–$C_4$alkyl, $B_1$—$C_1C_4$alkylthio-$C_1$–$C_4$alkyl or $B_1$—$C_3$–$C_6$cycloalkyl and $B_1$ has the meaning defined in claim I, or in an inert solvent and in the presence of a catalyst with a tin compound of formula Vb $(R_3)_4Sn$ (Vb), wherein $R_3$ has the meaning indicated, or c) where applicable in an inert solvent at reaction temperatures of 20–300° C. subjecting said compound to a cyanidation reaction, or d) first oxidizing said compound in a suitable solvent to form a compound of formula IV

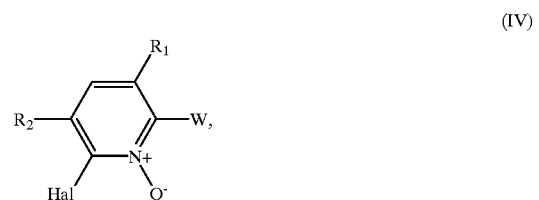

(IV)

and treating this in an inert solvent with dimethylcarbamoyl chloride and a cyanidation reagent, and then where applicable further functionalizing the compound according to the definitions of A and $R_3$.

4. A herbicidal and plant growth inhibiting composition, which comprises a herbicidally effective amount of the compound of formula I on an inert carrier.

5. A herbicidal and plant growth inhibiting composition of claim 4 comprising as an additional component a further co-herbicide.

6. A method of controlling undesirable plant growth, which comprises treating the plants or the locus thereof with a herbicidally effective amount of a compound of formula I of claim 1 or of a composition containing such a compound.

* * * * *